(12) United States Patent
Kehler et al.

(10) Patent No.: US 7,652,150 B2
(45) Date of Patent: *Jan. 26, 2010

(54) 2-(1H-INDOLYLSULFANYL)-BENZYL AMINE DERIVATIVES AS SSRIS

(75) Inventors: Jan Kehler, Kgs. Lyngby (DK); Karsten Juhl, Greve (DK); Morten Bang Norgaard, Kgs. Lyngby (DK); Jimmy Sejberg, Rødøvre (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

This patent is subject to a terminal disclaimer.

(21) Appl. No.: 12/044,170

(22) Filed: Mar. 7, 2008

(65) Prior Publication Data

US 2008/0214644 A1    Sep. 4, 2008

Related U.S. Application Data

(63) Continuation of application No. 11/314,702, filed on Dec. 21, 2005, now Pat. No. 7,563,908, which is a continuation of application No. PCT/DK2004/000894, filed on Dec. 21, 2004.

(60) Provisional application No. 60/532,593, filed on Dec. 23, 2003.

(30) Foreign Application Priority Data

Dec. 23, 2003   (DK) .............................. 2003 01923

(51) Int. Cl.
   *C07D 209/30* (2006.01)
(52) U.S. Cl. ...................... 548/484; 548/507
(58) Field of Classification Search ................ 548/484, 548/507
   See application file for complete search history.

(56) References Cited

U.S. PATENT DOCUMENTS

| | | | |
|---|---|---|---|
| 3,803,143 | A | 4/1974 | Tanaka et al. |
| 4,018,830 | A | 4/1977 | Christy |
| 4,055,665 | A | 10/1977 | Christy |
| 4,056,632 | A | 11/1977 | Mehta et al. |
| 4,198,417 | A | 4/1980 | Ong et al. |
| 4,241,071 | A | 12/1980 | Martin et al. |
| 5,095,039 | A | 3/1992 | Mehta et al. |
| 5,945,425 | A | 8/1999 | Moormann et al. |
| 6,410,736 | B1 | 6/2002 | Howard, Jr. et al. |
| 6,436,938 | B1 | 8/2002 | Howard, Jr. et al. |
| 6,455,738 | B1 | 9/2002 | Dubac et al. |
| 6,509,340 | B1 | 1/2003 | Van Amsterdam et al. |
| 6,596,741 | B2 | 7/2003 | Howard et al. |
| 6,906,078 | B2 | 6/2005 | Moorman et al. |
| 7,189,501 | B2 | 3/2007 | Makuta et al. |
| 7,199,147 | B2 | 4/2007 | Imazaki et al. |
| 7,217,732 | B2 | 5/2007 | Kozlowski et al. |
| 7,229,751 | B2 | 6/2007 | Kimura et al. |
| 7,247,651 | B2 | 7/2007 | Madera et al. |
| 2002/0173524 | A1 | 11/2002 | Collins et al. |
| 2003/0187023 | A1 | 10/2003 | Kubo et al. |
| 2003/0207894 | A1 | 11/2003 | Theodoridis et al. |
| 2004/0009959 | A1 | 1/2004 | Potter et al. |
| 2004/0014774 | A1 | 1/2004 | Myers et al. |
| 2004/0023010 | A1 | 2/2004 | Bulovic et al. |
| 2004/0039035 | A1 | 2/2004 | Collins et al. |
| 2004/0072844 | A1 | 4/2004 | Madera et al. |
| 2004/0077854 | A1 | 4/2004 | Halazy et al. |
| 2004/0132778 | A1 | 7/2004 | Lacadie et al. |
| 2004/0137389 | A1 | 7/2004 | Fukui et al. |
| 2004/0176426 | A1 | 9/2004 | Houze et al. |
| 2004/0186148 | A1 | 9/2004 | Shankar et al. |
| 2004/0192664 | A1 | 9/2004 | Kunz et al. |
| 2004/0204451 | A1 | 10/2004 | Lacadie et al. |
| 2004/0209936 | A1 | 10/2004 | Bratton et al. |
| 2004/0220237 | A1 | 11/2004 | Fu et al. |
| 2004/0266732 | A1 | 12/2004 | Galvez et al. |
| 2005/0107599 | A1 | 5/2005 | Makioka et al. |
| 2005/0123501 | A1 | 6/2005 | Lewis |
| 2005/0136065 | A1 | 6/2005 | Valiante, Jr. |
| 2005/0152859 | A1 | 7/2005 | Dooley et al. |
| 2005/0153980 | A1 | 7/2005 | Schadt et al. |
| 2005/0159556 | A1 | 7/2005 | Lewis et al. |
| 2005/0189519 | A1 | 9/2005 | Gothe et al. |
| 2005/0206994 | A1 | 9/2005 | Kokeguchi et al. |

(Continued)

FOREIGN PATENT DOCUMENTS

EP    0 273 199 A2    7/1988

(Continued)

OTHER PUBLICATIONS

Axford, L., et al. Bicyclo[2.2.1]heptanes as Novel Triple Re-uptake Inhibitors for the Treatment of Depression. Bioorganic & Medicinal Chemistry Letters. 2003. 13:3277-3280.

(Continued)

*Primary Examiner*—Rebecca L Anderson
*Assistant Examiner*—Shawquia Young
(74) *Attorney, Agent, or Firm*—Stephen G. Kalinchak; Margaret M. Buck

(57) ABSTRACT

The present invention relates to 2-(1H-indolylsulfanyl)-benzyl amine derivatives of general formula (I):

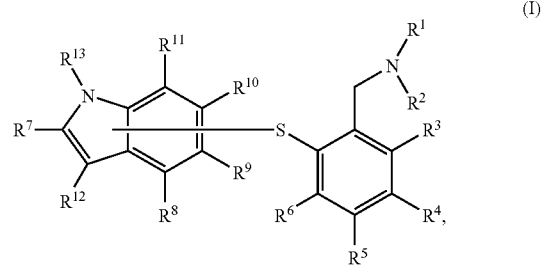

which are useful as SSRIs, and pharmaceutical compositions comprising the compounds.

19 Claims, No Drawings

U.S. PATENT DOCUMENTS

| | | | |
|---|---|---|---|
| 2005/0228020 A1 | 10/2005 | Miyamoto et al. |
| 2005/0238992 A1 | 10/2005 | Kodama |
| 2005/0250794 A1 | 11/2005 | Napper et al. |
| 2005/0261298 A1 | 11/2005 | Solow-Cordero et al. |
| 2005/0282861 A1 | 12/2005 | Friary et al. |
| 2006/0030593 A1 | 2/2006 | Bernotas et al. |
| 2006/0069203 A1 | 3/2006 | Lewis et al. |
| 2007/0004923 A1 | 1/2007 | Kobayashi et al. |
| 2007/0054224 A1 | 3/2007 | Yoneyama et al. |
| 2007/0054904 A1 | 3/2007 | Knolle et al. |
| 2007/0060595 A1 | 3/2007 | Yoshizawa et al. |

FOREIGN PATENT DOCUMENTS

| | | |
|---|---|---|
| EP | 0 396 827 A1 | 11/1990 |
| EP | 0 402 097 A1 | 12/1990 |
| EP | 0 755 923 A1 | 1/1997 |
| EP | 0 814 084 A1 | 12/1997 |
| EP | 0 921 124 A1 | 6/1999 |
| EP | 1 793 272 A1 | 6/2007 |
| WO | WO 93/11106 | 6/1993 |
| WO | WO 93/12080 A1 | 6/1993 |
| WO | WO 94/14770 | 7/1994 |
| WO | WO 97/17325 A1 | 5/1997 |
| WO | WO 97/17352 A1 | 5/1997 |
| WO | WO 97/48698 | 12/1997 |
| WO | WO 98/08817 A1 | 3/1998 |
| WO | WO 00/37456 A1 | 6/2000 |
| WO | WO 00/59878 A2 | 10/2000 |
| WO | WO 00/66537 A1 | 11/2000 |
| WO | WO 01/10842 A2 | 2/2001 |
| WO | WO 01/27068 A1 | 4/2001 |
| WO | WO 01/49677 A1 | 7/2001 |
| WO | WO 01/49678 A1 | 7/2001 |
| WO | WO 01/49679 A1 | 7/2001 |
| WO | WO 02/40024 A1 | 5/2002 |
| WO | WO 02/62766 A2 | 8/2002 |
| WO | WO 02/98857 A1 | 12/2002 |
| WO | WO 03/029232 A1 | 4/2003 |
| WO | WO 03/055873 A1 | 7/2003 |
| WO | WO 03/087086 A2 | 10/2003 |
| WO | WO 2006/006172 A2 | 1/2006 |
| WO | WO 2006/018850 A2 | 2/2006 |
| WO | WO 2006/022405 A1 | 3/2006 |
| WO | WO 2006/038741 A1 | 4/2006 |
| WO | WO 2006/063606 A1 | 6/2006 |

OTHER PUBLICATIONS

Emond, P., et al. Substituted Diphenyl Sulfides as Selective Serotonin Transporter Ligands: Synthesis and In Vitro Evaluation. J. Med. Chem. 2002. 45(6)1253-1258.

Hawkins, D.C., et al. Competitive Cyclisation of Singlet and Triplet Nitrenes. Part 7. Reaction Pathways of 2-Azidophenyl Benzothienyl Azides. J. Chem. Soc., Perkin Trans. I. 1979. 3207-3210.

Jackson, A., et al. Electrophilic Substitution in Indoles, Part 16, 1,2 The Formation of Indolobenzothiazines and Indolobenzothiazepines by Intramolecular Cyclisation of (o-Nitrophenylthio)indoles. J. Chem. Res. Miniprint 9. 1988. 2017-2063.

Jilek, J., et al. Potential Antidepressants: 2-(Methoxy- and Hydroxy-Phenylthio)Benzylamines as Selective Inhibitors of 5-Hydroxytryptamine Re-uptake in the Brain. Collect. Czech. Chem. Commun. 1989. 54:3294-3338.

Martin, L., et al. Synthesis of Spiro[isobenzofuran-1(3H),4'piperedines] as potential Central Nervous System Agents. 5. Conformationally Mobile Analogues Derived by Furan Ring Opening. J Med. Chem 1979 22(11).1347-1354.

Oya, S., et al. A New Single-Photon Emission Computed Tomography Imaging Agent for Serotonin Transporters: [123I]IDAM, 5-Iodo-2-((2-((dimethylamino)methyl)-phenyl)thio)benzyl Alcohol. J. Med. Chem. 1999. 42(3):333-335.

Oya, S., et al. New PET Imaging Agent for the Serotonin Transporter: [18F]ACF (2[(2- Amino-4-chloro-5-fluorophenyl)thio]-N,N-dimethyl-benzenmethanamine). J. Med. Chem. 2002. 45(21):4716-4723.

Ragno, R., et al. Docking and 3-D QSAR Studies on Indolyl Aryl Sulfones. Binding Mode Exploration at the HIV-1 Reverse Transcriptase Non-Nucleoside Binnding Site and Design of Higly Active N-(2-Hydroxyethyl) carboxamide and N-(2-hydroxyethyl)carbohydrazide Derivatives. J. Med. Chem. 2005. 48(1):213-223.

Silvestri, R., et al. Novel Indolyl Aryl Sulfones Active Against HIV-1 Carrying NNRTI Resistance Mutations: Synthesis and SAR Studies. J. Med. Chem. 2003. 46(12):2482-2493.

Sindelar, K., et al. Potential Antidepressants and Inhibitors of 5-Hydroxy-Tryptamine and Noradrenaline Re-uptake in the Brain: N,N-Dimethyl-(Arylthio)Thenylamines and N,N-Dimethyl-2-(Thienylthio)Benzylamines. Collect. Czech. Chem. Commun. 1991. 56:449-458.

Sejberg, J. Synth[e]sis of 3- and 2-phenylsulfany1-1H-indole [thesis] (English Translation). Lyngby (Denmark): Technical University of Denmark; Jan. 21, 2003. 102 pages (Tables 6, 7 and 8 are attached at the end of the document). Available from: Technical University of Denmark, Lyngby, DK; d991811.

Abstract and STN Search Report cited in the Jul. 10, 2008 Office Action in connection with parallel U.S. Appl. No. 11/452,823.

A. Burger, "Isosterism and Bioisosterism in drug design". Prog. Drug Res. 1991, 37:287-371.

Mitra, et al.; "Thiophenes & Thiapyrans: Part XVII—Thieno-(2:3-b)-thionaphthene & Thionaphtheno-(2:3-b)-thionaphthene", Journal of Scientific & Industrial Research., 1957, 16B:348-54.

us 7,652,150 B2

2-(1H-INDOLYLSULFANYL)-BENZYL AMINE DERIVATIVES AS SSRIS

Under 35 U.S.C. §120, this application is a continuation of U.S. Ser. No. 11/314,702, filed Dec. 21, 2005, which is §365 (c) continuation of PCT International Application No. PCT/DK2004/000894, filed Dec. 21, 2004, which claims the benefit of priority under 35 U.S.C. §119(e) of U.S. Provisional Application No. 60/532,593, filed Dec. 23, 2003, and under 35 U.S.C. §119(a)-(d), claims benefit of Danish Application No. PA200301923, filed Dec. 23, 2003. The entirety of each of the aforementioned application is hereby incorporated by reference.

FIELD OF THE INVENTION

The present invention relates to compounds which are serotonin reuptake inhibitors and preferably also norepinephrine reuptake inhibitors, and the medical use of such compounds, e.g. in the treatment of depression and anxiety, affective disorders, pain disorders, attention deficit hyperactivity disorder (ADHD) and stress urinary incontinence.

BACKGROUND OF THE INVENTION

The majority of currently available antidepressants can be classified in 3 classes:
 1) monoamine oxidase inhibitors (MAOIs),
 2) biogenic amine neurotransmitter [serotonin (5-HT), norepinephrine (NE) and dopamine (DA)] transporter reuptake blockers, and
 3) modulators, especially blockers of one or more of the 5-HT and/or NE receptors.

Since depression is associated with a relative deficiency of the biogenic amines, the use of 5-HT and/or NE-receptor blockers (i.e. 5-HT and or NE-antagonist's) have not proven very successful in the treatment of depression and anxiety and the preferred and currently most efficient treatments are based on the enhancement of 5-HT and/or NE neurotransmission by blocking their reuptake back from the synaptic cleft (Slattery, D. A. et al., "The evolution of antidepressant mechanisms", fundamental and Clinical pharmacology, 2004, 18, 1-21; Schloss, P. et al, "new insights into the mechanism of antidepressant therapy", Pharmacology and therapeutics, 2004, 102, 47-60).

For years monoamine reuptake inhibition has been studied for treatment of depression, i.e. in particular the monoamines serotonin (5-HT), norepinephrine (NE) and dopamine (DA).

Selective serotonin reuptake inhibitors (hereinafter referred to as SSRIs) have become first choice therapeutics in the treatment of depression, certain forms of anxiety and social phobias, because they generally are effective, well tolerated, and have a favourable safety profile compared to the classic tricyclic antidepressants. Drugs claimed to be SSRIs are for example fluoxetine, sertraline and paroxetine.

However, clinical studies on depression indicate that non-response to the known SSRIs is substantial, up to 30%. Another, often neglected, factor in antidepressant treatment is compliance, which has a rather profound effect on the patient's motivation to continue pharmacotherapy. First of all, there is generally a delay in therapeutic effect of the SSRIs. Sometimes symptoms even worsen during the first weeks of treatment. Secondly, sexual dysfunction is generally a side effect common to SSRIs. Without addressing these problems, real progress in the pharmacotherapy of depression and anxiety disorders is not likely to happen. Accordingly, there is a need for the development of compounds capable of improving the treatment of depression and other serotonin related diseases.

A newer strategy has been the development of dual reuptake inhibitors, e.g., the combined effect of serotonin reuptake inhibition and norepinephrine (norepinephrine is also named noradrenaline, NA) reuptake inhibition on depression is explored in clinical studies of compounds such as Duloxetine (Wong, "Duloxetine (LY-248686): an inhibitor of serotonin and noradrenaline uptake and an antidepressant drug candidate", Expert Opinion on Investigational Drugs, 1998, 7, 10, 1691-1699) and Venlafaxine (Khan-A et al, 30 "Venlafaxine in depressed outpatients", Psychopharmacology Bulletin, 1991, 27, 141-144). Compounds having such duel effect are also named SNRIs, "serotonin and noradrenaline reuptake inhibitors", or NSRIs, "noradrenaline and serotonin reuptake inhibitors".

Since treatment with the selective NE reuptake inhibitor reboxetine has been shown to stimulate 5-HT neurons and mediate the release of 5-HT in the brain (Svensson, T. et al, J. Neural. Transmission, 2004, 111, 127) there might be a synergistic advantage using SNRI's in the treatment of depression or anxiety.

The use of SNRI's have been shown in clinical studies to have a beneficial effect on pain (e.g. Fibromyalgia syndrome, overall pain, back pain, shoulder pain, headache, pain while awake and during daily activities) and especially pain associated with depression (Berk, M. Expert Rev. Neurotherapeutics 2003, 3, 47-451; Fishbain, D. A., et al. "Evidence-based data from animal and human experimental studies on pain relief with antidepressants: A structured review" Pain Medicine 2000 1:310-316).

SNRI's have also been shown in clinical studies to have a beneficial effect in attention deficit hyperactivity disorder (ADHD) (N. M. Mukaddes; Venlafaxine in attention deficit hyperactivity disorder, European Neuropsychopharmacology, Volume 12, Supplement 3, October 2002, Page 421).

Furthermore, SNRI's have been shown to be effective for the treatment of stress urinary incontinence (Dmochowski R. R. et al. "Duloxetine versus placebo for the treatment of North American women with stress urinary incontinence", Journal of Urology 2003, 170:4, 1259-1263.)

Furthermore, Axford L. et al. describe the development of triple 5-HT, NE and DA re-uptake inhibitors for treatment of depression. (2003, Bioorganic & Medical Chemistry Letters, 13, 3277-3280: "Bicyclo[2.2.1.]heptanes as novel triple reuptake inhibitors for the treatment of depression"). Wellbutrin (bupropion) which has DA re-uptake activity in vitro and in vivo, show antidepressant efficacy. Other combination studies have indicated that addition of some affininity at the DA uptake site may have some clinical benefit (Nelson, J. C. J. Clin. Psychiatry 1998, 59, 65; Masand, P. S. et al. Depression Anxiety 1998, 7, 89; Bodkin, J. A et al. J. Clin. Psychiatry 1997, 58, 137).

The present invention provides 2-(1H-indolylsulfanyl)-benzyl amine derivatives, formula I, which are serotonin reuptake inhibitors. In particular, the invention provides compounds possessing the combined effect of serotonin reuptake inhibition and norepinephrine reuptake inhibition. Furthermore, some of the compounds are also triple 5-HT, NE and DA re-uptake inhibitors.

Diphenyl sulphides of formula (XVI) and variations thereof have been disclosed as serotonin re-uptake inhibitors and have been suggested for use in treatment of depression, cf. e.g. U.S. Pat. No. 5,095,039, U.S. Pat. No. 4,056,632, EP 396827 A1 and WO 9312080. EP 402097 describes halogen substituted diphenylsulfides claimed to be selective serotonin inhibitors for treatment of depression. Likewise WO 9717325 discloses derivatives of N,N-dimethyl-2-(arylthio)benzylamine claimed to be selective serotonin transport inhibitors and suggest their use as antidepressants. J. Jilek et al., 1989, Collect. Czeck Chem. Commun., 54, 3294-3338 also discloses various derivatives of diphenyl sulphides, "phenylthio-benzylamines" as antidepressants. Furthermore, diphenyl sulphides are also disclosed in U.S. Pat. No. 3,803,143 and claimed useful as antidepressant.

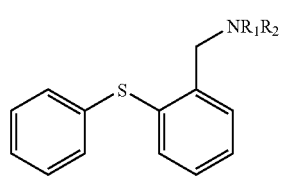

(XVI)

Several publications relates to the use of derivatives of diphenyl sulphides as "radiopharmaceuticals" for imaging SERT by SPECT or PET imaging, e.g. "S. Oya et al. J. Med. Chem. 2002, 45, 4716-4723" and "S. Oya et al. J. Med. Chem. 42, 3, 333-335". P. Emond et al (J. Med. Chem. (2002) 45, 1253-1258) and "S. Oya et al. (J. Med. Chem. 42, 3, 333-335) further test and discuss substituted "diphenyl sulfides" as selective serotonin tranporter ligands relative to dopamine and norepinephrine transporters (DAT, NET) with measurements of vitro affinities at the dopamine, serotonin, and norepinephrine transporters.

WO 0066537 also discloses certain derivatives of diphenyl sulphides claimed to be have higher selectivity for SERT over NET and DAT.

U.S. Pat. No. 4,018,830 and U.S. Pat. No. 4,055,665 discloses "phenylthioaralkylamines" and "2-phenylthiobenzylamines" represented structurally as "$Ar_1$—S—$Ar_2$ in which $Ar_1$ is a phenylakyl amine substituent and $Ar_2$ is a substituted or unsubstituted homocyclic or heterocyclic ring offrom 5-6 atoms, such as an aromatic ring, a heteroaromatic ring". The compounds are claimed to be useful for preventing "cardiac arrhythmias".

K. Sindelar et al., "Collection of Czechoslovak Chemical Communications, (1991), 56(2), 449-58, by K. Sindelar et al" disclose variations of compounds of formula (XVI) in which one of the rings is substituted with a thiophene ring with test for selectivity as 5-HT re-uptake inhibitor and NA re-uptake inhibitor, respectively, for use as antidepressants. U.S. Pat. No. 6,596,741 B2 and U.S. Pat. No. 6,436,938 B1 and U.S. Pat. No. 6,410,736 B1 disclose biaryl ether derivates (XVII) reported to inhibit reuptake of monoamines, e.g. serotonin, dopamine and/or norepinephrine.

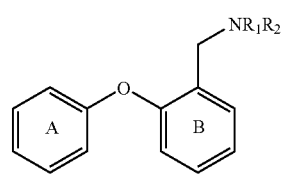

(XVII)

None of the above references disclose compounds comprising an indole group like the indolyl-sulfanyl benzyl amines of the present invention.

SUMMARY OF THE INVENTION

The present invention relates to a compound having the general formula I

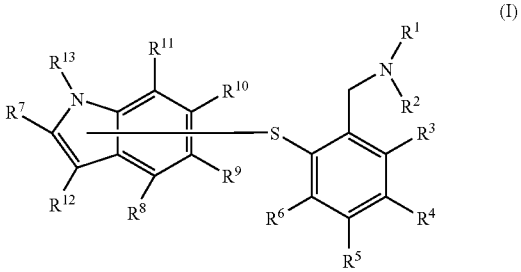

(I)

wherein the sulphur atom is attached to the indole via any ring carbon of the indole and wherein $R^1$-$R^{13}$ are as defined below; as the free base or a salt thereof.

In a further aspect the invention provides a compound of the above formula I according to the above as the free base or a pharmaceutical acceptable salt thereof for use as a medicament.

The invention also provides a pharmaceutical composition comprising a compound according to the above as the free base or a pharmaceutically acceptable salt thereof and at least one pharmaceutically acceptable carrier or diluent.

The invention further provides a method for the treatment of an affective disorder, such as depression, anxiety disorders including general anxiety disorder, social anxiety disorder, post traumatic stress disorder, obsessive compulsive disorder, panic disorder, panic attacks, specific phobias, social phobia or agoraphobia in a living animal body, including a human, comprising administering a therapeutically effective amount of a compound according to the above as the free base or a salt such as a pharmaceutically acceptable salt thereof. The invention furthermore concerns the use of a compound according to the above in a method of treatment of pain disorders, ADHD and stress urinary incontinence.

The invention further provides the use of a compound according to the above as the free base or a salt such as a pharmaceutically acceptable salt thereof for the preparation of a pharmaceutical composition for the treatment an affective disorder, such as depression, anxiety disorders including general anxiety disorder, social anxiety disorder, post traumatic stress disorder, obsessive compulsive disorder, panic disorder, panic attacks, specific phobias, social phobia or agoraphobia. The invention furthermore provides the use of a compound according to the above for the preparation of a pharmaceutical composition for the treatment of pain disorders, ADHD and stress urinary incontinence.

DETAILED DESCRIPTION OF THE INVENTION

Definitions

The term "halogen" means fluoro, chloro, bromo or iodo. "Halo" means halogen.

The expression "$C_{1-6}$-alk(en/yn)yl" means a $C_{1-6}$-alkyl, a $C_{2-6}$-alkenyl or a $C_{2-6}$-alkynyl group.

The term "$C_{1-6}$ alkyl" refers to a branched or unbranched alkyl group having from one to six carbon atoms inclusive, including but not limited to methyl, ethyl, 1-propyl, 2-propyl, 1-butyl, 2-butyl, 2-methyl-2-propyl and 2-methyl-1-propyl. Similarly, the term "$C_{1-4}$ alkyl" refers to a branched or unbranched alkyl group having from one to six carbon atoms inclusive, including but not limited to methyl, ethyl, 1-propyl, 2-propyl, 1-butyl, 2-butyl, 2-methyl-2-propyl and 2-methyl-1-propyl.

The term "$C_{2-6}$ alkenyl" designate such groups having from two to six carbon atoms, including one double bond, including but not limited to ethenyl, propenyl, and butenyl.

The term "$C_{2-6}$ alkynyl" designate such groups having from two to six carbon atoms, including one triple bond, including but not limited to ethynyl, propynyl and butynyl.

The expression "$C_{3-8}$-cycloalk(en)yl" means a $C_{3-8}$-cycloalkyl or a $C_{3-8}$-cycloalkenyl group. The term "$C_{3-8}$-cycloalkyl" designates a monocyclic or bicyclic carbocycle having three to eight C-atoms, including but not limited to cyclopropyl, cyclopentyl, and cyclohexyl. The term "$C_{3-8}$-cycloalkenyl" designates a monocyclic or bicyclic carbocycle having three to eight C-atoms and one double bond, including but not limited to cyclopropenyl, cyclopentenyl and cyclohexenyl.

In the expression "$C_{3-8}$-cycloalk(en)yl-$C_{1-6}$-alk(en/yn)yl", the terms "$C_{3-8}$-cycloalk(en)yl" and "$C_{1-6}$-alk(en/yn)yl" are as defined above.

The term "$C_{1-6}$-alk(en/yn)yloxy" refers to groups of the formula $C_{1-6}$-alk(en/yn)yl-O—, wherein $C_{1-6}$-alk(en/yn)yl are as defined above.

The terms "$C_{1-6}$-alk(en/yn)yl-carbonyl", "$C_{1-6}$-alk(en/yn)yl-aminocarbonyl" and "di-($C_{1-6}$-alk(en/yn)yl)aminocarbonyl" refers to groups of formula $C_{1-6}$-alk(en/yn)yl-CO—, $C_{1-6}$-alk(en/yn)yl-NH—CO— and ($C_{1-6}$-alk(en/yn)yl)$_2$-N—CO—, respectively, wherein $C_{1-6}$-alk(en/yn)yl are as defined above.

In the expressions "$C_{1-6}$-alk(en/yn)yl-amino", "di-($C_{1-6}$-alkyl)amino", "$C_{1-6}$-alk(en/yn)ylthio", "halo-$C_{1-6}$-alk(en/yn)yl", "halo-$C_{1-6}$-alk(en/yn)yl-sulfonyl", "halo-$C_{1-6}$-alk(en/yn)yl-sulfanyl", "$C_{1-6}$-alk(en/yn)ylsulfonyl", and "$C_{1-6}$-alk(en/yn)ylsulfanyl" etc., the terms "$C_{1-6}$-alk(en/yn)yl" and "halo" are as defined above.

The expression "$R^1$ and $R^2$ together with the nitrogen form a 4-7 membered ring containing zero or one double bond, optionally said ring in addition to said nitrogen comprises one further heteroatom selected from nitrogen, oxygen and sulphur" refers to a heterocylic rings system of a total of 4, 5, 6 or 7 members, such as, e.g. azetidine, pyrrolidine, piperidine, piperazine, homopiperazine or morpholine. This rings system may be unsubstituted or it may comprise one or more substituents, such as, e.g. a maximum of one or two substituents, e.g. selected from the group consisting halogen, hydroxy, $C_{1-6}$-alkyl, $C_{1-6}$-alkoxy, $C_{1-6}$-alkylthio, alkylsulphonyl, trifluoromethyl, trifluoromethylsulfonyl, and $C_{1-6}$-alkylcarbonyl.

The atoms of the indole are numbered according to IUPAC Commission on Nomenclature of Organic Chemistry guidelines (Rigaudy, J.; Klesney, S. P. *Nomenclature of Organic Chemistry* Pergamon Press, (1979) ISBN 0080223699).

The term "treatment" as used herein in connection with a disease or disorders includes also prevention as the case may be.

Compounds of the Invention

The present invention relates to a compound having the general formua I

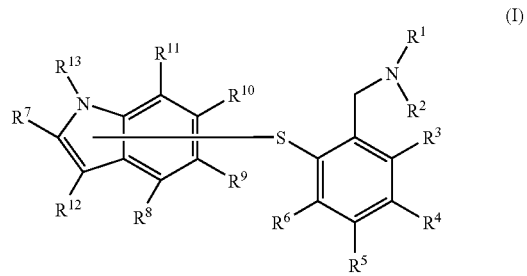

wherein the sulphur atom is attached to the indole via any ring carbon of the indole and wherein $R^1$-$R^2$ are independently selected from hydrogen, $C_{1-6}$-alk(en/yn)yl, $C_{3-8}$-cycloalk(en)yl, and $C_{3-8}$-cycloalk(en)yl-$C_{1-6}$-alk(en/yn)yl or $R^1$ and $R^2$ together with the nitrogen form a 4-7 membered ring containing zero or one double bond, optionally said ring in addition to said nitrogen comprises one further heteroatom selected from nitrogen, oxygen and sulphur;

$R^3$-$R^{12}$ are independently selected from hydrogen, halogen, cyano, nitro, $C_{1-6}$-alk(en/yn)yl, $C_{3-8}$-cycloalk(en)yl, $C_{3-8}$-cycloalk(en)yl-$C_{1-6}$-alk(en/yn)yl, amino, $C_{1-6}$-alk(en/yn)ylamino, di-($C_{1-6}$-alk(en/yn)yl)amino, $C_{1-6}$-alk(en/yn)ylcarbonyl, aminocarbonyl, $C_{1-6}$-alk(en/yn)ylaminocarbonyl, di-($C_{1-6}$-alk(en/yn)yl)aminocarbonyl, hydroxy, $C_{1-6}$-alk(en/yn)yloxy, $C_{1-6}$-alk(en/yn)ylthio, halo-$C_{1-6}$-alk(en/yn)yl, halo-$C_{1-6}$-alk(en/yn)ylsulfonyl, halo-$C_{1-6}$-alk(en/yn)ylsulfanyl and $C_{1-6}$-alk(en/yn)ylsulfonyl; and $R^{13}$ is selected from hydrogen, $C_{1-6}$-alk(en/yn)yl, $C_{3-8}$-cycloalk(en)yl and $C_{3-8}$-cycloalk(en)yl-$C_{1-6}$-alk(en/yn)yl;

as the free base or a salt thereof;

with the provisos that:

when the sulphur atom is attached via atom nr. 2 of the indole then $R^7$ does not exist;

when the sulphur atom is attached via atom nr. 3 of the indole then $R^{12}$ does not exist;

when the sulphur atom is attached via atom nr. 4 of the indole then $R^8$ does not exist;

when the sulphur atom is attached via atom nr. 5 of the indole then $R^9$ does not exist;

when the sulphur atom is attached via atom nr. 6 of the indole then $R^{10}$ does not exist; and when the sulphur atom is attached via atom nr. 7 of the indole then $R^{11}$ does not exist.

To further illustrate the invention, without limitation, the following embodiments of $R^1$-$R^2$ are within the scope of the invention, in particular for the compounds of the invention as the free base and the salts thereof:

$R^1$-$R^2$ are independently selected from hydrogen, $C_{1-6}$-alk(en/yn)yl, $C_{3-8}$-cycloalk(en)yl and $C_{3-8}$-cycloalk(en)yl-$C_{1-6}$-alk(en/yn)yl;

$R^1$-$R^2$ are independently selected from hydrogen and $C_{1-6}$-alkyl;

$R^1$-$R^2$ are independently selected from hydrogen and $C_{1-4}$-alkyl;

$R^1$ is hydrogen and $R^2$ is methyl;

$R^1$ and $R^2$ are methyl;

$R^1$ and $R^2$ are hydrogen.

To further illustrate the invention, without limitation, the following embodiments of $R^1$-$R^2$ are within the scope of the invention, in particular for the compounds of the invention as the free base and the salts thereof:

$R^1$-$R^2$ are independently selected from hydrogen and $C_{1-6}$-alk(en/yn)yl; or $R^1$ and $R^2$ together with the nitrogen form a 4-7 membered ring containing zero or one double bond, optionally the ring in addition to the nitrogen comprises one further heteroatom selected from nitrogen, oxygen and sulphur.

To further illustrate the invention, without limitation, the following embodiments of $R^1$-$R^2$ are also within the scope of the invention, in particular for the compounds of the invention as the free base and the salts thereof:

$R^1$ and $R^2$ together with the nitrogen form a 4-7, i.e. including 5 or 6, membered ring containing zero or one double bond, optionally said ring in addition to said nitrogen comprises one further heteroatom selected from nitrogen, oxygen and sulphur, which ring system is unsubstituted;

$R^1$ and $R^2$ together with the nitrogen form a 4-7, including 5 or 6, membered ring containing zero or one double bond, optionally said ring in addition to said nitrogen comprises one further heteroatom selected from nitrogen, oxygen and sulphur, which ring system comprises one or more substituents, such as, e.g. a maximum of one or two substituents, e.g. selected from the group consisting of hydroxy, $C_{1-6}$-alkyl (e.g. methyl), halogen (e.g. fluoro or chloro), $C_{1-6}$-alkoxy (e.g. methoxy), $C_{1-6}$-alkylthio, alkylsulphonyl, trifluoromethyl, trifluoromethylsulfonyl and $C_{1-6}$-alkylcarbonyl;

$R^1$ and $R^2$ together with the nitrogen form a ring selected from the group consisting of azetidine, pyrrolidine, piperidine, piperazine, homopiperazine or morpholine, which ring may be unsubstituted or it may comprise one or more substituents, such as, e.g. a maximum of one or two substituents, e.g. selected from the group consisting of hydroxy, $C_{1-6}$-alkyl (e.g. methyl), halogen (e.g. fluoro or chloro), $C_{1-6}$-alkoxy (e.g. methoxy), $C_{1-6}$-alkylthio, alkylsulphonyl, trifluoromethyl, trifluoromethylsulfonyl and $C_{1-6}$-alkylcarbonyl.

To further illustrate the invention, without limitation, the following embodiments of $R^3$-$R^{12}$ are within the scope of the invention, in particular for the compounds as the free base or salt thereof:

$R^3$-$R^{12}$ are independently selected from hydrogen, halogen, cyano, $C_{1-6}$-alkyl, $C_{3-8}$-cycloalkyl, $C_{3-8}$-cycloalkyl-$C_{1-6}$-alkyl, $C_{1-6}$-alkyloxy, $C_{1-4}$-alkylthio and trifluoromethyl;

$R^3$-$R^{12}$ are independently selected from hydrogen, chloro, fluoro, cyano, methyl, methoxy, methylthio and trifluoromethyl;

$R^3$-$R^{12}$ are hydrogen;

$R^3$-$R^2$ are independently selected from hydrogen and halogen;

$R^3$-$R^{12}$ are independently selected from hydrogen, chloro and fluoro;

$R^3$-$R^{12}$ are independently selected from hydrogen and chloro;

$R^3$-$R^{12}$ are independently selected from hydrogen and fluoro;

at least one of $R^3$-$R^{12}$ is fluoro or chloro;

$R^3$-$R^{12}$ are selected independently from hydrogen and cyano;

$R^3$-$R^{12}$ are selected independently from hydrogen and $C_{1-6}$-alk(en/yn)yl;

$R^3$-$R^{12}$ are selected independently from hydrogen and $C_{1-6}$-alkyl, such as methyl;

$R^3$-$R^{12}$ are selected independently from hydrogen and $C_{1-6}$-alk(en/yn)yloxy, preferably $C_{1-6}$-alkoxy, such as methoxy;

$R^3$-$R^{12}$ are selected independently from hydrogen and $C_{1-6}$-alkylthio, such as methylthio;

$R^3$-$R^{12}$ are selected independently from hydrogen and trifluoromethyl.

Within the invention, are embodiments where:

a limited number of $R^3$-$R^{12}$ are different from hydrogen, e.g. at least 3, or at least 5 or at least 6 of $R^3$-$R^{12}$ are hydrogen;

all of $R^3$-$R^{12}$ are hydrogen;

only 1, 2, 3 or 4 of $R^3$-$R^{12}$ is different from hydrogen.

In one embodiment of the invention only 1, 2 or 3 of $R^3$-$R^{12}$ are different from hydrogen, preferably selected independently from the group consisting of hydrogen, chloro, fluoro, cyano, methyl, methoxy, methylthio and trifluoromethyl.

To further illustrate the invention, without limitation, the following embodiments of $R^3$-$R^{12}$ are within the scope of the invention, in particular for the compounds as the free base or salt thereof:

$R^3$-$R^{12}$ are independently selected from hydrogen, halogen, cyano, $C_{1-6}$-alk(en/yn)yl, $C_{3-8}$-cycloalk(en)yl, $C_{3-8}$-cycloalk(en)yl-$C_{1-6}$-alk(en/yn)yl, hydroxy, $C_{1-6}$-alk(en/yn)yloxy and halo-$C_{1-6}$-alk(en/yn)yl;

$R^3$-$R^{12}$ are independently selected from hydrogen, halogen, cyano, $C_{1-6}$-alk(en/yn)yl, hydroxy, $C_{1-6}$-alk(en/yn)yloxy and halo-$C_{1-6}$-alk(en/yn)yl;

one of $R^3$-$R^{12}$ is halogen such as chloro or bromo or iodo or fluoro;

one of $R^3$-$R^{12}$ is cyano;

one of $R^3$-$R^{12}$ is $C_{1-6}$-alk(en/yn)yl, such as $C_{1-6}$-alkyl, e.g. methyl or ethyl;

one of $R^3$-$R^{12}$ is hydroxy;

one of $R^3$-$R^{12}$ is $C_{1-4}$-alk(en/yn)yloxy, such as $C_{1-6}$-alkyloxy, e.g. methoxy;

one of $R^3$-$R^{12}$ is halo-$C_{1-6}$-alk(en/yn)yl such as halo-$C_{1-6}$-alkyl, e.g. trifluoro-methyl.

Within the invention, are embodiments where:

one of $R^3$-$R^{12}$ is different from hydrogen;

two of $R^3$-$R^{12}$ are different from hydrogen;

three of $R^3$-$R^{12}$ are different from hydrogen;

four of $R^3$-$R^{12}$ are different from hydrogen.

To further illustrate the invention, without limitation, the following embodiments of $R^3$-$R^6$ are within the scope of the invention, in particular for the compounds as the free base or salt thereof:

$R^3$-$R^6$ are independently selected from hydrogen, halogen, cyano, nitro, $C_{1-6}$-alk(en/yn)yl, $C_{3-8}$-cycloalk(en)yl, $C_{3-8}$-cycloalk(en)yl-$C_{1-6}$-alk(en/yn)yl, amino, $C_{1-6}$-alk(en/yn)ylamino, di-($C_{1-6}$-alk(en/yn)yl)amino, $C_{1-6}$-alk(en/yn)ylcarbonyl, aminocarbonyl, $C_{1-6}$-alk(en/yn)ylaminocarbonyl, di-($C_{1-6}$-alk(en/yn)yl)aminocarbonyl, hydroxy, $C_{1-6}$-alk(en/yn)yloxy, $C_{1-6}$-alk(en/yn)ylthio, halo-$C_{1-6}$-alk(en/yn)yl, halo-$C_{1-6}$-alk(en/yn)ylsulfonyl, halo-$C_{1-6}$-alk(en/yn)ylsulfanyl and $C_{1-6}$-alk(en/yn)ylsulfonyl; $R^3$-$R^6$ are independently selected from hydrogen, halogen, cyano, $C_{1-6}$-alkyl, $C_{3-8}$-cycloalkyl, $C_{3-8}$-cycloalkyl-$C_{1-6}$-alkyl, amino, $C_{1-6}$-alkylamino, di-($C_{1-6}$-alkyl)amino, $C_{1-6}$-alkylcarbonyl, aminocarbonyl, $C_{1-6}$-alkylaminocarbonyl, di-($C_{1-6}$-alkylamino)carbonyl, hydroxy, $C_{1-6}$-alkoxy, $C_{1-6}$-alkylthio, halo-$C_{1-6}$-alkyl, halo-$C_{1-6}$-alkylsulfonyl, halo-$C_{1-6}$-alkylsulfanyl and $C_{1-6}$-alkylsulfonyl;

$R^3$-$R^6$ are independently selected from hydrogen, halogen, $C_{1-6}$-alkyloxy and $C_{1-6}$-alkyl;

$R^3$-$R^6$ are independently selected from hydrogen, halogen, methoxy and methyl;

$R^3$-$R^6$ are independently selected from hydrogen, fluoro, chloro, methoxy and methyl.

Within the invention, are embodiments where a limited number of $R^3$-$R^6$ are different from hydrogen, e.g.:
only one or two of $R^3$-$R^6$ is different from hydrogen;
three of $R^3$-$R^6$ are hydrogen and one of $R^3$-$R^6$ is halogen;
three of $R^3$-$R^6$ are hydrogen and one of $R^3$-$R^6$ is methyl;
$R^4$ is different from hydrogen;
$R^5$ is different from hydrogen;
$R^4$ is different from hydrogen, e.g. chloro, fluoro, methyl or methoxy, and the rest of $R^3$-$R^6$ is hydrogen;
$R^5$ is different from hydrogen, e.g. chloro, fluoro, methyl or methoxy, and the rest of $R^3$-$R^6$ is hydrogen;
only one of $R^3$-$R^6$ is different from hydrogen and is selected from the group consisting of fluoro, chloro, methyl and methoxy;
$R^3$-$R^6$ are hydrogen.

To further illustrate the invention, without limitation, the following embodiments of $R^3$-$R^6$ are within the scope of the invention, in particular for the compounds as the free base or salt thereof:
$R^3$-$R^6$ are independently selected from hydrogen, halogen, cyano, $C_{1-6}$-alk(en/yn)yl, $C_{3-8}$-cycloalk(en)yl and $C_{3-8}$-cycloalk(en)yl-$C_{1-6}$-alk(en/yn)yl;
$R^3$-$R^6$ are independently selected from hydrogen, halogen and $C_{1-6}$-alk(en/yn)yl;
$R^3$ is hydrogen;
$R^4$ is selected from hydrogen, halogen and $C_{1-6}$-alk(en/yn)yl;
$R^4$ is hydrogen;
$R^4$ is halogen such as chloro or fluoro;
$R^4$ is $C_{1-6}$-alk(en/yn)yl such as $C_{1-6}$-alkyl e.g. methyl;
$R^5$ is selected from hydrogen and halogen;
$R^5$ is hydrogen;
$R^5$ is halogen such as chloro;
$R^6$ is hydrogen.

To further illustrate the invention, without limitation, the following embodiments of $R^7$-$R^{12}$ are within the scope of the invention, in particular for the compounds as the free base or salt thereof:
$R^7$-$R^{12}$ are independently selected from hydrogen, halogen, cyano, nitro, $C_{1-6}$-alk(en/yn)yl, $C_{3-8}$-cycloalk(en)yl, $C_{3-8}$-cycloalk(en)yl-$C_{1-6}$-alk(en/yn)yl, amino, $C_{1-6}$-alk(en/yn)ylamino, di-($C_{1-6}$-alk(en/yn)yl)amino, $C_{1-6}$-alk(en/yn)ylcarbonyl, aminocarbonyl, $C_{1-6}$-alk(en/yn)ylaminocarbonyl, di-($C_{1-6}$-alk(en)yl)aminocarbonyl, hydroxy, $C_{1-6}$-alk(en/yn)yloxy, $C_{1-6}$-alk(en/yn)ylthio, halo-$C_{1-6}$-alk(en/yn)yl, halo-$C_{1-6}$-alk(en/yn)ylsulfonyl, halo-$C_{1-6}$-alk(en/yn)ylsulfanyl and $C_{1-6}$-alk(en/yn)ylsulfonyl.

Within the invention, are embodiments where a limited number of $R^7$-$R^{12}$ are different from hydrogen, e.g.:
only one or two of $R^7$-$R^{12}$ is different from hydrogen;
only one of $R^7$-$R^{12}$ is different from hydrogen and the substituent is selected from the group consisting of hydrogen, methyl, fluoro, chloro or methoxy;
only two of $R^7$-$R^{12}$ is different from hydrogen and the substituents are selected independently from the group consisting of hydrogen, methyl, fluoro, chloro or methoxy.

To further illustrate the invention, without limitation, the following embodiments of $R^7$-$R^{12}$ are within the scope of the invention, in particular for the compounds as the free base or salt thereof:
$R^7$-$R^{12}$ are independently selected from hydrogen, halogen, cyano, $C_{1-6}$-alk(en/yn)yl, $C_{3-8}$-cycloalk(en)yl, $C_{3-8}$-cycloalk(en)yl-$C_{1-6}$-alk(en/yn)yl, hydroxy, $C_{1-6}$-alk(en/yn)yloxy and halo-$C_{1-6}$-alk(en/yn)yl;
$R^7$-$R^{12}$ are independently selected from hydrogen, halogen, cyano, $C_{1-6}$-alk(en/yn)yl, hydroxy, $C_{1-6}$-alk(en/yn)yloxy and halo-$C_{1-6}$-alk(en/yn)yl;

$R^7$ is selected from hydrogen and $C_{1-6}$-alk(en/yn)yl;
$R^7$ is $C_{1-6}$-alk(en/yn)yl such as $C_{1-6}$-alkyl;
$R^8$ is selected from hydrogen, halogen, cyano, $C_{1-16}$-alk(en/yn)yl, hydroxy and $C_{1-6}$-alk(en/yn)yloxy;
$R^8$ is hydrogen;
$R^8$ is halogen such as fluoro, chloro or bromo;
$R^8$ is cyano;
$R^8$ is $C_{1-6}$-alk(en/yn)yl such as $C_{1-6}$-alkyl e.g. methyl;
$R^8$ is hydroxy;
$R^8$ is $C_{1-6}$-alk(en/yn)yloxy such as $C_{1-6}$-alkyloxy e.g. methoxy;
$R^9$ is selected from hydrogen, halogen, cyano, $C_{1-6}$-alk(en/yn)yl, hydroxy and $C_{1-6}$-alk(en/yn)yloxy;
$R^9$ is hydrogen;
$R^9$ is halogen such as fluoro, chloro, iodo or bromo;
$R^9$ is cyano;
$R^9$ is $C_{1-6}$-alk(en/yn)yl such as $C_{1-6}$-alkyl e.g. methyl;
$R^9$ is hydroxy;
$R^9$ is $C_{1-6}$-alk(en/yn)yloxy such as $C_{1-6}$-alkyloxy e.g. methoxy;
$R^{10}$ is selected from hydrogen, halogen, cyano, $C_{1-6}$-alk(en/yn)yl, hydroxy, $C_{1-6}$-alk(en/yn)yloxy and halo-$C_{1-6}$-alk(en/yn)yl;
$R^{10}$ is hydrogen;
$R^{10}$ is halogen such as fluoro, chloro or bromo;
$R^{10}$ is cyano;
$R^{10}$ is $C_{1-6}$-alk(en/yn)yl such as $C_{1-6}$-alkyl e.g. methyl;
$R^{10}$ is hydroxy;
$R^{10}$ is $C_{1-6}$-alk(en/yn)yloxy such as $C_{1-6}$-alkyloxy e.g. methoxy;
$R^{10}$ is halo-$C_{1-6}$-alk(en/yn)yl such as halo-$C_{1-6}$-alkyl e.g. trifluoro-methyl;
$R^{11}$ is selected from hydrogen, halogen, $C_{1-6}$-alk(en/yn)yl and $C_{1-6}$-alk(en/yn)yloxy;
$R^{11}$ is hydrogen;
$R^{11}$ is halogen such as fluoro or chloro;
$R^{11}$ is $C_{1-6}$-alk(en/yn)yl such as $C_{1-6}$-alkyl e.g. methyl or ethyl;
$R^{11}$ is $C_{1-6}$-alk(en/yn)yloxy such as $C_{1-6}$-alkyloxy e.g. methoxy;
$R^{12}$ is selected from hydrogen and $C_{1-6}$-alk(en/yn)yl;
$R^{12}$ is hydrogen;
$R^{12}$ is $C_{1-6}$-alk(en/yn)yl such as $C_{1-6}$-alkyl e.g. methyl.

To further illustrate the invention, without limitation, the following embodiments of $R^7$ are within the scope of the invention, in particular for the compounds as the free base or salt thereof:
$R^7$ is hydrogen;
$R^7$ is methyl.

To further illustrate the invention, without limitation, the following embodiments of $R^{13}$ is within the scope of the invention, in particular for the compounds as the free base or salt thereof:
$R^{13}$ is selected from hydrogen and $C_{1-6}$-alk(en/yn)yl;
$R^{13}$ is hydrogen;
$R^{13}$ is $C_{1-6}$-alk(en/yn)yl such as $C_{1-6}$-alkyl e.g. methyl.

The above embodiments relates to the compounds of the invention having formula I In particular, the present invention relates to a compound having the general formula I wherein the sulphur atom is attached to the indole as indicated in below formulas IA to IF:

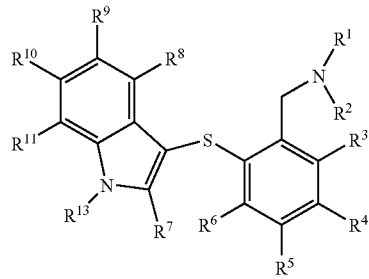
(IA)

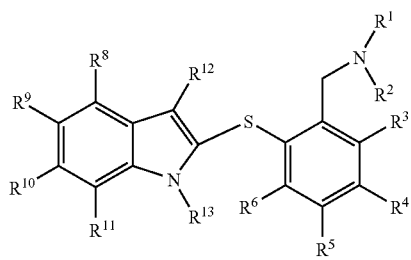
(IB)

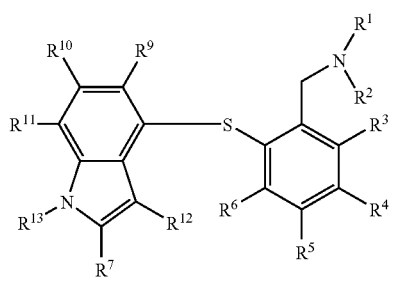
(IC)

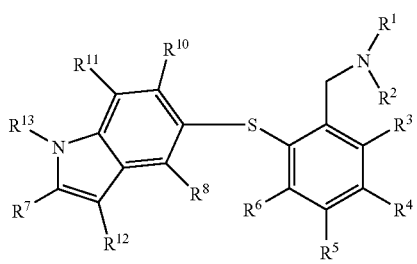
(ID)

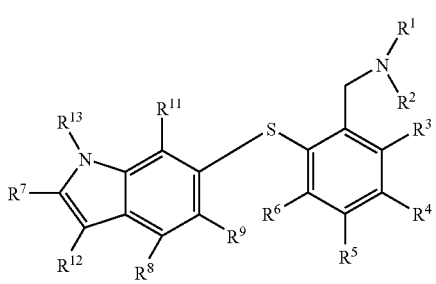
(IE)

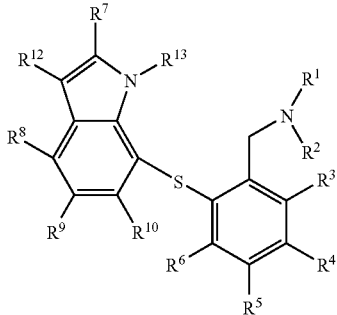
(IF)

and wherein $R^1$-$R^{13}$ are as defined herein, in particular wherein $R^1$-$R^2$ are independently selected from hydrogen, $C_{1-6}$-alk(en/yn)yl (e.g. methyl), $C_{3-8}$-cycloalk(en)yl, $C_{3-8}$-cycloalkyl-$C_{1-6}$-alkyl, or $R^1$ and $R^2$ together with the nitrogen form a 4-7 membered ring containing zero or one double bond, optionally the ring in addition to the nitrogen comprises one further heteroatom selected from nitrogen, oxygen and sulphur;

$R^3$-$R^{12}$ are independently selected from hydrogen, halogen (e.g. fluoro or chloro), cyano, nitro, $C_{1-6}$-alk(en/yn)yl (e.g. $C_{1-6}$-alkyl, such as methyl), $C_{3-8}$-cycloalk(en)yl (e.g. $C_{3-8}$-cycloalkyl), $C_{3-8}$-cycloalk(en)yl-$C_{1-6}$-alk(en/yn)yl (e.g. $C_{3-8}$-cycloalkyl-$C_{1-6}$-alkyl), amino, $C_{1-6}$-alk(en/yn)ylamino (e.g. $C_{1-6}$-alkylamino), di-($C_{1-6}$-alk(en/yn)yl)amino (e.g. di-($C_{1-6}$-alkyl)amino), $C_{1-6}$-alk(en/yn)ylcarbonyl (e.g. $C_{1-6}$-alkylcarbonyl), aminocarbonyl, $C_{1-6}$-alk(en/yn)ylaminocarbonyl (e.g. $C_{1-6}$-alkylaminocarbonyl), di-($C_{1-6}$-alk(en)yl)aminocarbonyl (e.g. di-($C_{1-6}$-alkyl)aminocarbonyl)), hydroxy, $C_{1-6}$-alk(en/yn)yloxy (e.g. $C_{1-6}$-alkoxy; such as methoxy), $C_{1-6}$-alk(en/yn)ylthio (e.g. $C_{1-6}$-alkylthio, such as methylthio), halo-$C_{1-6}$-alk(en/yn)yl (e.g., halo-$C_{1-6}$-alkyl, such as trifluoromethyl), halo-$C_{1-6}$-alk(en/yn)ylsulfonyl (e.g. trifluoromethylsulfonyl), halo-$C_{1-6}$-alk(en/yn)ylsulfanyl (e.g. trifluoromethylsulfanyl), and $C_{1-6}$-alk(en/yn)ylsulfonyl (e.g. $C_{1-6}$-alkylsulfonyl);

$R^{13}$ is selected from hydrogen, $C_{1-6}$-alk(en/yn)yl (e.g. $C_{1-6}$-alkyl, such as methyl), $C_{3-8}$-cycloalk(en)yl (e.g. $C_{3-8}$-cycloalkyl), and $C_{3-8}$-cycloalk(en)yl-$C_{1-6}$-alk(en/yn)yl (e.g. $C_{3-8}$-cycloalkyl-$C_{1-6}$-alkyl);

as the free base or a salt thereof.

A preferred embodiment relates to the compounds of the invention having formula IA. Any of the above embodiments are also embodiments of formula IA with the proviso that $R^{12}$ does not exist in compounds of general formula IA.

Another embodiment relates to the compounds of the invention which are not of formula IA.

A further embodiment relates to the compounds of the invention having formula IB. Any of the above embodiments are also embodiments of formula IB with the proviso that $R^7$ does not exist in compounds of general formula IB.

Another embodiment relates to the compounds of the invention which are not of formula IB.

A further embodiment relates to the compounds of the invention having formula IC. Any of the above embodiments are also embodiments of formula IC with the proviso that $R^8$ does not exist in compounds of general formula IC.

Another embodiment relates to the compounds of the invention which are not of formula IC.

A further embodiment relates to the compounds of the invention having formula ID. Any of the above embodiments are also embodiments of formula ID with the proviso that $R^9$ does not exist in compounds of general formula ID.

Another embodiment relates to the compounds of the invention which are not of formula ID.

A further embodiment relates to the compounds of the invention having formula IE. Any of the above embodiments are also embodiments of formula IE with the proviso that $R^{10}$ does not exist in compounds of general formula IE.

Another embodiment relates to the compounds of the invention which are not of formula IE.

A further embodiment relates to the compounds of the invention having formula IF. Any of the above embodiments are also embodiments of formula IF with the proviso that $R^{11}$ does not exist in compounds of general formula IF.

Another embodiment relates to the compounds of the invention which are not of formula IF.

To further illustrate the invention, without limitation, the following embodiments of formula IA are within the scope of the invention, in particular for the compounds as the free base or salt thereof: $R^8$-$R^{11}$ are independently selected from hydrogen, halogen, cyano, $C_{1-6}$-alkyl, $C_{3-8}$-cycloalkyl, $C_{3-8}$-cycloalkyl-$C_{1-6}$-alkyl, amino, $C_{1-6}$-alkylamino, di-($C_{1-6}$-alkyl)amino, $C_{1-6}$-alkylcarbonyl, aminocarbonyl, $C_{1-6}$-alkylaminocarbonyl, di-($C_{1-6}$-alkylamino)carbonyl, hydroxy, $C_{1-6}$-alkoxy, $C_{1-6}$-alkylthio, halo-$C_{1-6}$-alkyl, halo-$C_{1-6}$-alkylsulfonyl, halo-$C_{1-6}$-alkylsulfanyl, and $C_{1-6}$-alkylsulfonyl;

$R^8$-$R^{11}$ are independently selected from hydrogen, halogen, cyano, methyl, hydroxy, methoxy and trifluoromethyl;

$R^8$-$R^{11}$ are independently selected from hydrogen, halogen, methyl and methoxy;

$R^8$-$R^{11}$ are independently selected from hydrogen, fluoro, chloro, methyl and methoxy.

Within the invention, are embodiments where a limited number of $R^8$-$R^{11}$ are different from hydrogen, e.g.:

only one of $R^8$-$R^{11}$ is different from hydrogen and preferably selected from the group consisting of hydrogen, fluoro, chloro, methyl and methoxy, while rest of $R^8$-$R^{11}$ are hydrogen;

two of $R^{8-11}$ are different from hydrogen and preferably selected from the group consisting of hydrogen, fluoro, chloro, methyl and methoxy while and two of $R^{8-11}$ are hydrogen.

To further illustrate the invention, without limitation, the following embodiments of formula IA are within the scope of the invention, in particular for the compounds as the free base or salt thereof:

$R^8$ is selected from the group consisting of halogen (preferably fluoro or chloro), methyl and methoxy and $R^7$ and $R^{9-11}$ are hydrogen;

$R^9$ is selected from the group consisting of halogen (preferably fluoro or chloro), methyl and methoxy and $R^7$, $R^8$ and $R^{10-11}$ are hydrogen.

To further illustrate the invention, without limitation, the following embodiments of formula IA are within the scope of the invention, in particular for the compounds as the free base or salt thereof: only one of $R^{8-11}$ is different from hydrogen and is selected from the group consisting of halogen (e.g. fluoro or chloro), methyl, methoxy, hydroxy and cyano.

To further illustrate the invention, without limitation, the following embodiments of formula IA are within the scope of the invention, in particular for the compounds as the free base or salt thereof:

$R^8$ is hydroxy; $R^8$ is methoxy; $R^8$ is methyl; $R^8$ is cyano; $R^8$ is chloro; $R^8$ is fluoro; in a preferred embodiment, the rest of $R^8$ to $R^{11}$ are hydrogen.

To further illustrate the invention, without limitation, the following embodiments of formula IA are within the scope of the invention, in particular for the compounds as the free base or salt thereof:

$R^9$ is fluoro; $R^9$ is chloro; $R^9$ is bromo; $R^9$ is iodo; $R^9$ is methoxy; $R^9$ is methyl; $R^9$ is hydroxy; in a preferred embodiment, the rest of $R^8$ to $R^{11}$ are hydrogen.

To further illustrate the invention, without limitation, the following embodiments of formula IA are within the scope of the invention, in particular for the compounds as the free base or salt thereof:

$R^{10}$ is fluoro; $R^{10}$ is chloro; $R^{10}$ is bromo; $R^{10}$ is methyl; $R^{10}$ is cyano; $R^{10}$ is $CF_3$; $R^{10}$ is methoxy; in a preferred embodiment, the rest of $R^8$ to $R^{11}$ are hydrogen.

To further illustrate the invention, without limitation, the following embodiments of formula IA are within the scope of the invention, in particular for the compounds as the free base or salt thereof:

$R^{11}$ is methyl; $R^{11}$ is ethyl; $R^{11}$ is methoxy; $R^{11}$ is chloro; $R^{11}$ is fluoro; in a preferred embodiment, the rest of $R^8$ to $R^{11}$ are hydrogen.

To further illustrate the invention, without limitation, the following embodiments of formula IA are within the scope of the invention, in particular for the compounds as the free base or salt thereof: $R^{10}$ and $R^{11}$ are selected independently from the group consisting of hydrogen, methyl, fluoro and chloride.

To further illustrate the invention, without limitation, the following embodiments of $R^{13}$ are within the scope of the invention, in particular for the compounds as the free base or salt thereof:

$R^{13}$ is hydrogen;

$R^{13}$ is $C_{1-6}$-alkyl;

$R^{13}$ is $C_{1-4}$-alkyl;

$R^{13}$ is methyl.

One embodiment, relates to compounds of formula IA, wherein $R^{13}$ is hydrogen or a $C_{1-6}$-alkyl, e.g. a $C_{1-4}$-alkyl, such as methyl and where $R^1$-$R^{11}$ are as defined herein.

To further illustrate the invention, without limitation, the following embodiment are within the scope of the invention, in particular for the compounds as the free base or salt thereof: the compound has the formula IA where $R^1$ is hydrogen, $R^2$ is hydrogen or $C_{1-6}$-alkyl, preferably $C_{1-4}$-alkyl, such as methyl, $R^3$-$R^6$ are independently selected from hydrogen, methyl and halogen, e.g. chloro or fluoro, $R^7$ is hydrogen or methyl, $R^{8-11}$ are independently selected from hydrogen, methyl, methoxy and halogen, e.g. chloro or fluoro, and $R^{13}$ is hydrogen, and where at most one or two of $R^8$-$R^{11}$ are different from hydrogen and at most one or two of $R^3$-$R^6$ are different from hydrogen.

In a further embodiment, the compound according to the invention is selected from the following list:

| Compound no. | Compound name |
|---|---|
| 1 | [2-(1H-Indol-3-ylsulfanyl)benzyl] dimethyl amine |
| 2 | [2-(5-cyano-1H-indol-3-ylsulfanyl)benzyl] dimethyl amine |
| 3 | [2-(4-Fluoro-1H-indol-3-ylsulfanyl)benzyl] dimethyl amine |
| 4 | [2-(4-Chloro-1H-indol-3-ylsulfanyl)benzyl] dimethyl amine |
| 5 | [2-(5-Fluoro-1H-indol-3-ylsulfanyl)benzyl] dimethyl amine |
| 6 | [2-(5-Chloro-1H-indol-3-ylsulfanyl)benzyl] dimethyl amine |
| 7 | Dimethyl-[2-(7-methyl-1H-indol-3-ylsulfanyl)benzyl]-amine |
| 8 | [2-(7-Methoxy-1H-indol-3-ylsulfanyl)benzyl] dimethyl amine |
| 9 | [2-(5-Methoxy-1H-indol-3-ylsulfanyl)benzyl] dimethyl amine |
| 10 | [2-(6-Fluoro-1H-indol-3-ylsulfanyl)benzyl] dimethyl amine |
| 11 | [2-(6-Chloro-1H-indol-3-ylsulfanyl)benzyl] dimethyl amine |
| 12 | Dimethyl-[2-(2-methyl-1H-indol-3-ylsulfanyl)benzyl]-amine |
| 13 | Dimethyl-[2-(6-methyl-1H-indol-3-ylsulfanyl)benzyl]-amine |
| 14 | [2-(4-cyano-1H-indol-3-ylsulfanyl)benzyl] dimethyl amine |
| 15 | Dimethyl-[2-(1-methyl-1H-indol-3-ylsulfanyl)benzyl] amine |
| 16 | Dimethyl-[2-(4-methyl-1H-indol-3-ylsulfanyl)benzyl] amine |
| 17 | [2-(4-Hydroxy-1H-indol-3-ylsulfanyl)-benzyl]methyl amine |
| 18 | [2-(6-cyano-1H-indol-3-ylsulfanyl)benzyl] dimethyl amine |
| 19 | [2-(7-Chloro-1H-indol-3-ylsulfanyl)benzyl] dimethyl amine |
| 20 | [2-(6-Methoxy-1H-indol-3-ylsulfanyl)benzyl] dimethyl amine |
| 21 | [2-(4-Methoxy-1H-indol-3-ylsulfanyl)benzyl] dimethyl amine |
| 22 | [2-(1H-Indol-3-ylsulfanyl)benzyl]methyl amine |
| 23 | [2-(6-Fluoro-1H-indol-3-ylsulfanyl)benzyl]methyl amine |
| 24 | [2-(5-Fluoro-1H-indol-3-ylsulfanyl)benzyl]methyl amine |
| 25 | Methyl-[2-(4-methyl-1H-indol-3-ylsulfanyl)benzyl] amine |
| 26 | [2-(4-Chloro-1H-indol-3-ylsulfanyl)benzyl]methyl amine |
| 27 | Methyl-[2-(2-methyl-1H-indol-3-ylsulfanyl)benzyl] amine |
| 28 | [2-(5-Fluoro-2-methyl-1H-indol-3-ylsulfanyl)-benzyl]methyl amine |
| 29 | Methyl-[2-(5-methyl-1H-indol-3-ylsulfanyl)benzyl]amine |
| 30 | Methyl-[2-(7-methyl-1H-indol-3-ylsulfanyl)benzyl]amine |
| 31 | [2-(4-Fluoro-1H-indol-3-ylsulfanyl)benzyl]methyl amine |
| 32 | [2-(7-Ethyl-1H-indol-3-ylsulfanyl)benzyl]methyl amine |
| 33 | [2-(6-Methoxy-1H-indol-3-ylsulfanyl)benzyl]methyl amine |
| 34 | [2-(5-Chloro-1H-indol-3-ylsulfanyl)benzyl]methyl amine |
| 35 | [2-(6-Chloro-1H-indol-3-ylsulfanyl)benzyl]methyl amine |
| 36 | [2-(5-Methoxy-4-methyl-1H-indol-3-ylsulfanyl)-benzyl]methyl amine |
| 37 | [2-(5,6-Dimethoxy-1H-indol-3-ylsulfanyl)-benzyl]methyl amine |
| 38 | [2-(6-Bromo-1H-indol-3-ylsulfanyl)-benzyl]methyl amine |
| 39 | Methyl-[2-(6-methyl-1H-indol-3-ylsulfanyl)-benzyl] amine |
| 40 | [2-(4,7-Dimethoxy-1H-indol-3-ylsulfanyl)-benzyl]methyl amine |
| 41 | [2-(5-Methoxy-1H-indol-3-ylsulfanyl)benzyl]methyl amine |
| 42 | [2-(4-Methoxy-1H-indol-3-ylsulfanyl)benzyl]methyl amine |
| 43 | [2-(5-Bromo-1H-indol-3-ylsulfanyl)-benzyl]methyl amine |
| 44 | [2-(7-Methoxy-1H-indol-3-ylsulfanyl)benzyl]methyl amine |
| 45 | [5-Chloro-2-(1H-indol-3-ylsulfanyl)-benzyl]methyl amine |
| 46 | Methyl-[2-(6-trifluoromethyl-1H-indol-3-ylsulfanyl)-benzyl] amine |
| 47 | [2-(5-Hydroxy-1H-indol-3-ylsulfanyl)-benzyl]methyl amine |
| 48 | [2-(4-Bromo-1H-indol-3-ylsulfanyl)-benzyl]methyl amine |
| 49 | [2-(7-Chloro-1H-indol-3-ylsulfanyl)-benzyl]methyl amine |
| 50 | [2-(5-Iodo-1H-indol-3-ylsulfanyl)-benzyl]methyl amine |
| 51 | [2-(6-Cyano-1H-indol-3-ylsulfanyl)-benzyl]methyl amine |
| 52 | [2-(1H-Indol-3-ylsulfanyl)-5-methyl-benzyl]methyl amine |
| 53 | Methyl-[2-(3-methyl-1H-indol-2-ylsulfanyl)-benzyl] amine |
| 54 | [2-(5,6-Dimethoxy-1H-indol-3-ylsulfanyl)-5-fluoro-benzyl]-methyl-amine |
| 55 | [5-Fluoro-2-(3-methyl-1H-indol-2-ylsulfanyl)-benzyl]-methyl-amine |
| 56 | [5-Fluoro-2-(4-fluoro-1H-indol-3-ylsulfanyl)-benzyl]-methyl-amine |
| 57 | [2-(4-Chloro-1H-indol-3-ylsulfanyl)-5-fluoro-benzyl]-methyl-amine |
| 58 | [2-(7-Chloro-1H-indol-3-ylsulfanyl)-5-fluoro-benzyl]-methyl-amine |
| 59 | [5-Fluoro-2-(6-trifluoromethyl-1H-indol-3-ylsulfanyl)-benzyl]-methyl-amine |
| 60 | [5-Fluoro-2-(7-methoxy-1H-indol-3-ylsulfanyl)-benzyl]-methyl-amine |
| 61 | [2-(4-Bromo-1H-indol-3-ylsulfanyl)-5-fluoro-benzyl]-methyl-amine |
| 62 | 3-(4-Fluoro-2-methylaminomethyl-phenylsulfanyl)-2-methyl-1H-indol-4-ol |
| 63 | 3-(4-Fluoro-2-methylaminomethyl-phenylsulfanyl)-1H-indol-6-ol |
| 64 | [5-Fluoro-2-(5-fluoro-1H-indol-3-ylsulfanyl)-benzyl]-methyl-amine |
| 65 | [5-Fluoro-2-(4-methoxy-1H-indol-3-ylsulfanyl)-benzyl]-methyl-amine |
| 66 | [2-(6-Chloro-1H-indol-3-ylsulfanyl)-5-fluoro-benzyl]-methyl-amine |
| 67 | [2-(5-Chloro-1H-indol-3-ylsulfanyl)-5-fluoro-benzyl]-methyl-amine |
| 68 | [5-Fluoro-2-(6-methyl-1H-indol-3-ylsulfanyl)-benzyl]-methyl-amine |
| 69 | [5-Fluoro-2-(5-methoxy-4-methyl-1H-indol-3-ylsulfanyl)-benzyl]-methyl-amine |
| 70 | [2-(5-Bromo-1H-indol-3-ylsulfanyl)-5-fluoro-benzyl]-methyl-amine |
| 71 | [5-Fluoro-2-(5-methoxy-1H-indol-3-ylsulfanyl)-benzyl]-methyl-amine |
| 72 | [2-(6-Bromo-1H-indol-3-ylsulfanyl)-5-fluoro-benzyl]-methyl-amine |
| 73 | [5-Fluoro-2-(6-fluoro-1H-indol-3-ylsulfanyl)-benzyl]-methyl-amine |
| 74 | [5-Fluoro-2-(6-methoxy-1H-indol-3-ylsulfanyl)-benzyl]-methyl-amine |
| 75 | [5-Fluoro-2-(2-methyl-1H-indol-3-ylsulfanyl)-benzyl]-methyl-amine |
| 76 | [5-Fluoro-2-(5-methyl-1H-indol-3-ylsulfanyl)-benzyl]-methyl-amine |
| 77 | [5-Fluoro-2-(4-methyl-1H-indol-3-ylsulfanyl)-benzyl]-methyl-amine |

-continued

| Compound no. | Compound name |
| --- | --- |
| 78 | [5-Fluoro-2-(7-methyl-1H-indol-3-ylsulfanyl)-benzyl]-methyl-amine |
| 79 | [5-Fluoro-2-(1-methyl-1H-indol-3-ylsulfanyl)-benzyl]-methyl-amine |
| 80 | [5-Fluoro-2-(5-fluoro-2-methyl-1H-indol-3-ylsulfanyl)-benzyl]-methyl-amine |
| 81 | [5-Chloro-2-(5-fluoro-1H-indol-3-ylsulfanyl)-benzyl]-methyl-amine |
| 82 | [5-Chloro-2-(5-methoxy-1H-indol-3-ylsulfanyl)-benzyl]-methyl-amine |
| 83 | [5-Chloro-2-(7-methyl-1H-indol-3-ylsulfanyl)-benzyl]-methyl-amine |
| 84 | [5-Chloro-2-(1-methyl-1H-indol-3-ylsulfanyl)-benzyl]-methyl-amine |
| 85 | [5-Chloro-2-(4-methoxy-1H-indol-3-ylsulfanyl)-benzyl]-methyl-amine |
| 86 | [5-Chloro-2-(7-methoxy-1H-indol-3-ylsulfanyl)-benzyl]-methyl-amine |
| 87 | [5-Chloro-2-(6-fluoro-1H-indol-3-ylsulfanyl)-benzyl]-methyl-amine |
| 88 | [5-Chloro-2-(5-fluoro-2-methyl-1H-indol-3-ylsulfanyl)-benzyl]-methyl-amine |
| 89 | [2-(5-Fluoro-2-methyl-1H-indol-3-ylsulfanyl)-5-methyl-benzyl]-methyl-amine |
| 90 | Methyl-[5-methyl-2-(4-methyl-1H-indol-3-ylsulfanyl)-benzyl]-amine |
| 91 | [2-(7-Ethyl-1H-indol-3-ylsulfanyl)-5-methyl-benzyl]-methyl-amine |
| 92 | [2-(6-Methoxy-1H-indol-3-ylsulfanyl)-5-methyl-benzyl]-methyl-amine |
| 93 | Methyl-[5-methyl-2-(2-methyl-1H-indol-3-ylsulfanyl)-benzyl]-amine |
| 94 | [2-(4-Methoxy-1H-indol-3-ylsulfanyl)-5-methyl-benzyl]-methyl-amine |
| 95 | [2-(6-Bromo-1H-indol-3-ylsulfanyl)-5-methyl-benzyl]-methyl-amine |
| 96 | [2-(6-Fluoro-1H-indol-3-ylsulfanyl)-5-methyl-benzyl]-methyl-amine |
| 97 | [2-(4-Fluoro-1H-indol-3-ylsulfanyl)-5-methyl-benzyl]-methyl-amine |
| 98 | 3-(4-Methyl-2-methylaminomethyl-phenylsulfanyl)-1H-indol-6-ol |
| 99 | [5-Chloro-2-(5-methyl-1H-indol-3-ylsulfanyl)-benzyl]-methyl-amine |
| 100 | [2-(6-Chloro-1H-indol-3-ylsulfanyl)-5-methyl-benzyl]-methyl-amine |
| 101 | [2-(5-Chloro-1H-indol-3-ylsulfanyl)-5-methyl-benzyl]-methyl-amine |
| 102 | 5-Fluoro-3-(2-piperidin-1-ylmethyl-phenylsulfanyl)-1H-indole |
| 103 | 5-Fluoro-3-(2-morpholin-4-ylmethyl-phenylsulfanyl)-1H-indole |
| 104 | 5-Fluoro-3-(2-pyrrolidin-1-ylmethyl-phenylsulfanyl)-1H-indole |
| 105 | [4-Chloro-2-(6-methyl-1H-indol-3-ylsulfanyl)-benzyl]-methyl-amine |
| 106 | [4-Chloro-2-(2-methyl-1H-indol-3-ylsulfanyl)-benzyl]-methyl-amine |
| 107 | [4-Chloro-2-(5-methyl-1H-indol-3-ylsulfanyl)-benzyl]-methyl-amine |
| 108 | [4-Chloro-2-(7-methyl-1H-indol-3-ylsulfanyl)-benzyl]-methyl-amine |
| 109 | [4-Chloro-2-(4-methyl-1H-indol-3-ylsulfanyl)-benzyl]-methyl-amine |
| 110 | [4-Chloro-2-(5-fluoro-1H-indol-3-ylsulfanyl)-benzyl]-methyl-amine |
| 111 | [4-Chloro-2-(6-fluoro-1H-indol-3-ylsulfanyl)-benzyl]-methyl-amine |
| 112 | [4-Chloro-2-(4-fluoro-1H-indol-3-ylsulfanyl)-benzyl]-methyl-amine |
| 113 | [4-Chloro-2-(7-fluoro-1H-indol-3-ylsulfanyl)-benzyl]-methyl-amine |
| 114 | [4-Chloro-2-(7-ethyl-1H-indol-3-ylsulfanyl)-benzyl]-methyl-amine |
| 115 | [4-Chloro-2-(5-methoxy-4-methyl-1H-indol-3-ylsulfanyl)-benzyl]-methyl-amine |
| 116 | [4-Chloro-2-(5-methoxy-1H-indol-3-ylsulfanyl)-benzyl]-methyl-amine |
| 117 | [4-Chloro-2-(6-methoxy-1H-indol-3-ylsulfanyl)-benzyl]-methyl-amine |
| 118 | [4-Chloro-2-(7-methoxy-1H-indol-3-ylsulfanyl)-benzyl]-methyl-amine |
| 119 | [4-Chloro-2-(4-methoxy-1H-indol-3-ylsulfanyl)-benzyl]-methyl-amine |
| 120 | [4-Chloro-2-(5-chloro-1H-indol-3-ylsulfanyl)-benzyl]-methyl-amine |
| 121 | [4-Chloro-2-(6-chloro-1H-indol-3-ylsulfanyl)-benzyl]-methyl-amine |
| 122 | [4-Chloro-2-(4-chloro-1H-indol-3-ylsulfanyl)-benzyl]-methyl-amine |
| 123 | [4-Chloro-2-(7-chloro-1H-indol-3-ylsulfanyl)-benzyl]-methyl-amine |
| 124 | [4-Chloro-2-(1H-indol-3-ylsulfanyl)-benzyl]-methyl-amine |
| 125 | [4-Chloro-2-(1-methyl-1H-indol-3-ylsulfanyl)-benzyl]-methyl-amine |
| 126 | [4-Chloro-2-(3-methyl-1H-indol-2-ylsulfanyl)-benzyl]-methyl-amine |
| 127 | [4-Chloro-2-(5-fluoro-2-methyl-1H-indol-3-ylsulfanyl)-benzyl]-methyl-amine |
| 128 | 2-(5-Fluoro-1H-indol-3-ylsulfanyl)-benzylamine |
| 129 | [2-(5-Fluoro-4-methoxy-1H-indol-3-ylsulfanyl)-benzyl]-methyl-amine |
| 130 | [2-(4,5-Difluoro-1H-indol-3-ylsulfanyl)-benzyl]-methyl-amine |
| 131 | [2-(4,6-Difluoro-1H-indol-3-ylsulfanyl)-benzyl]-methyl-amine |
| 132 | 3-(2-Methylaminomethyl-phenylsulfanyl)-1H-indol-4-ol |
| 133 | 2-(6-Fluoro-1H-indol-3-ylsulfanyl)-benzylamine |
| 134 | [2-(5,6-Difluoro-1H-indol-3-ylsulfanyl)-benzyl]-methyl-amine |
| 135 | 6-Fluoro-3-(2-methylaminomethyl-phenylsulfanyl)-1H-indol-5-ol |
| 136 | [2-(4-Chloro-1H-indol-3-ylsulfanyl)-5-methyl-benzyl]-methyl-amine |
| 137 | [2-(1H-Indol-5-ylsulfanyl)-benzyl]-methyl-amine |
| 138 | [2-(1H-Indol-4-ylsulfanyl)-benzyl]-methyl-amine |
| 139 | [2-(1H-Indol-6-ylsulfanyl)-benzyl]-methyl-amine |
| 140 | [2-(1H-Indol-7-ylsulfanyl)-benzyl]-methyl-amine | as the free base or a salt thereof, such as a pharmaceutically acceptable salt.

An non limiting aspect of the invention concerns such compounds according to the below embodiments 1-87:

1. A compound represented by the general formulas IA to IF:

(IA)

(IB)

(IC)

(ID)

(IE)

(IF)

Wherein

R$^1$-R$^2$ are independently selected from hydrogen, C$_{1-6}$-alk(en/yn)yl, C$_{3-8}$-cycloalk(en)yl, and C$_{3-8}$-cycloalk(en)yl-C$_{1-6}$-alk(en/yn)yl; or R$^1$ and R$^2$ together with the nitrogen form a 4-7 membered ring containing zero or one double bond, optionally said ring in addition to said nitrogen comprises one further heteroatom selected from nitrogen, oxygen and sulphur;

R$^3$-R$^{12}$ are independently selected from hydrogen, halogen, cyano, nitro, C$_{1-6}$-alk(en/yn)yl, C$_{3-8}$-cycloalk(en)yl, C$_{3-8}$-cycloalk(en)yl-C$_{1-6}$-alk(en/yn)yl, amino, C$_{1-6}$-alk(en/yn)ylamino, di-(C$_{1-6}$-alk(en/yn)yl)amino, C$_{1-6}$-alk(en/yn)ylcarbonyl, aminocarbonyl, C$_{1-6}$-alk(en/yn)ylaminocarbonyl, di-(C$_{1-6}$-alk(en)yl)aminocarbonyl, hydroxy, C$_{1-6}$-alk(en/yn)yloxy, C$_{1-6}$-alk(en/yn)ylthio, halo-C$_{1-6}$-alk(en/yn)yl, halo-C$_{1-6}$-alk(en/yn)ylsulfonyl, halo-C$_{1-6}$-alk(en/yn)ylsulfanyl, and C$_{1-6}$-alk(en/yn)ylsulfonyl; and R$^{13}$ is selected from hydrogen, C$_{1-6}$-alk(en/yn)yl, C$_{3-8}$-cycloalk(en)yl, and C$_{3-8}$-cycloalk(en)yl-C$_{1-6}$-alk(en/yn)yl; or a salt thereof.

2. The compound of embodiment 1, wherein R$^1$-R$^2$ are independently selected from hydrogen, C$_{1-6}$-alk(en/yn)yl, C$_{3-8}$-cycloalk(en)yl, and C$_{3-8}$-cycloalk(en)yl-C$_{1-6}$-alk(en/yn)yl; or a salt thereof.

3. The compound of embodiment 1, wherein R$^1$-R$^2$ are independently selected from hydrogen and C$_{1-6}$-alkyl; or a salt thereof.

4. The compound of embodiment 1, wherein R$^1$ is hydrogen and R$^2$ is methyl; or a salt thereof.

5. The compound of embodiment 1, wherein R$^1$ and R$^2$ are methyl; or a salt thereof.

6. The compound of embodiment 1, wherein R$^1$ and R$^2$ are hydrogen; or a salt thereof.

7. The compound of embodiment 1, wherein R$^1$ and R$^2$ together with the nitrogen form a 4-7 membered ring containing zero or one double bond, optionally said ring in addition to said nitrogen comprises one further heteroatom selected from nitrogen, oxygen and sulphur; or a salt thereof.

8. The compound of embodiment 1, wherein R$^1$ and R$^2$ together with the nitrogen form a ring selected from the group consisting of azetidine, pyrrolidine, piperidine, piperazine, homopiperazine or morpholine; or a salt thereof.

9. The compound of any of embodiments 1-8, wherein R$^3$-R$^{12}$ are independently selected from hydrogen, halogen, cyano, C$_{1-6}$-alkyl, C$_{3-8}$-cycloalkyl, C$_{3-8}$-cycloalkyl-C$_{1-6}$-alkyl, amino, C$_{1-6}$-alkylamino, di-(C$_{1-6}$-alkyl)amino, C$_{1-6}$-alkylcarbonyl, aminocarbonyl, C$_{1-6}$- alkylaminocarbonyl, di-($C_{1-6}$-alkylamino)carbonyl, hydroxy, $C_{1-6}$-alkoxy, $C_{1-6}$-alkylthio, halo-$C_{1-6}$-alkyl, halo-$C_{1-6}$-alkylsulfonyl, halo-$C_{1-6}$-alkylsulfanyl, and $C_{1-6}$-alkylsulfonyl; or a salt thereof.

10. The compound of any of embodiments 1-8, wherein $R^3$-$R^6$ are independently selected from hydrogen, halogen, cyano, nitro, $C_{1-6}$-alk(en/yn)yl, $C_{3-8}$-cycloalk(en)yl, $C_{3-8}$-cycloalk(en)yl-$C_{1-6}$-alk(en/yn)yl, amino, $C_{1-6}$-alk(en/yn)ylamino, di-($C_{1-6}$-alk(en/yn)yl)amino, $C_{1-6}$-alk(en/yn)ylcarbonyl, aminocarbonyl, $C_{1-6}$-alk(en/yn)ylaminocarbonyl, di-($C_{1-6}$-alk(en)yl)aminocarbonyl, hydroxy, $C_{1-6}$-alk(en/yn)yloxy, $C_{1-6}$-alk(en/yn)ylthio, halo-$C_{1-6}$-alk(en/yn)yl, halo-$C_{1-6}$-alk(en/yn)ylsulfonyl, halo-$C_{1-6}$-alk(en/yn)ylsulfanyl, and $C_{1-6}$-alk(en/yn)ylsulfonyl; or a salt thereof.

11. The compound of any of embodiments 1-8, wherein $R^3$-$R^6$ are independently selected from hydrogen, halogen, cyano, $C_{1-6}$-alkyl, $C_{3-8}$-cycloalkyl, $C_{3-8}$-cycloalkyl-$C_{1-6}$-alkyl, amino, $C_{1-6}$-alkylamino, di-($C_{1-6}$-alkyl)amino, $C_{1-6}$-alkylcarbonyl, aminocarbonyl, $C_{1-6}$-alkylaminocarbonyl, di-($C_{1-6}$-alkylamino)carbonyl, hydroxy, $C_{1-6}$-alkoxy, $C_{1-6}$-alkylthio, halo-$C_{1-6}$-alkyl, halo-$C_{1-6}$-alkylsulfonyl, halo-$C_{1-6}$-alkylsulfanyl, and $C_{1-6}$-alkylsulfonyl; or a salt thereof.

12. The compound of any of embodiments 1-8, wherein $R^3$-$R^6$ are independently selected from hydrogen, halogen, $C_{1-6}$-alkyloxy and $C_{1-6}$-alkyl; or a salt thereof.

13. The compound of any of embodiments 1-8, wherein $R^3$-$R^6$ are independently selected from hydrogen, halogen, methoxy and methyl; or a salt thereof.

14. The compound of any of embodiments 1-13, wherein only one or two of $R^3$-$R^6$ is different from hydrogen.

15. The compound of any of embodiments 1-13, wherein only one of $R^3$-$R^6$ is different from hydrogen; or a salt thereof.

16. The compound of any of embodiments 1-9, wherein three of $R^3$-$R^6$ are hydrogen and one of $R^3$-$R^6$ is halogen; or a salt thereof.

17. The compound of any of embodiments 1-9, wherein three of $R^3$-$R^6$ are hydrogen and one of $R^3$-$R^6$ is methyl; or a salt thereof.

18. The compound of any of embodiments 15-17, wherein $R^4$ is different from hydrogen; or a salt thereof.

19. The compound of any of embodiments 15-17, wherein $R^5$ is different from hydrogen; or a salt thereof.

20. The compound of any of embodiments 1-9, wherein $R^3$-$R^6$ are hydrogen; or a salt thereof.

21. The compound of any of embodiments 1-20, wherein $R^{13}$ is hydrogen; or a salt thereof.

22. The compound of any of embodiments 1-20, wherein $R^{13}$ is $C_{1-6}$-alkyl; or a salt thereof 23. The compound of any of embodiments 1-20, wherein $R^{13}$ is methyl; or a salt thereof.

24. The compound of any of embodiments 1-23, wherein the compound has the formula IA; or a salt thereof.

25. The compound of any of embodiments 1-23, wherein the compound has the formula IB; or a salt thereof.

26. The compound of any of embodiments 1-23, wherein the compound has the formula IC; or a salt thereof.

27. The compound of any of embodiments 1-23, wherein the compound has the formula ID; or a salt thereof.

28. The compound of any of embodiments 1-23, wherein the compound has the formula IE; or a salt thereof.

29. The compound of any of embodiments 1-23, wherein the compound has the formula IF, or a salt thereof.

30. The compound of any of embodiments 1-23, wherein the compound has the formula IA and $R^7$ is selected from the group consisting of hydrogen, halogen, cyano, nitro, $C_{1-6}$-alk(en/yn)yl, $C_{3-8}$-cycloalk(en)yl, $C_{3-8}$-cycloalk(en)yl-$C_{1-6}$-alk(en/yn)yl, amino, $C_{1-6}$-alk(en/yn)ylamino, di-($C_{1-6}$-alk(en/yn)yl)amino, $C_{1-6}$-alk(en/yn)ylcarbonyl, aminocarbonyl, $C_{1-6}$-alk(en/yn)ylaminocarbonyl, di-($C_{1-6}$-alk(en)yl)aminocarbonyl, hydroxy, $C_{1-6}$-alk(en/yn)yloxy, $C_{1-6}$-alk(en/yn)ylthio, halo-$C_{1-6}$-alk(en/yn)yl, halo-$C_{1-6}$-alk(en/yn)ylsulfonyl, halo-$C_{1-6}$-alk(en/yn)ylsulfanyl, and $C_{1-6}$-alk(en/yn)ylsulfonyl; or a salt thereof.

31. The compound of any of embodiments 1-23, wherein the compound has the formula IA and $R^7$ is selected from the group consisting of hydrogen, halogen, cyano, $C_{1-6}$-alkyl, $C_{3-8}$-cycloalkyl, $C_{3-8}$-cycloalkyl-$C_{1-6}$-alkyl, amino, $C_{1-6}$-alkylamino, di-($C_{1-6}$-alkyl)amino, $C_{1-6}$-alkylcarbonyl, aminocarbonyl, $C_{1-6}$-alkylaminocarbonyl, di-($C_{1-6}$-alkylamino)carbonyl, hydroxy, $C_{1-6}$-alkoxy, $C_{1-6}$-alkylthio, halo-$C_{1-6}$-alkyl, halo-$C_{1-6}$-alkylsulfonyl, halo-$C_6$-alkylsulfanyl, and $C_{1-6}$-alkylsulfonyl; or a salt thereof.

32. The compound of any of embodiments 1-23, wherein the compound has the formula IA and $R^7$ is hydrogen; or a salt thereof.

33. The compound of any of embodiments 1-23, wherein the compound has the formula IA and $R^7$ is methyl; or a salt thereof.

34. The compound of any of embodiments 1-23 or any of embodiments 30-33, wherein the compound has the formula IA and $R^8$-$R^{11}$ are independently selected from hydrogen, halogen, cyano, nitro, $C_{1-6}$-alk(en/yn)yl, $C_{3-8}$-cycloalk(en)yl, $C_{3-8}$-cycloalk(en)yl-$C_{1-6}$-alk(en/yn)yl, amino, $C_{1-6}$-alk(en/yn)ylamino, di-($C_{1-6}$-alk(en/yn)yl)amino, $C_{1-6}$-alk(en/yn)ylcarbonyl, aminocarbonyl, $C_{1-6}$-alk(en/yn)ylaminocarbonyl, di-($C_{1-6}$-alk(en)yl)aminocarbonyl, hydroxy, $C_{1-6}$-alk(en/yn)yloxy, $C_{1-6}$-alk(en/yn)ylthio, halo-$C_{1-6}$-alk(en/yn)yl, halo-$C_{1-6}$-alk(en/yn)ylsulfonyl, halo-$C_{1-6}$-alk(en/yn)ylsulfanyl, and $C_{1-6}$-alk(en/yn)ylsulfonyl; or a salt thereof.

35. The compound of any of embodiments 1-23 or any of embodiments 30-33, wherein the compound has the formula IA and $R^8$-$R^{11}$ are independently selected from hydrogen, halogen, cyano, $C_{1-6}$-alkyl, $C_{3-8}$-cycloalkyl, $C_{3-8}$-cycloalkyl-$C_{1-6}$-alkyl, amino, $C_{1-6}$-alkylamino, di-($C_{1-6}$-alkyl)amino, $C_{1-6}$-alkylcarbonyl, aminocarbonyl, $C_{1-6}$-alkylaminocarbonyl, di-($C_{1-6}$-alkylamino)carbonyl, hydroxy, $C_{1-6}$-alkoxy, $C_{1-6}$-alkylthio, halo-$C_{1-6}$-alkyl, halo-$C_{1-6}$-alkylsulfonyl, halo-$C_{1-6}$-alkylsulfanyl, and $C_{1-6}$-alkylsulfonyl; or a salt thereof.

36. The compound of any of embodiments 1-23 or any of embodiments 30-33, wherein the compound has the formula IA and $R^8$-$R^{11}$ are independently selected from hydrogen, halogen, cyano, methyl, hydroxy, methoxy and trifluoromethyl; or a salt thereof.

37. The compound of any of embodiments 1-23 or any of embodiments 30-33, wherein the compound has the formula IA and $R^8$-$R^{11}$ are independently selected from hydrogen, halogen, methyl and methoxy; or a salt thereof.

38. The compound of any of embodiments 34-36, wherein only one of $R^8$-$R^{11}$ is different from hydrogen while rest of $R^8$-$R^{11}$ are hydrogen; or a salt thereof.

39. The compound of any of embodiments 34-36, wherein the compound has the formula IA and two of $R^{8-11}$ are different from hydrogen and two of $R^{8-11}$ are hydrogen; or a salt thereof.

40. The compound of any one of embodiments 1-23 or 30-37, wherein the compound has the formula IA and $R^8$ is selected from the group consisting of halogen, methyl, and methoxy; or a salt thereof.
41. The compound of embodiments 40, wherein $R^{9-11}$ are hydrogen; or a salt thereof.
42. The compound of embodiments 41, wherein $R^7$ is hydrogen; or a salt thereof.
43. The compound of any one of embodiments 1-23 or 30-37, wherein the compound has the formula IA and $R^9$ is selected from the group consisting of halogen, methyl, and methoxy; or a salt thereof.
44. The compound of embodiments 43, wherein $R^8$ and $R^{10-11}$ are hydrogen; or a salt thereof.
45. The compound of embodiments 44, wherein $R^7$ is hydrogen; or a salt thereof.
46. The compound of any of embodiments 1-23 or 30-33, wherein the compound has the formula IA and wherein $R^{8-11}$ are hydrogen; or a salt thereof.
47. The compound of embodiments 38 or 39, wherein substituent(s) of $R^{8-11}$ being different from hydrogen is/are selected from the group consisting of halogen, methyl, methoxy, hydroxy, cyano; or a salt thereof.
48. The compound of embodiment 1, wherein the compound has the formula IA, and
$R^1$ is hydrogen and $R^2$ is hydrogen or a $C_{1-6}$-alkyl;
$R^3$-$R^6$ are independently selected from hydrogen, halogen and methyl, wherein at most one or two of $R^3$-$R^6$ are different from hydrogen;
$R^7$ is hydrogen or methyl
$R^{8-11}$ are independently selected from hydrogen, halogen, methyl, and methoxy wherein at most one or two of $R^8$-$R^{11}$ are different from hydrogen;
$R^{13}$ is hydrogen.
or a salt thereof.
49. The compound of embodiment 1 wherein the compound has the formula IA,
$R^1$ is hydrogen and $R^2$ is methyl;
$R^3$-$R^6$ are as defined in any one of claims 13-20;
$R^7$ is hydrogen
$R^8$-$R^{11}$ are as defined in claim 36-47
$R^{13}$ is hydrogen;
or a salt thereof.
50. The compound of any of embodiments 1-23 or any of embodiments 30-33, wherein the compound has the formula IA and $R^8$ is hydroxy; or a salt thereof.
51. The compound of any of embodiments 1-23 or any of embodiments 30-33, wherein the compound has the formula IA and $R^8$ is methoxy; or a salt thereof.
52. The compound of any of embodiments 1-23 or any of embodiments 30-33, wherein the compound has the formula IA and $R^8$ is methyl; or a salt thereof.
53. The compound of any of embodiments 1-23 or any of embodiments 30-33, wherein the compound has the formula IA and $R^8$ is cyano; or a salt thereof.
54. The compound of any of embodiments 1-23 or any of embodiments 30-33, wherein the compound has the formula IA and $R^8$ is Cl; or a salt thereof.
55. The compound of any of embodiments 1-23 or any of embodiments 30-33, wherein the compound has the formula IA and $R^8$ is F; or a salt thereof.
56. The compound of any of embodiments 1-23 or any of embodiments 30-33, wherein the compound has the formula IA and $R^9$ is cyano; or a salt thereof.
57. The compound of any of embodiments 1-23 or any of embodiments 30-33, wherein the compound has the formula IA and $R^9$ is F; or a salt thereof.
58. The compound of any of embodiments 1-23 or any of embodiments 30-33, wherein the compound has the formula IA and $R^9$ is Cl; or a salt thereof.
59. The compound of any of embodiments 1-23 or any of embodiments 30-33, wherein the compound has the formula IA and $R^9$ is Br; or a salt thereof.
60. The compound of any of embodiments 1-23 or any of embodiments 30-33, wherein the compound has the formula IA and $R^9$ is I; or a salt thereof.
61. The compound of any of embodiments 1-23 or any of embodiments 30-33, wherein the compound has the formula IA and $R^9$ is methoxy; or a salt thereof.
62. The compound of any of embodiments 1-23 or any of embodiments 30-33, wherein the compound has the formula IA and $R^9$ is methyl; or a salt thereof.
63. The compound of any of embodiments 1-23 or any of embodiments 30-33, wherein the compound has the formula IA and $R^9$ is hydroxy; or a salt thereof.
64. The compound of any of embodiments 1-23 or any of embodiments 30-33, wherein the compound has the formula IA and $R^{10}$ is F; or a salt thereof.
65. The compound of any of embodiments 1-23 or any of embodiments 30-33, wherein the compound has the formula IA and $R^{10}$ is Cl; or a salt thereof.
66. The compound of any of embodiments 1-23 or any of embodiments 30-33, wherein the compound has the formula IA and $R^{10}$ is Br; or a salt thereof.
67. The compound of any of embodiments 1-23 or any of embodiments 30-33, wherein the compound has the formula IA and $R^{10}$ is methyl; or a salt thereof.
68. The compound of any of embodiments 1-23 or any of embodiments 30-33, wherein the compound has the formula IA and $R^{10}$ is cyano; or a salt thereof.
69. The compound of any of embodiments 1-23 or any of embodiments 30-33, wherein the compound has the formula IA and $R^{10}$ is $CF_3$; or a salt thereof.
70. The compound of any of embodiments 1-23 or any of embodiments 30-33, wherein the compound has the formula IA and $R^{10}$ is methoxy; or a salt thereof.
71. The compound of any of embodiments 1-23 or any of embodiments 30-33, wherein the compound has the formula IA and $R^{11}$ is methyl; or a salt thereof.
72. The compound of any of embodiments 1-23 or any of embodiments 30-33, wherein the compound has the formula IA and $R^{11}$ is ethyl; or a salt thereof.
73. The compound of any of embodiments 1-23 or any of embodiments 30-33, wherein the compound has the formula IA and $R^{11}$ is methoxy; or a salt thereof.
74. The compound of any of embodiments 1-23 or any of embodiments 30-33, wherein the compound has the formula IA and $R^{11}$ is Cl; or a salt thereof.
75. The compound of any of embodiments 1-23 or any of embodiments 30-33, wherein the compound has the formula IA and $R^{11}$ is F; or a salt thereof.
76. The compound of any of embodiments 50-75, wherein the rest of $R^8$ to $R^{11}$ are hydrogen; or a salt thereof.
77. The compound of any of embodiments 1-23 or any of embodiments 30-33, wherein the compound has the formula IA and $R^{10}$ and $R^{11}$ are selected independently from the group consisting of hydrogen, methyl, fluoro and chloride; or a salt thereof.
78. The compound of embodiment 77, wherein at least one of $R^{10}$ and $R^{11}$ is hydrogen; or a salt thereof.
79. The compound of claim 1 selected from the group consisting of:
[2-(1H-Indol-3-ylsulfanyl)benzyl] dimethyl amine;
[2-(5-cyano-1H-indol-3-ylsulfanyl)benzyl] dimethyl amine

[2-(4-Fluoro-1H-indol-3-ylsulfanyl)benzyl] dimethyl amine
[2-(4-Chloro-1H-indol-3-ylsulfanyl)benzyl] dimethyl amine
[2-(5-Fluoro-1H-indol-3-ylsulfanyl)benzyl] dimethyl amine
[2-(5-Chloro-1H-indol-3-ylsulfanyl)benzyl] dimethyl amine
Dimethyl-[2-(7-methyl-1H-indol-3-ylsulfanyl)benzyl] amine
[2-(7-Methoxy-1H-indol-3-ylsulfanyl)benzyl] dimethyl amine
[2-(5-Methoxy-1H-indol-3-ylsulfanyl)benzyl] dimethyl amine
[2-(6-Fluoro-1H-indol-3-ylsulfanyl)benzyl] dimethyl amine
[2-(6-Chloro-1H-indol-3-ylsulfanyl)benzyl] dimethyl amine
Dimethyl-[2-(2-methyl-1H-indol-3-ylsulfanyl)benzyl] amine
Dimethyl-[2-(6-methyl-1H-indol-3-ylsulfanyl)benzyl] amine
[2-(4-cyano-1H-indol-3-ylsulfanyl)benzyl] dimethyl amine
Dimethyl-[2-(1-methyl-1H-indol-3-ylsulfanyl)benzyl] amine
Dimethyl-[2-(4-methyl-1H-indol-3-ylsulfanyl)benzyl] amine
Dimethyl-[2-(4-hydroxy-1H-indol-3-ylsulfanyl)benzyl] amine
[2-(6-cyano-1H-indol-3-ylsulfanyl)benzyl] dimethyl amine
[2-(7-Chloro-1H-indol-3-ylsulfanyl)benzyl] dimethyl amine
[2-(6-Methoxy-1H-indol-3-ylsulfanyl)benzyl] dimethyl amine
[2-(4-Methoxy-1H-indol-3-ylsulfanyl)benzyl] dimethyl amine
[2-(1H-Indol-3-ylsulfanyl)benzyl]methyl amine
[2-(6-Fluoro-1H-indol-3-ylsulfanyl)benzyl]methyl amine
[2-(5-Fluoro-1H-indol-3-ylsulfanyl)benzyl]methyl amine
Methyl-[2-(4-methyl-1H-indol-3-ylsulfanyl)benzyl] amine
[2-(4-Chloro-1H-indol-3-ylsulfanyl)benzyl]methyl amine
Methyl-[2-(2-methyl-1H-indol-3-ylsulfanyl)benzyl] amine
[2-(5-Fluoro-2-methyl-1H-indol-3-ylsulfanyl)-benzyl]methyl amine
Methyl-[2-(5-methyl-1H-indol-3-ylsulfanyl)benzyl] amine
Methyl-[2-(7-methyl-1H-indol-3-ylsulfanyl)benzyl] amine
[2-(4-Fluoro-1H-indol-3-ylsulfanyl)benzyl]methyl amine
[2-(7-Ethyl-1H-indol-3-ylsulfanyl)benzyl]methyl amine
[2-(6-Methoxy-1H-indol-3-ylsulfanyl)benzyl]methyl amine
[2-(5-Chloro-1H-indol-3-ylsulfanyl)benzyl]methyl amine
[2-(6-Chloro-1H-indol-3-ylsulfanyl)benzyl]methyl amine
[2-(5-Methoxy-4-methyl-1H-indol-3-ylsulfanyl)-benzyl] methyl amine
[2-(5,6-Dimethoxy-1H-indol-3-ylsulfanyl)-benzyl]methyl amine
[2-(6-Bromo-1H-indol-3-ylsulfanyl)-benzyl]methyl amine
Methyl-[2-(6-methyl-1H-indol-3-ylsulfanyl)-benzyl] amine
[2-(4,7-Dimethoxy-1H-indol-3-ylsulfanyl)-benzyl]methyl amine
[2-(5-Methoxy-1H-indol-3-ylsulfanyl)benzyl]methyl amine
[2-(4-Methoxy-1H-indol-3-ylsulfanyl)benzyl]methyl amine
[2-(5-Bromo-1H-indol-3-ylsulfanyl)-benzyl]methyl amine
[2-(7-Methoxy-1H-indol-3-ylsulfanyl)benzyl]methyl amine
[5-Chloro-2-(1H-indol-3-ylsulfanyl)-benzyl]methyl amine
Methyl-[2-(6-trifluoromethyl-1H-indol-3-ylsulfanyl)-benzyl] amine;
[5-Hydroxy-2-(1H-indol-3-ylsulfanyl)-benzyl]methyl amine;
[2-(4-Bromo-1H-indol-3-ylsulfanyl)-benzyl]methyl amine;
[2-(7-Chloro-1H-indol-3-ylsulfanyl)-benzyl]methyl amine;
[2-(5-Iodo-1H-indol-3-ylsulfanyl)-benzyl]methyl amine;
[2-(6-Cyano-1H-indol-3-ylsulfanyl)-benzyl]methyl amine;
[2-(1H-Indol-3-ylsulfanyl)-5-methyl-benzyl]methyl amine;
[2-(3-methyl-1H-indol-2-ylsulfanyl)-benzyl]methyl amine;
[2-(5,6-Dimethoxy-1H-indol-3-ylsulfanyl)-5-fluoro-benzyl]-methyl-amine;
[5-Fluoro-2-(3-methyl-1H-indol-2-ylsulfanyl)-benzyl]-methyl-amine;
[5-Fluoro-2-(4-fluoro-1H-indol-3-ylsulfanyl)-benzyl]-methyl-amine;
[2-(4-Chloro-1H-indol-3-ylsulfanyl)-5-fluoro-benzyl]-methyl-amine;
[2-(7-Chloro-1H-indol-3-ylsulfanyl)-5-fluoro-benzyl]-methyl-amine;
[5-Fluoro-2-(6-trifluoromethyl-1H-indol-3-ylsulfanyl)-benzyl]-methyl-amine;
[5-Fluoro-2-(7-methoxy-1H-indol-3-ylsulfanyl)-benzyl]-methyl-amine;
[2-(4-Bromo-1H-indol-3-ylsulfanyl)-5-fluoro-benzyl]-methyl-amine;
3-(4-Fluoro-2-methylaminomethyl-phenylsulfanyl)-2-methyl-1H-indol-4-ol;
3-(4-Fluoro-2-methylaminomethyl-phenylsulfanyl)-1H-indol-6-ol;
[5-Fluoro-2-(5-fluoro-1H-indol-3-ylsulfanyl)-benzyl]-methyl-amine;
[5-Fluoro-2-(4-methoxy-1H-indol-3-ylsulfanyl)-benzyl]-methyl-amine;
[2-(6-Chloro-1H-indol-3-ylsulfanyl)-5-fluoro-benzyl]-methyl-amine;
[2-(5-Chloro-1H-indol-3-ylsulfanyl)-5-fluoro-benzyl]-methyl-amine;
[5-Fluoro-2-(6-methyl-1H-indol-3-ylsulfanyl)-benzyl]-methyl-amine;
[5-Fluoro-2-(5-methoxy-4-methyl-1H-indol-3-ylsulfanyl)-benzyl]-methyl-amine;
[2-(5-Bromo-1H-indol-3-ylsulfanyl)-5-fluoro-benzyl]-methyl-amine;
[5-Fluoro-2-(5-methoxy-1H-indol-3-ylsulfanyl)-benzyl]-methyl-amine;
[2-(6-Bromo-1H-indol-3-ylsulfanyl)-5-fluoro-benzyl]-methyl-amine;
[5-Fluoro-2-(6-fluoro-1H-indol-3-ylsulfanyl)-benzyl]-methyl-amine;
[5-Fluoro-2-(6-methoxy-1H-indol-3-ylsulfanyl)-benzyl]-methyl-amine;
[5-Fluoro-2-(2-methyl-1H-indol-3-ylsulfanyl)-benzyl]-methyl-amine;
[5-Fluoro-2-(5-methyl-1H-indol-3-ylsulfanyl)-benzyl]-methyl-amine;
[5-Fluoro-2-(4-methyl-1H-indol-3-ylsulfanyl)-benzyl]-methyl-amine;
[5-Fluoro-2-(7-methyl-1H-indol-3-ylsulfanyl)-benzyl]-methyl-amine;
[5-Fluoro-2-(1-methyl-1H-indol-3-ylsulfanyl)-benzyl]-methyl-amine;
[5-Fluoro-2-(5-fluoro-2-methyl-1H-indol-3-ylsulfanyl)-benzyl]-methyl-amine;
[5-Chloro-2-(5-fluoro-1H-indol-3-ylsulfanyl)-benzyl]-methyl-amine;
[5-Chloro-2-(5-methoxy-1H-indol-3-ylsulfanyl)-benzyl]-methyl-amine;
[5-Chloro-2-(7-methyl-1H-indol-3-ylsulfanyl)-benzyl]-methyl-amine;
[5-Chloro-2-(1-methyl-1H-indol-3-ylsulfanyl)-benzyl]-methyl-amine;
[5-Chloro-2-(4-methoxy-1H-indol-3-ylsulfanyl)-benzyl]-methyl-amine;
[5-Chloro-2-(7-methoxy-1H-indol-3-ylsulfanyl)-benzyl]-methyl-amine;

[5-Chloro-2-(6-fluoro-1H-indol-3-ylsulfanyl)-benzyl]-methyl-amine;
[5-Chloro-2-(5-fluoro-2-methyl-1H-indol-3-ylsulfanyl)-benzyl]-methyl-amine;
[2-(5-Fluoro-2-methyl-1H-indol-3-ylsulfanyl)-5-methyl-benzyl]-methyl-amine;
Methyl-[5-methyl-2-(4-methyl-1H-indol-3-ylsulfanyl)-benzyl]-amine;
[2-(7-Ethyl-1H-indol-3-ylsulfanyl)-5-methyl-benzyl]-methyl-amine;
[2-(6-Methoxy-1H-indol-3-ylsulfanyl)-5-methyl-benzyl]-methyl-amine;
Methyl-[5-methyl-2-(2-methyl-1H-indol-3-ylsulfanyl)-benzyl]-amine;
[2-(4-Methoxy-1H-indol-3-ylsulfanyl)-5-methyl-benzyl]-methyl-amine;
[2-(6-Bromo-1H-indol-3-ylsulfanyl)-5-methyl-benzyl]-methyl-amine;
[2-(6-Fluoro-1H-indol-3-ylsulfanyl)-5-methyl-benzyl]-methyl-amine;
[2-(4-Fluoro-1H-indol-3-ylsulfanyl)-5-methyl-benzyl]-methyl-amine;
3-(4-Methyl-2-methylaminomethyl-phenylsulfanyl)-1H-indol-6-ol;
[5-Chloro-2-(5-methyl-1H-indol-3-ylsulfanyl)-benzyl]-methyl-amine;
[2-(6-Chloro-1H-indol-3-ylsulfanyl)-5-methyl-benzyl]-methyl-amine;
[2-(5-Chloro-1H-indol-3-ylsulfanyl)-5-methyl-benzyl]-methyl-amine;
5-Fluoro-3-(2-piperidin-1-ylmethyl-phenylsulfanyl)-1H-indole;
5-Fluoro-3-(2-morpholin-4-ylmethyl-phenylsulfanyl)-1H-indole;
5-Fluoro-3-(2-pyrrolidin-1-ylmethyl-phenylsulfanyl)-1H-indole;
[4-Chloro-2-(6-methyl-1H-indol-3-ylsulfanyl)-benzyl]-methyl-amine;
[4-Chloro-2-(2-methyl-1H-indol-3-ylsulfanyl)-benzyl]-methyl-amine;
[4-Chloro-2-(5-methyl-1H-indol-3-ylsulfanyl)-benzyl]-methyl-amine;
[4-Chloro-2-(7-methyl-1H-indol-3-ylsulfanyl)-benzyl]-methyl-amine;
[4-Chloro-2-(4-methyl-1H-indol-3-ylsulfanyl)-benzyl]-methyl-amine;
[4-Chloro-2-(5-fluoro-1H-indol-3-ylsulfanyl)-benzyl]-methyl-amine;
[4-Chloro-2-(6-fluoro-1H-indol-3-ylsulfanyl)-benzyl]-methyl-amine;
[4-Chloro-2-(4-fluoro-1H-indol-3-ylsulfanyl)-benzyl]-methyl-amine;
[4-Chloro-2-(7-fluoro-1H-indol-3-ylsulfanyl)-benzyl]-methyl-amine;
[4-Chloro-2-(7-ethyl-1H-indol-3-ylsulfanyl)-benzyl]-methyl-amine;
[4-Chloro-2-(5-methoxy-4-methyl-1H-indol-3-ylsulfanyl)-benzyl]-methyl-amine;
[4-Chloro-2-(5-methoxy-1H-indol-3-ylsulfanyl)-benzyl]-methyl-amine;
[4-Chloro-2-(6-methoxy-1H-indol-3-ylsulfanyl)-benzyl]-methyl-amine;
[4-Chloro-2-(7-methoxy-1H-indol-3-ylsulfanyl)-benzyl]-methyl-amine;
[4-Chloro-2-(4-methoxy-1H-indol-3-ylsulfanyl)-benzyl]-methyl-amine;
[4-Chloro-2-(5-chloro-1H-indol-3-ylsulfanyl)-benzyl]-methyl-amine;
[4-Chloro-2-(6-chloro-1H-indol-3-ylsulfanyl)-benzyl]-methyl-amine;
[4-Chloro-2-(4-chloro-1H-indol-3-ylsulfanyl)-benzyl]-methyl-amine;
[4-Chloro-2-(7-chloro-1H-indol-3-ylsulfanyl)-benzyl]-methyl-amine;
[4-Chloro-2-(1H-indol-3-ylsulfanyl)-benzyl]-methyl-amine;
[4-Chloro-2-(1-methyl-1H-indol-3-ylsulfanyl)-benzyl]-methyl-amine;
[4-Chloro-2-(3-methyl-1H-indol-2-ylsulfanyl)-benzyl]-methyl-amine;
[4-Chloro-2-(5-fluoro-2-methyl-1H-indol-3-ylsulfanyl)-benzyl]-methyl-amine;
2-(5-Fluoro-1H-indol-3-ylsulfanyl)-benzylamine;
[2-(5-Fluoro-4-methoxy-1H-indol-3-ylsulfanyl)-benzyl]-methyl-amine;
[2-(4,5-Difluoro-1H-indol-3-ylsulfanyl)-benzyl]-methyl-amine;
[2-(4,6-Difluoro-1H-indol-3-ylsulfanyl)-benzyl]-methyl-amine;
3-(2-Methylaminomethyl-phenylsulfanyl)-1H-indol-4-ol;
2-(6-Fluoro-1H-indol-3-ylsulfanyl)-benzylamine;
[2-(5,6-Difluoro-1H-indol-3-ylsulfanyl)-benzyl]-methyl-amine;
6-Fluoro-3-(2-methylaminomethyl-phenylsulfanyl)-1H-indol-5-ol; [2-(4-Chloro-1H-indol-3-ylsulfanyl)-5-methyl-benzyl]-methyl-amine;
[2-(1H-Indol-5-ylsulfanyl)-benzyl]-methyl-amine;
[2-(1H-Indol-4-ylsulfanyl)-benzyl]-methyl-amine;
[2-(1H-Indol-6-ylsulfanyl)-benzyl]-methyl-amine; and
[2-(1H-Indol-7-ylsulfanyl)-benzyl]-methyl-amine;
or a salt thereof.

80. The compound of any of embodiments 1-23, wherein the compound has the formula IB and $R^{12}$ is hydrogen or methyl; or a salt thereof.

81. A compound of any one of embodiments 1-80 or a pharmaceutically acceptable salt thereof for use in a medicament.

82. The use of a compound of any one of embodiments 1-80 or a pharmaceutically acceptable salt thereof for the preparation of a medicament for the treatment of affective disorders.

83. The use of a compound of any one of embodiments 1-80 or a pharmaceutically acceptable salt thereof for the preparation of a medicament for the treatment of depression, anxiety disorders including general anxiety disorder, social anxiety disorder, post traumatic stress disorder, obsessive compulsive disorder, panic disorder, panic attacks, specific phobias, social phobia or agoraphobia.

84. The use of a compound of any one of embodiments 1-80 or a pharmaceutically acceptable salt thereof for the preparation of a medicament for the treatment of depression.

85. A method for the treatment of an affective disorder comprising administering a therapeutically effective amount of a compound of any one of embodiments 1-80 or a pharmaceutically acceptable salt thereof.

86. A method for the treatment of depression, anxiety disorders including general anxiety disorder, social anxiety disorder, post traumatic stress disorder, obsessive compulsive disorder, panic disorder, panic attacks, specific phobias, social phobia or agoraphobia comprising administering a therapeutically effective amount of a compound of any one of embodiments 1-80 or a pharmaceutically acceptable salt thereof.

87. A pharmaceutical composition comprising a compound of any one of embodiments 1-80 or a pharmaceutically acceptable salt thereof.

The present invention comprises the free bases of the compounds of the invention. The present invention furthermore comprises salts of the compounds of the invention, typically, pharmaceutically acceptable salts. Such salts include pharmaceutical acceptable acid addition salts, pharmaceutically acceptable metal salts, ammonium and alkylated ammonium salts. Acid addition salts include salts of inorganic acids as well as organic acids.

Examples of suitable inorganic acids include hydrochloric, hydrobromic, hydroiodic, phosphoric, sulfuric, sulfamic, nitric acids and the like.

Examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like.

Also intended as pharmaceutical acceptable acid addition salts are the hydrates, which the present compounds, are able to form.

Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

The compounds of the present invention may have one or more asymmetric centres and it is intended that any optical isomers (i.e. enantiomers or diastereomers), as separated, pure or partially purified optical isomers and any mixtures thereof including racemic mixtures, i.e. a mixture of stereoisomeres, are included within the scope of the invention Racemic forms can be resolved into the optical antipodes by known methods, for example, by separation of diastereomeric salts thereof with an optically active acid, and liberating the optically active amine compound by treatment with a base. Another method for resolving racemates into the optical antipodes is based upon chromatography on an optically active matrix. Racemic compounds of the present invention can also be resolved into their optical antipodes, e.g. by fractional crystallization. The compounds of the present invention may also be resolved by the formation of diastereomeric derivatives. Additional methods for the resolution of optical isomers, known to those skilled in the art, may be used. Such methods include those discussed by J. Jaques, A. Collet and S. Wilen in "Enantiomers, Racemates, and Resolutions", John Wiley and Sons, New York (1981). Optically active compounds can also be prepared from optically active starting materials.

Furthermore, when a double bond or a fully or partially saturated ring system is present in the molecule geometric isomers may be formed. It is intended that any geometric isomers, as separated, pure or partially purified geometric isomers or mixtures thereof are included within the scope of the invention. Likewise, molecules having a bond with restricted rotation may form geometric isomers. These are also intended to be included within the scope of the present invention.

Furthermore, some of the compounds of the present invention may exist in different tautomeric forms and it is intended that any tautomeric forms that the compounds are able to form are included within the scope of the present invention.

The invention also encompasses prodrugs of the present compounds, which on administration undergo chemical conversion by metabolic processes before becoming pharmacologically active substances. In general, such prodrugs will be functional derivatives of the compounds of the general formula I, IA, IB, IC, IE or IF which are readily convertible in vivo into the required compound of the formula I, IA, IB, IC, IE or IF. Conventional procedures for the selection and preparation of suitable prodrug derivatives are described, for example, in "Design of Prodrugs", ed. H. Bundgaard, Elsevier, 1985.

The invention also encompasses active metabolites of the present compounds.

As described above the compounds of the invention, 2-(1H-indolylsulfanyl)-benzyl amine derivatives, are serotonin reuptake inhibitors.

Accordingly, one embodiment of invention relates to compounds of Formula I, IA, IB, IC, IE or IF (e.g. formula IA) as the free base or a salt thereof, wherein $R^1$-$R^{13}$ are as described herein, which compounds are serotonin reuptake inhibitors, i.e., e.g., having a binding affinity ($IC_{50}$) of 5 µM or less, typically of 1 µM or less, preferably less than 500 nM or less than 100 nM or less than 50 nM, preferably as measured by the method described in Example 9—Transporter binding assay.

One embodiment of invention relates to compounds of formula I, IA, IB, IC, IE or IF (e.g. formula IA) as the free base or salts thereof, wherein $R^1$-$R^{13}$ are as described herein, which compounds are norepinephrine reuptake inhibitors, i.e., e.g., having a binding affinity ($IC_{50}$) of 5 µM or less, typically of 1 µM or less, preferably less than 500 nM, less than 100 nM or less than 50 nM, preferably as measured by the method described in Example 9-Transporter binding assay.

A further embodiment of invention relates to compounds of formula I, IA, IB, IC, IE or IF (e.g. formula (IA)) as the free base or salts thereof, wherein $R^1$-$R^{13}$ are as described herein, which compounds are dopamine reuptake inhibitors, i.e., e.g., having a binding affinity ($IC_{50}$) of 5 µM or less, typically of 1 µM or less, preferably less than 500 nM, less than 100 nM or less than 50 nM, preferably as measured by the method described in Example 9-Transporter binding assay.

In particular, the invention provides compounds possessing the combined effect of serotonin reuptake inhibition and norepinephrine reuptake inhibition. Accordingly, a preferred embodiment relates to compounds of the invention (i.e. the compounds of formula I, IA, IB, IC, IE or IF (e.g. of formula IA) for which $R^1$-$R^{13}$ are as described herein) being dual serotonin and norepinephrine reuptake inhibitors, i.e. compounds of the invention which are both norepinephrine reuptake inhibitors and serotonin reuptake inhibitors, each of which are as defined above.

In one embodiment, it is preferred for the compounds of the invention possessing the combined effect of serotonin reuptake inhibition and norepineplrine reuptake inhibition as described above, that such compounds are not also dopamine reuptake inhibitors. Thus, this embodiment relates to compounds of the invention having a binding affinity for the serotonin transporter which is at least 5, preferably at least 10 or even more preferred at least 20 or 30 times higher than the binding affinity for the dopamine transporter, preferably as measured by the methods described in Example 9—Transporter binding assay.

In a further aspect the invention provides compounds possessing the combined effect of serotonin reuptake inhibition, norepinephrine and dopamine reuptake inhibition.

Accordingly, a preferred embodiment relates to compounds of the invention (i.e. the compounds of formula I, IA, IB, IC, IE or IF (e.g. formula IA) for which $R^1$-$R^{13}$ are as described herein) being triple serotonin, norepinephrine and dopamine reuptake inhibitors, i.e. compounds of the invention which are at the same time norepinephrine reuptake inhibitors, serotonin reuptake inhibitors, and dopamine reuptake inhibitors, each of which are as defined above.

Pharmaceutical Use

In a further aspect the invention provides a compound of formula I, IA, IB, IC, ID, IE or IF for use as a medicament.

As mentioned above the compounds of the invention are inhibitors of the serotonin transporter. In particular is provided compounds of the invention which are dual inhibitors of the serotonin and noradrenaline transporters. The compounds of the invention may thus be useful for treatment in a disorder or disease wherein the serotonin and/or noradrenaline are implicated.

Accordingly, in a further aspect the invention relates to a compound of the invention as the free base or a salt thereof for use as a medicament, i.e. in particular a compound represented by the general formula I, IA, IB, IC, IE or IF, e.g. formula IA, wherein $R^1$-$R^2$ are independently selected from hydrogen, $C_{1-6}$-alk(en/yn)yl, $C_{3-8}$-cycloalk(en)yl, and $C_{3-8}$-cycloalk(en)yl-$C_{1-6}$-alk(en/yn)yl; or $R^1$ and $R^2$ together with the nitrogen form a 4-7 membered ring containing zero or one double bond, optionally said ring in addition to said nitrogen comprises one further heteroatom selected from nitrogen, oxygen and sulphur; which ring structure is substituted or unsubstituted as described herein;

$R^3$-$R^{12}$ are independently selected from hydrogen, halogen, cyano, nitro, $C_{1-6}$-alk(en/yn)yl, $C_{3-8}$-cycloalk(en)yl, $C_{3-8}$-cycloalk(en)yl-$C_{1-6}$-alk(en/yn)yl, amino, $C_{1-6}$-alk(en/yn)ylamino, di-($C_{1-6}$-alk(en/yn)yl)amino, $C_{1-6}$-alk(en/yn)ylcarbonyl, aminocarbonyl, $C_{1-6}$-alk(en/yn)ylaminocarbonyl, di-($C_{1-6}$-alk(en)yl)aminocarbonyl, hydroxy, $C_{1-6}$-alk(en/yn)yloxy, $C_{1-6}$-alk(en/yn)ylthio, halo-$C_{1-6}$-alk(en/yn)yl, halo-$C_{1-6}$-alk(en/yn)ylsulfonyl, halo-$C_{1-6}$-alk(en/yn)ylsulfanyl, and $C_{1-6}$-alk(en/yn)ylsulfonyl; and $R^{13}$ is selected from hydrogen, $C_{1-6}$-alk(en/yn)yl, $C_{3-8}$-cycloalk(en)yl, and $C_{3-8}$-cycloalk(en)yl-$C_{1-6}$-alk(en/yn)yl;

as the free base or a salt thereof;

with the provisos that:

when the sulphur atom is attached via atom nr. 2 of the indole then $R^7$ does not exist;

when the sulphur atom is attached via atom nr. 3 of the indole then $R^{12}$ does not exist;

when the sulphur atom is attached via atom nr. 4 of the indole then $R^8$ does not exist;

when the sulphur atom is attached via atom nr. 5 of the indole then $R^9$ does not exist;

when the sulphur atom is attached via atom nr. 6 of the indole then $R^{10}$ does not exist; and when the sulphur atom is attached via atom nr. 7 of the indole then $R^{11}$ does not exist.

By the expression a compound of the invention is meant any one of the embodiments of formula I, IA, IB, IC, IE or IF, in particular formula IA described herein.

The present invention also relates to a pharmaceutical composition comprising a compound of the invention as the free base or a salt thereof and a pharmaceutically acceptable carrier or diluent.

In an embodiment of the pharmaceutical composition, the compound of the invention is present in an amount of from about 0.001 to about 100 mg/kg body weight per day.

The present invention also relates to use of a compound of the invention as the free base or a salt thereof for the preparation of a pharmaceutical composition for the treatment of a disease or disorder, wherein a serotonin reuptake inhibitor is beneficial. The medicament may comprise any one of the embodiments of formula I, IA, IB, IC, IE or IF described herein.

The present invention also relates to use of a compound of the invention as the free base or a salt thereof for the preparation of a pharmaceutical composition for the treatment of a disease or disorder, wherein the combined effect of serotonin reuptake inhibition and norepinephrine reuptake inhibition is beneficial. The medicament may comprise any one of the embodiments of formula I, IA, IB, IC, IE or IF described herein.

The present invention also relates to use of a compound of the invention as the free base or a salt thereof for the preparation of a pharmaceutical composition for the treatment of a disease or disorder, the combined effect of serotonin reuptake inhibition and norepinephrine and dopamine reuptake inhibition is beneficial. The medicament may comprise any one of the embodiments of formula I, IA, IB, IC, IE or IF described herein.

A further embodiment of the invention relates to the use of a compound of formula I, IA, IB, IC, ID, IE or IF for the preparation of a pharmaceutical composition for the treatment of affective disorders, pain disorders, ADHD and stress urinary incontinence.

In particular the invention also relates to use of a compound of the invention as the free base or a salt thereof for the preparation of a pharmaceutical composition for the treatment of affective disorders. To further illustrate without limiting the invention, the affective disorder to be treated is selected from the group consisting of depressive disorders and anxiety disorders.

A further embodiment concerns the use of a compound of formula I, IA, IB, IC, ID, IE or IF for the preparation of a pharmaceutical composition for the treatment of depressive disorders. Typically, the depressive disorder to be treated is selected from the group consisting of major depressive disorder, postnatal depression, dysthymia and depression associated with bipolar disorder, alzheimers, psychosis or parkinsons. To further illustrate without limiting the invention, an embodiment of the invention concerns the treatment of major depressive disorder; another embodiment concerns the treatment of postnatal depression; another embodiment concerns the treatment of dysthymia; another embodiment concerns the treatment of depression associated with bipolar disorder, alzheimers, psychosis or parkinsons. To further illustrate without limiting the invention, an embodiment of the invention concerns the treatment of depression associated with bipolar disorder; another embodiment concerns the treatment of depression associated with alzheimers; another embodiment concerns the treatment of depression associated with psychosis; another embodiment concerns the treatment of depression associated with parkinsons.

In a further embodiment the invention also relates to use of a compound of the invention as the free base or a salt thereof for the preparation of a pharmaceutical composition for the treatment of depression.

In a further embodiment the invention also relates to use of a compound of the invention as the free base or a salt thereof for the preparation of a pharmaceutical composition for the treatment of anxiety disorders. Typically, the anxiety disorders to be treated are selected from the group consisting of general anxiety disorder, social anxiety disorder, post traumatic stress disorder, obsessive compulsive disorder, panic disorder, panic attacks, specific phobias, social phobia and agoraphobia. In a further embodiment the invention also relates to use of a compound of the invention as the free base or a salt thereof for the preparation of a pharmaceutical composition for the treatment of general anxiety disorder. In a further embodiment the invention also relates to use of a compound of the invention as the free base or a salt thereof for the preparation of a pharmaceutical composition for the treatment of social anxiety disorder. In a further embodiment the invention also relates to use of a compound of the invention as the free base or a salt thereof for the preparation of a pharmaceutical composition for the treatment of post traumatic stress disorder. In a further embodiment the present invention also relates to use of a compound of the invention as the free base or a salt thereof the preparation of a pharmaceutical composition for the treatment of obsessive compulsive disorder. In a further embodiment the invention also relates to use of a compound of the invention as the free base or a salt thereof for the preparation of a pharmaceutical composition for the treatment of panic disorder. In a further embodiment present invention also relates to use of a compound of the invention as the free base or a salt thereof for the preparation of a pharmaceutical composition for the treatment of panic attacks. In a further embodiment the invention also relates to use of a compound of the invention as the free base or a salt thereof for the preparation of a pharmaceutical composition for the treatment of specific phobias. In a further embodiment the invention also relates to use of a compound of the invention as the free base or a salt thereof for the preparation of a pharmaceutical composition for the treatment of social phobia. In a further embodiment the invention also relates to use of a compound of the invention as the free base or a salt thereof for the preparation of a pharmaceutical composition for the treatment of agoraphobia.

A further aspect of the invention relates to a method for the treatment of a disease or disorder selected from the group consisting of an affective disorder, such as depression, anxiety disorders including general anxiety disorder, social anxiety disorder, post traumatic stress disorder, obsessive compulsive disorder, panic disorder, panic attacks, specific phobias, social phobia and agoraphobia in a living animal body, including a human, comprising administering to a subject in need thereof a therapeutically effective amount of a compound of the invention as the free base or a salt thereof, i.e. in particular a compound represented by the general formula I, IA, IB, IC, IE or IF, e.g. formula IA.

In a further embodiment the present invention relates to the use of a compound of formula I, IA, IB, IC, ID or IE as the free base or a salt thereof for the preparation of a pharmaceutical composition for the treatment of pain disorders. To further illustrate without limiting the invention, the pain disorder to be treated is selected from the group consisting of fibromyalgia syndrome (FMS), overall pain, back pain, shoulder pain, headache as well as pain while awake and during daily activities. To further illustrate without limiting the invention, an embodiment of the invention concerns the treatment of fibromyalgia syndrome; another embodiment concerns the treatment of overall pain; another embodiment concerns the treatment of back pain; another embodiment concerns the treatment of shoulder pain; another embodiment concerns the treatment of headache; another embodiment concerns the treatment of pain while awake and during daily activities.

In a further embodiment the present invention relates to the use of a compound of formula I, IA, IB, IC, ID or IE as the free base or a salt thereof for the preparation of a pharmaceutical composition for the treatment of attention deficit hyperactivity disorder.

In a further embodiment the present invention relates to the use of a compound of formula I, IA, IB, IC, ID or IE as the free base or a salt thereof for the preparation of a pharmaceutical composition for the treatment of stress urinary incontinence.

Pharmaceutical Composition

The compounds of the invention as the free base or the salt thereof may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19 Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings such as enteric coatings or they can be formulated so as to provide controlled release of the active ingredient such as sustained or prolonged release according to methods well known in the art.

Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, cremes, gels, inhalants, dermal patches, implants, etc.

In an embodiment of the pharmaceutical composition, the compound of the invention administered in an amount of from about 0.001 to about 100 mg/kg body weight per day.

Conveniently, the compounds of the invention are administered in a unit dosage form containing said compounds in an amount of about 0.01 to 100 mg. The total daily dose is usually in the range of about 0.05-500 mg.

A typical oral dosage is in the range of from about 0.001 to about 100 mg/kg body weight per day, preferably from about 0.01 to about 50 mg/kg body weight per day, administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain from 0.01 to about 1000 mg, preferably from about 0.05 to about 500 mg, and more preferred from about 0.5 mg to about 200 mg.

For parenteral routes such as intravenous, intrathecal, intramuscular and similar administration, typically doses are in the order of about half the dose employed for oral administration.

The compounds of this invention are generally utilized as the free substance or as a salt such as a pharmaceutically acceptable salt thereof. One example is an acid addition salt of a compound having the utility of a free base. When a compound of the invention contains a free base such salts are prepared in a conventional manner by treating a solution or suspension of a free base of the invention with a chemical equivalent of an acid such as a pharmaceutically acceptable acid. Representative examples are mentioned above.

For parenteral administration, solutions of the compound of the invention in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospho lipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the compound of the invention and the pharmaceutical acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tablette, e.g. placed in a hard gelatine capsule in powder or pellet form or e.g. in the form of a troche or lozenge. The amount of solid carrier may vary but will usually be from about 25 mg to about 1 g.

If a liquid carrier is used, the preparation may be in the form of a syrup, emulsion, soft gelatine capsule or sterile injectable liquid such as an aqueous or non-aqueous liquid suspension or solution.

The pharmaceutical formulations of the invention may be prepared by conventional methods in the art.

For example: Tablets may be prepared by mixing the active ingredient with ordinary adjuvants and/or diluents and subsequently compressing the mixture in a conventional tabletting machine. Examples of adjuvants or diluents comprise: Corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

Solutions for injections may be prepared by dissolving the active ingredient and possible additives in a part of the solvent for injection, preferably sterile water, adjusting the solution to the desired volume, sterilising the solution and filling it in suitable ampoules or vials. Any suitable additive conventionally used in the art may be added, such as tonicity agents, preservatives, antioxidants, etc.

In a further aspect the present invention relates to a method of preparing a compound of the invention as described in the following.

Methods of Preparation of the Compounds of the Invention

The compounds of the invention may be prepared as follows:

Method 1 (for compounds of formula IA) Alkylating an amine of formula III with an alkylating derivative of formula II:

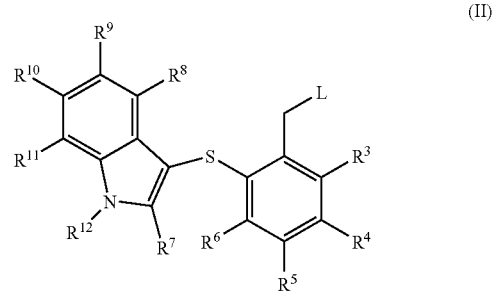

where $R^1$-$R^{13}$ are as defined herein, and L is a leaving group such as e.g. halogen, mesylate or tosylate;

whereupon the compound of formula IA is isolated as the free base or a salt such as a pharmaceutically acceptable acid addition salt thereof.

Method 2 (for compounds of formula IA) Reduction of an amide derivative of formula IV:

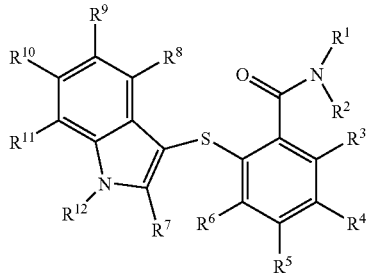

(IV)

where $R^1$-$R^{13}$ are as defined herein;

whereupon the compound of formula IA is isolated as the free base or a salt such as a pharmaceutically acceptable acid addition salt thereof.

Method 3 (for compounds of formula IA, also for compounds of formula IB when $R^{12}{\neq}$hydrogen) Reacting an indole of formula V with a reagent of formula VI by the use of a catalyst:

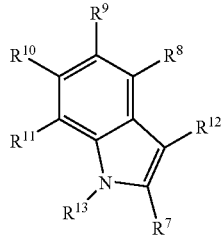

(V)

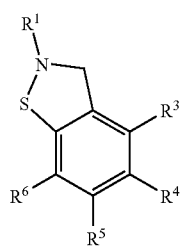

(VI)

where $R^1$-$R^{13}$ are as defined herein;

whereupon the compound of formula IA or the compound of formula IB when $R^{12}{\neq}$hydrogen is isolated as the free base or a salt such as a pharmaceutically acceptable acid addition salt thereof.

Method 4 (for compounds of formula IC) Reduction of an amide derivative of formula VII:

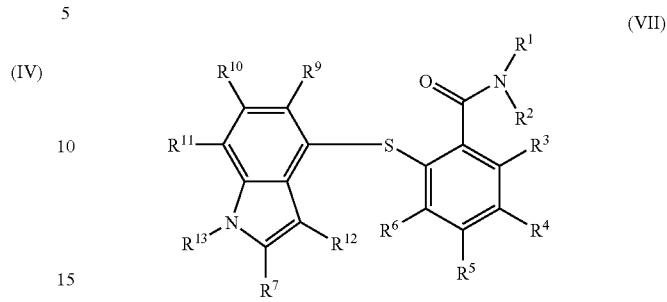

(VII)

where $R^1$-$R^{13}$ are as defined herein;

whereupon the compound of formula IC is isolated as the free base or a salt such as a pharmaceutically acceptable acid addition salt thereof.

Method 5 (for compounds of formula Id) Reduction of an amide derivative of formula VIII:

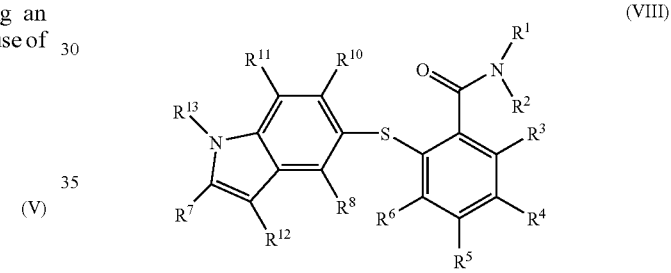

(VIII)

where $R^1$-$R^{13}$ are as defined herein;

whereupon the compound of formula ID is isolated as the free base or a salt such as a pharmaceutically acceptable acid addition salt thereof.

Method 6 (for compounds of formula IE) Reduction of an amide derivative of formula IX:

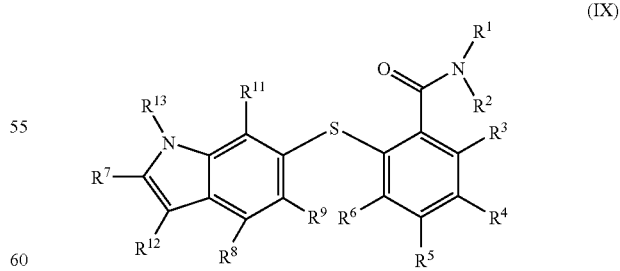

(IX)

where $R^1$-$R^{13}$ are as defined herein;

whereupon the compound of formula IE is isolated as the free base or a salt such as a pharmaceutically acceptable acid addition salt thereof.

Method 7 (for compounds of formula IF) Reduction of an amide derivative of formula X:

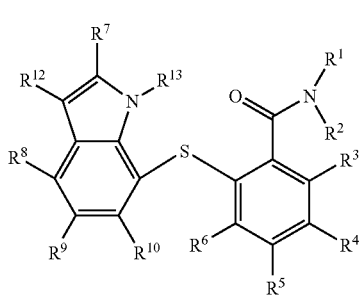

(X)

where $R^1$-$R^{13}$ are as defined herein;

whereupon the compound of formula IF is isolated as the free base or a salt such as a pharmaceutically acceptable acid addition salt thereof.

Method 8 (for compounds of formula IB with $R^{12}$=hydrogen) Reduction of an amide derivative of formula XI:

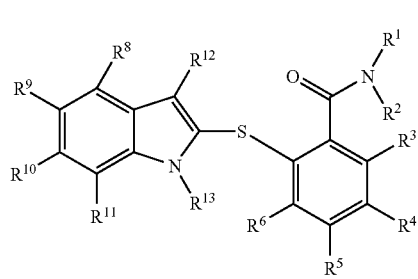

(XI)

where $R^1$-$R^{13}$ are as defined herein;

whereupon the compound of formula IB is isolated as the free base or a salt such as a pharmaceutically acceptable acid addition salt thereof.

Method 9 (for compounds of formula IC with $R^2$=hydrogen) Deprotection of a compound of formula XII:

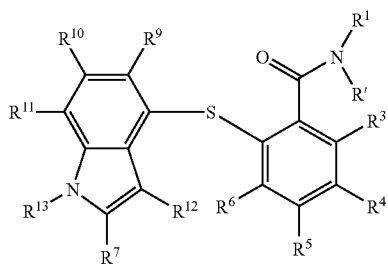

(XII)

where $R^1$, $R^3$-$R^{13}$ are as defined herein and R is a protection group such as a carbamate (such as methyl-, ethyl-, tert-butyl-, allyl-, or benzyl-carbamate);

whereupon the compound of formula IC is isolated as the free base or a salt such as a pharmaceutically acceptable acid addition salt thereof.

Method 10 (for compounds of formula ID with $R^2$=hydrogen) Deprotection of a compound of formula XIII:

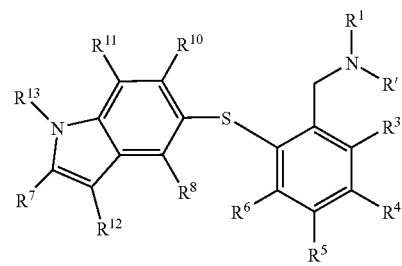

(XIII)

where $R^1$, $R^3$-$R^{13}$ are as defined herein and R is a protection group such as a carbamate (such as methyl-, ethyl-, tert-butyl-, allyl-, or benzyl-carbamate);

whereupon the compound of formula ID is isolated as the free base or a salt such as a pharmaceutically acceptable acid addition salt thereof.

Method 11 (for compounds of formula IE with $R^2$=hydrogen) Deprotection of a compound of formula XIV:

(XIV)

where $R^1$, $R^3$-$R^{13}$ are as defined herein and R is a protection group such as a carbamate (such as methyl-, ethyl-, tert-butyl-, allyl-, or benzyl-carbamate);

whereupon the compound of formula IE is isolated as the free base or a salt such as a pharmaceutically acceptable acid addition salt thereof.

Method 12 (for compounds of formula IF with $R^2$=hydrogen) Deprotection of a compound of formula XV:

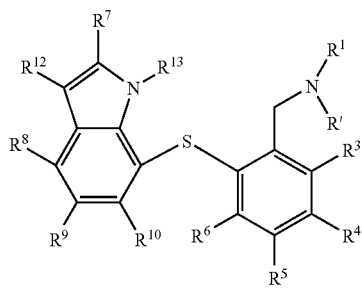

(XV)

where $R^1$, $R^3$-$R^{13}$ are as defined herein and R is a protection group such as a carbamate (such as methyl-, ethyl-, tert-butyl-, allyl-, or benzyl-carbamate);

whereupon the compound of formula IF is isolated as the free base or a salt such as a pharmaceutically acceptable acid addition salt thereof.

The alkylation according to method 1 is conveniently performed in an organic solvent such as a suitably boiling alcohol or ketone, preferably in the presence of an organic or inorganic base (potassium carbonate, diisopropylethylamine or triethylamine) at reflux temperature. Alternatively, the allylation can be performed at a fixed temperature, which is different from the boiling point, in one of the above-mentioned solvents or in dimethyl formamide (DMF), dimethylsulfoxide (DMSO), or N-methylpyrrolidin-2-one (NMP), preferably in the presence of a base. The alkylating derivatives of formula II can be derived from the corresponding benzylic alcohols which in turn are synthesised from the corresponding benzoic acids by standard reduction methods e.g. by the use of lithium aluminium hydride. The corresponding benzoic acids can be synthesised by methods analogous to those described in e.g. Hamel, P.; Girard, M.; Tsou, N. N.; *J. Heterocycl. Chem.;* 36, 1999, 643-652. The amines of formula III are commercially available.

The reduction according to method 2 is performed by standard literature methods i.e. by the use of a reducing agent like borane, alane or lithium aluminium hydride. Amides of the formula V can be prepared by coupling of the corresponding benzoic acids (synthesised by methods analogous to those described in e.g. Hamel, P.; Girard, M.; Tsou, N. N.; *J. Heterocycl. Chem.;* 36, 1999, 643-652 and Hamel, P.; Zajac, N.; Atkinson, J. G.; Girard, Y.; J. Org. Chem.; 59; 21; 1994; 6372-6377) with an amine of formula III by standard methods e.g. via the carboxylic acid chloride or activated esters or by the use of carboxylic acids in combination with a coupling reagent such as e.g. dicyclohexyl carbodiimide.

The reaction in method 3 can be performed by reacting a N-alkyl-2,3-dihydro-benzo[d]isothiazole of formula VI with an indole of formula V in the presence of an activating agent like e.g. an lewis acid or e.g. an oxidising agent like e.g. N-chlorosuccinimide. N-Alkyl-2,3-dihydro-benzo[d]isothiazoles of formula VI can be prepared by methods analogous to those described in the literature e.g. Hoffmann, R. W.; Goldmann, S.; *Chem. Ber.* 111, 1978, 2716-2725 and Kanakarajan, K.; Meier, H.; *Angew. Chem.* 96, 1984, 220. Indoles of formula V are either commercially available or can be prepared by standard methods as described in standard works like e.g. Houben-Weyl, Methoden der organischen Chemie (Methods of Organic Chemistry), Georg-Thieme-Verlag, Stuttgart and Organic Reactions, John Wiley & Sons, Inc. New York.

The reduction according to method 4 is performed by standard literature methods i.e. by the use of a reducing agent like borane, alane or lithium aluminium hydride. Amides of the formula VII can be prepared by coupling of the corresponding 2-mercapto-benzamides (synthesised by reduction of the corresponding 2,2'-dithiobenzamides analogous to those described in e.g. Elworthy, T. R.; Ford, A. P. D. W.; Bantle, G. W.; Morgans, D. J.; Ozer, R. S.; et al. *J. Med. Chem.* 40, 1997, 2674-2687) with a 4-halo- or 4-pseudohalo indole by methods analogous to those described in the literature e.g. Schopfer, U.; Schlapbach, A. *Tetrahedron;* 57, 2001, 3069-3073, where "halo" is either bromo or iodo or "pseudohalo" is e.g. triflate or nonaflate. When $R^{13}$=hydrogen in formula VII, then this position is protected prior to the coupling reaction and deprotected after the coupling reaction according to standard literature procedures with standard protection groups, e.g. a 4-methyl-phenyl-sulfonyl group or a tert-butoxy-carbonyl group.

The reduction according to method 5 is performed by standard literature methods i.e. by the use of a reducing agent like borane, alane or lithium aluminium hydride. Amides of the formula VIII can be prepared by coupling of the corresponding 2-mercapto-benzamides (synthesised by reduction of the corresponding 2,2'-dithiobenzamides analogous to those described in e.g. Elworthy, T. R.; Ford, A. P. D. W.; Bantle, G. W.; Morgans, D. J.; Ozer, R. S.; et al. *J. Med. Chem.* 40, 1997, 2674-2687) with a 5-halo- or 5-pseudohalo indole by methods analogous to those described in the literature e.g. Schopfer, U.; Schlapbach, A. *Tetrahedron;* 57, 2001, 3069-3073, where "halo" is either bromo or iodo or "pseudohalo" is e.g. triflate or nonaflate. When $R^{13}$=hydrogen in formula VIII, then this position is protected prior to the coupling reaction and deprotected after the coupling reaction according to standard literature procedures with standard protection groups, e.g. a 4-methyl-phenyl-sulfonyl group or a tert-butoxy-carbonyl group.

The reduction according to method 6 is performed by standard literature methods i.e. by the use of a reducing agent like borane, alane or lithium aluminium hydride. Amides of the formula IX can be prepared by coupling of the corresponding 2-mercapto-benzamides (synthesised by reduction of the corresponding 2,2'-dithiobenzamides analogous to those described in e.g. Elworthy, Todd R.; Ford, Anthony P. D. W.; Bantle, Gary W.; Morgans, David J.; Ozer, Rachel S.; et al. *J. Med. Chem.* 40, 1997, 2674-2687) with a 6-halo- or 6-pseudohalo indole by methods analogous to those described in the literature e.g. Schopfer, U.; Schlapbach, A. *Tetrahedron;* 57, 2001, 3069-3073, where "halo" is either bromo or iodo or "pseudohalo" is e.g. triflate or nonaflate. When $R^{13}$=hydrogen in formula IX, then this position is protected prior to the coupling reaction and deprotected after the coupling reaction according to standard literature procedures with standard protection groups, e.g. a 4-methyl-phenyl-sulfonyl group or a tert-butoxy-carbonyl group.

The reduction according to method 7 is performed by standard literature methods i.e. by the use of a reducing agent like borane, alane or lithium aluminum hydride. Amides of the formula X can be prepared by coupling of the corresponding 2-mercapto-benzamides (synthesised by reduction of the corresponding 2,2'-dithiobenzamides analogous to those described in e.g. Elworthy, T. R.; Ford, A. P. D. W.; Bantle, G. W.; Morgans, D. J.; Ozer, R. S.; et al. *J. Med. Chem.* 40, 1997, 2674-2687) with a 7-halo- or 7-pseudohalo indole by methods analogous to those described in the literature e.g. Schopfer, U.; Schlapbach, A. *Tetrahedron;* 57, 2001, 3069-3073, where "halo" is either bromo or iodo or "pseudohalo" is e.g. triflate or nonaflate. When $R^{13}$=hydrogen in formula X, then this position is protected prior to the coupling reaction and deprotected after the coupling reaction according to standard literature procedures with standard protection groups, e.g. a 4-methyl-phenyl-sulfonyl group or a tert-butoxy-carbonyl group.

The reduction according to method 8 is performed by standard literature methods i.e. by the use of a reducing agent like borane, alane or lithium aluminium hydride. Amides of the formula X can be prepared by acidic rearrangement (e.g. treatment in a solution of trifluoroacetic acid) of amides of formula IV analogous to methods described in the literature (Hamel, P.; Girard, M.; Tsou, N. N.; *J. Heterocyclic Chem.* 36, 1999, 643-652; Hamel, P.; Girard, Y.; Atkinson, J. G.; *J. Org. Chem.* 57, 1992; 2694-2699).

The deprotection according to method 9 can be performed by standard techniques, known to the persons skilled in the art and detailed in the textbook *Protective Groups in Organic Synthesis* Greene, T. W.; Wuts, P. G. M. Wiley Interscience, (1991) ISBN 0471623016. The protected amine can be prepared in a similar manner as described in the literature by reaction of properly substituted (2-mercapto-benzyl)-methyl-carbamic acid ester with properly substituted 4-halo indole or 4-pseudohalo indole, where "halo" is either bromo or iodo and "pseudohalo" is e.g. triflate or nonaflate, according to Schopfer, H.; Schlapbach, U.; *Tetrahedron* 2001, 57, 3069-3073. When $R^{13}$=hydrogen in formula XII, then this position is protected prior to the coupling reaction and deprotected after the coupling reaction according to standard literature procedures with standard protection groups, e.g. a 4-methyl-phenyl-sulfonyl group or a tert-butoxy-carbonyl group. The properly substituted (2-mercapto-benzyl)-methyl-carbamic acid ester can be prepared from the properly substituted (2-bromo-benzyl)-methyl-carbamic acid ester or properly substituted (2-iodo-benzyl)-methyl-carbamic acid ester in a palladium catalysed coupling reaction with a trialkylsilane thiol with subsequent desilylation with a fluoride donor such as tetrabutylammonium fluoride (Winn, M.; et al. *J. Med. Chem.* 2001, 44, 4393-4403).

The deprotection according to method 10 can be performed as described in method 9. The protected amine can be prepared from the properly substituted (2-mercapto-benzyl)-methyl-carbamic acid ester and the properly substituted 5-halo indole or 5-pseudohalo indole, where "halo" is either bromo or iodo and "pseudohalo" is e.g. triflate or nonaflate, as described in method 9. When $R^{13}$=hydrogen in formula XIII, then this position is protected prior to the coupling reaction and deprotected after the coupling reaction according to standard literature procedures with standard protection groups, e.g. a 4-methyl-phenyl-sulfonyl group or a tert-butoxy-carbonyl group.

The deprotection according to method 11 can be performed as described in method 9. The protected amine can be prepared from the properly substituted (2-mercapto-benzyl)-methyl-carbamic acid ester and the properly substituted 6-halo indole or 6-pseudohalo indole, where "halo" is either bromo or iodo and "pseudohalo" is e.g. triflate or nonaflate, as described in method 9. When $R^{13}$=hydrogen in formula XIV, then this position is protected prior to the coupling reaction and deprotected after the coupling reaction according to standard literature procedures with standard protection groups, e.g. a 4-methyl-phenyl-sulfonyl group or a tert-butoxy-carbonyl group.

The deprotection according to method 12 can be performed as described in method 9. The protected amine can be prepared from the properly substituted (2-mercapto-benzyl)-methyl-carbamic acid ester and the properly substituted 7-halo indole or 7-pseudohalo indole, where "halo" is either bromo or iodo and "pseudohalo" is e.g. triflate or nonaflate, as described in method 9. When $R^{13}$=hydrogen in formula XV, then this position is protected prior to the coupling reaction and deprotected after the coupling reaction according to standard literature procedures with standard protection groups, e.g. a 4-methyl-phenyl-sulfonyl group or a tert-butoxy-carbonyl group.

The invention disclosed herein is further illustrated by the following non-limiting examples.

EXAMPLES

General Methods

Analytical LC-MS data were obtained on a PE Sciex API 150EX instrument equipped with photoionization (APPI) ion source and Shimadzu LC-8A/SLC-10A LC system. The LC conditions (Symmetry C18 column 4.6×30 mm with a particle size of 3.5 gm) were linear gradient elution with eluents A (water containing 0.05% TFA) and B (acetonitrile containing 5% water and 0.035% TFA). Gradient (time[min]% B): (0.00/10.0); (4.00/100.0); (4.10/10.0); (5.00/10.0) with 2 mL/min. Purity was determined by integration of the UV trace (254 nm) and ELS (SEDERE SEDEX 55 with Heto CBN 8-30 cooling bath). The retention times, $R_t$, are expressed in minutes.

Mass spectra were obtained by an alternating scan method to give molecular weight information. The molecular ion, MH+, was obtained at low orifice voltage (5V) and fragmentation at high orifice voltage (100V).

Preparative LC-MS-separation was performed on the same instrument. The LC conditions (Symmetry C18 column 10×50 mm) were linear gradient elution with eluents A (water containing 0.05% TFA) and B (acetonitrile containing 5% water and 0.035% TFA): (time[min]% B): (0.00/20.0); (7.00/100.0); (7.10/20.0); (8.00/20.0) with 5.7 mL/min Fraction collection was performed by split-flow MS detection.

For column chromatography silica gel of formula Kieselgel 60, 230-400 mesh ASTM was used. For ion-exchange chromatography (SCX, 1 g, Varian Mega Bond Elut®, Chrompack cat. No. 220776) was used. Prior to use the SCX-columns were pre-conditioned with 10% solution of acetic acid in methanol (3 mL).

Preparation of Intermediates

Example 1

2-(1H-Indol-3-ylsulfanyl)-N,N-dimethyl benzamide

N,N,N',N'-Tetramethyl-2,2'-dithiodibenzamide (Elworthy, Todd R.; Ford, Anthony P. D. W.; Bantle, Gary W.; Morgans, David J.; Ozer, Rachel S.; et al. *J. Med. Chem.* 40, 1997, 2674-2687) (12.80 g, 35.5 mmol) was dissolved in 1,2-dichloroethane (200 mL) under Ar, and sulfurylchloride (2.9 mL, 4.84 g, 35.9 mmol) was carefully added with stirring under Ar. The reaction mixture was stirred for 15 min at room temperature and the resulting solution was added slowly (dropwise) to an icecold solution (0° C.) of indole (8.4 g, 71.7 mmol) in dry DMF (180 mL) under Ar. The mixture was stirred at 0° C. under Ar for 2.5 hours and then quenched by addition of water (180 mL) and sat. aqueous NaHCO₃ (150 mL). To the resulting emulsion was added ethyl acetate (250 mL). The organic phases were combined and washed with brine (100 mL). The water phase was further extracted with ethyl acetate (2×100 mL) and the combined organic phases were washed with brine and dried over MgSO₄ and evaporated in vacuo to a dark orange oil which crystallized upon standing. The product was purified and isolated by recrystallisation (acetonitrile) to give 5.53 g (26%) crystalline product (m.p. 195.6-197.6° C.). From the motherliq. was further 4.45 g (21%) product isolated (m.p. 194.3-196.4° C.).

The following compounds were prepared in a similar way:
2-(4-Chloro-1H-indol-3-ylsulfanyl)-N,N-dimethyl benzamide
2-(4-Fluoro-1H-indol-3-ylsulfanyl)-N,N-dimethyl benzamide
2-(4-Fluoro-1H-indol-3-ylsulfanyl)-N,N-dimethyl benzamide
2-(5-Fluoro-1H-indol-3-ylsulfanyl)-N,N-dimethyl benzamide
2-(5-Chloro-1H-indol-3-ylsulfanyl)-N,N-dimethyl benzamide
N,N-Dimethyl-2-(7-methyl-1H-indol-3-ylsulfanyl)benzamide 2-(5-Methoxy-1H-indol-3-ylsulfanyl)-N,N-dimethyl benzamide
2-(6-Fluoro-1H-indol-3-ylsulfanyl)-N,N-dimethyl benzamide
2-(6-Chloro-1H-indol-3-ylsulfanyl)-N,N-dimethyl benzamide
N,N-Dimethyl-2-(2-methyl-1H-indol-3-ylsulfanyl)benzamide
2-(6-Hydroxy-1H-indol-3-ylsulfanyl)-N,N-dimethyl benzamide
2-(7-Methoxy-1H-indol-3-ylsulfanyl)-N,N-dimethyl benzamide
N,N-Dimethyl-2-(4-methyl-1H-indol-3-ylsulfanyl)benzamide
N,N-Dimethyl-2-(7-nitro-1H-indol-3-ylsulfanyl)benzamide
2-(4-Hydroxy-1H-indol-3-ylsulfanyl)-N,N-dimethyl benzamide
2-(4-Cyano-1H-indol-3-ylsulfanyl)-N,N-dimethyl benzamide
2-(6-Cyano-1H-indol-3-ylsulfanyl)-N,N-dimethyl benzamide
2-(7-Chloro-1H-indol-3-ylsulfanyl)-N,N-dimethyl benzamide
2-(6-Methoxy-1H-indol-3-ylsulfanyl)-N,N-dimethyl benzamide
N,N-Dimethyl-2-(1-methyl-1H-indol-3-ylsulfanyl)benzamide
2-(4-Methoxy-1H-indol-3-ylsulfanyl)-N,N-dimethyl benzamide
N,N-Dimethyl-2-(6-methyl-1H-indol-3-ylsulfanyl)benzamide Example 2

2-(1H-Indol-3-ylsulfanyl)-N-methyl benzamide

Carbonyldiimidazole (11 mmol) was added to a solution of 2-(1H-indol-3-ylsulfanyl)benzoic acid (Hamel, P.; Girard, M.; Tsou, N. N.; *J. Heterocycl. Chem.* 36, 1999, 643-652) (10 mmol) in dry THF (200 mL) and refluxed for 60 minutes under argon. Methyl amine (1M in THF; 40 ml) was added slowly to the reaction mixture and the mixture was stirred at room temperature for 16 hours. The mixture was evaporated in vacuo and the product purified by column chromatography on silica gel using ethyl acetate as an eluent.

The following compounds were prepared in a similar way:
2-(5-Fluoro-1H-indol-3-ylsulfanyl)-N-methyl benzamide
2-(6-Fluoro-1H-indol-3-ylsulfanyl)-N-methyl benzamide
2-(2-Methyl-1H-indol-3-ylsulfanyl)-N-methyl benzamide
2-(4-Methyl-1H-indol-3-ylsulfanyl)-N-methyl benzamide
2-(4-Chloro-1H-indol-3-ylsulfanyl)-N-methyl benzamide Example 3

(2-mercapto-benzyl)-methyl-carbamic acid tert-butyl ester (2-Iodo-benzyl)-methyl-carbamic acid tert-butyl ester (5.0 g, 14.4 mmol) in dry toluene (30 mL) was placed in two Emrys Optimizer EXP 20 mL tubes. To each tube tris(dibenzylideneacetone)dipalladium (66 mg, 0.072 mmol), bis(2-diphenylphosphinophenyl)ether (78 mg, 0.14 mmol), triisopropylsilanethiol (1.44 g, 7.56 mmol) and sodium tert-butoxide (900 mg, 9.36 mmol) were added sequentially. The tubes were sealed and subjected to microwave heating at 160° C. for 15 minutes. After cooling the mixture, the product was eluted through a plug of silica with ethyl acetate-heptane (1:10) to give 5.2 g (88%) of methyl-(2-triisopropylsilanyl-sulfanyl-benzyl)-carbamic acid tert-butyl ester. This product was dissolved in THF (70 mL) and cooled to 0° C. Tetrabutylammonium fluoride trihydrate (4.21 g, 13.3 mmol) dissolved in THF (40 mL) was added dropwise at 0° C. and the mixture was stirred at this temperature for 15 minutes. The crude mixture was poured onto a plug of silica gel and the product was eluted with ethyl acetate-heptane (1:2) to give 3.2 g (100%) of (2-mercapto-benzyl)-methyl-carbamic acid tert-butyl ester contaminated with traces of triisopropylsilane fluoride.

Example 4

Compounds of the Invention of Formula I

Synthesis of
1. [2-(1H-Indol-3-ylsulfanyl)benzyl]dimethyl amine 2-(1H-Indol-3-ylsulfanyl)-N,N-dimethyl benzamide (1 mmol) was dissolved in dry tetrahydrofuran (30 mL). To the mixture was added 3 mL 1 M borane in tetrahydrofuran and the mixture was stirred at room temperature for 24 hours. Methanol (5 mL) was added and the mixture stirred at room temperature for 30 min and then evaporated in vacuo. The mixture was redissolved in ethyl acetate (100 mL) and washed with saturated sodium hydrogen carbonate (20 mL), dried over anhydrous MgSO$_4$ and evaporated in vacuo. The product was crystallized as an oxalate salt by dissolution in acetone and addition of one equivalent of oxalic acid.

The following compounds were prepared in a similar way and analytical data are shown in Table 1.:
2. [2-(5-cyano-1H-indol-3-ylsulfanyl)benzyl] dimethyl amine
3. [2-(4-Fluoro-1H-indol-3-ylsulfanyl)benzyl] dimethyl amine
4. [2-(4-Chloro-1H-indol-3-ylsulfanyl)benzyl] dimethyl amine
5. [2-(5-Fluoro-1H-indol-3-ylsulfanyl)benzyl] dimethyl amine
6. [2-(5-Chloro-1H-indol-3-ylsulfanyl)benzyl] dimethyl amine
7. Dimethyl-[2-(7-methyl-1H-indol-3-ylsulfanyl)benzyl] amine
8. [2-(7-Methoxy-1H-indol-3-ylsulfanyl)benzyl] dimethyl amine
9. [2-(5-Methoxy-1H-indol-3-ylsulfanyl)benzyl] dimethyl amine
10. [2-(6-Fluoro-1H-indol-3-ylsulfanyl)benzyl] dimethyl amine
11. [2-(6-Chloro-1H-indol-3-ylsulfanyl)benzyl] dimethyl amine
12. Dimethyl-[2-(2-methyl-1H-indol-3-ylsulfanyl)benzyl] amine
13. Dimethyl-[2-(6-methyl-1H-indol-3-ylsulfanyl)benzyl] amine
14. [2-(4-cyano-1H-indol-3-ylsulfanyl)benzyl] dimethyl amine
15. Dimethyl-[2-(1-methyl-1H-indol-3-ylsulfanyl)benzyl] amine
16. Dimethyl-[2-(4-methyl-1H-indol-3-ylsulfanyl)benzyl] amine
17. Dimethyl-[2-(4-hydroxy-1H-indol-3-ylsulfanyl)benzyl] amine
18. [2-(6-cyano-1H-indol-3-ylsulfanyl)benzyl] dimethyl amine 19. [2-(7-Chloro-1H-indol-3-ylsulfanyl)benzyl] dimethyl amine
20. [2-(6-Methoxy-1H-indol-3-ylsulfanyl)benzyl] dimethyl amine
21. [2-(4-Methoxy-1H-indol-3-ylsulfanyl)benzyl] dimethyl amine Example 5

Compounds of Formula I

Synthesis of
22. [2-(1H-Indol-3-ylsulfanyl)benzyl]methyl amine

2-Methyl-2,3-dihydro-benzoisothiazole (VI) (Hoffmann, R. W.; Goldman, S. Chem. Ber. 111, 1978, 2716-2725) (75 mg, 0.50 mmol) was dissolved in THF (1 mL) and added to indole (V) (140 mg, 0.60 mmol) under Ar. Tricloroacetic acid (90 mg, 0.55 mmol) was added and the reaction mixture was stirred at room temperature for 16 hours. 2 mL 1N NaOH (aq) was added. Extraction with ethyl acetate (2×10 mL) and purification by flash chromatography on silica gel (eluent: ethyl acetate then ethyl acetate/methanol/triethylamine) gave 88 mg [2-(1H-Indol-3-ylsulfanyl)benzyl]methyl amine (67% yield).

The following compounds were prepared in a similar way and analytical data are shown in Table 1:
23. [2-(6-Fluoro-1H-indol-3-ylsulfanyl)benzyl]methyl amine
24. [2-(5-Fluoro-1H-indol-3-ylsulfanyl)benzyl]methyl amine
25. Methyl-[2-(4-methyl-1H-indol-3-ylsulfanyl)benzyl] amine
26. [2-(4-Chloro-1H-indol-3-ylsulfanyl)benzyl]methyl amine
27. Methyl-[2-(2-methyl-1H-indol-3-ylsulfanyl)benzyl] amine
28. [2-(5-Fluoro-2-methyl-1H-indol-3-ylsulfanyl)-benzyl] methyl amine
29. Methyl-[2-(5-methyl-1H-indol-3-ylsulfanyl)benzyl] amine
30. Methyl-[2-(7-methyl-1H-indol-3-ylsulfanyl)benzyl] amine
31. [2-(4-Fluoro-1H-indol-3-ylsulfanyl)benzyl]methyl amine
32. [2-(7-Ethyl-1H-indol-3-ylsulfanyl)benzyl]methyl amine
33. [2-(6-Methoxy-1H-indol-3-ylsulfanyl)benzyl]methyl amine
34. [2-(5-Chloro-1H-indol-3-ylsulfanyl)benzyl]methyl amine
35. [2-(6-Chloro-1H-indol-3-ylsulfanyl)benzyl]methyl amine
36. [2-(5-Methoxy-4-methyl-1H-indol-3-ylsulfanyl)-benzyl]methyl amine
37. [2-(5,6-Dimethoxy-1H-indol-3-ylsulfanyl)-benzyl]methyl amine
38. [2-(6-Bromo-1H-indol-3-ylsulfanyl)benzyl]methyl amine
39. Methyl-[2-(6-methyl-1H-indol-3-ylsulfanyl)-benzyl] amine
40. [2-(4,7-Dimethoxy-1H-indol-3-ylsulfanyl)-benzyl]methyl amine
41. [2-(5-Methoxy-1H-indol-3-ylsulfanyl)benzyl]methyl amine
42. [2-(4-Methoxy-1H-indol-3-ylsulfanyl)benzyl]methyl amine
43. [2-(5-Bromo-1H-indol-3-ylsulfanyl)-benzyl]methyl amine
44. [2-(7-Methoxy-1H-indol-3-ylsulfanyl)benzyl]methyl amine
45. [5-Chloro-2-(1H-indol-3-ylsulfanyl)-benzyl]methyl amine
46. Methyl-[2-(6-trifluoromethyl-1H-indol-3-ylsulfanyl)-benzyl] amine
47. [5-Hydroxy-2-(1H-indol-3-ylsulfanyl)-benzyl]methyl amine
48. [2-(4-Bromo-1H-indol-3-ylsulfanyl)-benzyl]methyl amine
49. [2-(7-Chloro-1H-indol-3-ylsulfanyl)-benzyl]methyl amine
50. [2-(5-Iodo-1H-indol-3-ylsulfanyl)-benzyl]methyl amine
51. [2-(6-Cyano-1H-indol-3-ylsulfanyl)-benzyl]methyl amine
52. [2-(1H-Indol-3-ylsulfanyl)-5-methyl-benzyl]methyl amine
53. [2-(3-methyl-1H-indol-2-ylsulfanyl)-benzyl]methyl amine
54. [2-(5,6-Dimethoxy-1H-indol-3-ylsulfanyl)-5-fluoro-benzyl]-methyl-amine
55. [5-Fluoro-2-(3-methyl-1H-indol-2-ylsulfanyl)-benzyl]-methyl-amine
56. [5-Fluoro-2-(4-fluoro-1H-indol-3-ylsulfanyl)-benzyl]-methyl-amine
57. [2-(4-Chloro-1H-indol-3-ylsulfanyl)-5-fluoro-benzyl]-methyl-amine
58. [2-(7-Chloro-1H-indol-3-ylsulfanyl)-5-fluoro-benzyl]-methyl-amine
59. [5-Fluoro-2-(6-trifluoromethyl-1H-indol-3-ylsulfanyl)-benzyl]-methyl-amine
60. [5-Fluoro-2-(7-methoxy-1H-indol-3-ylsulfanyl)-benzyl]-methyl-amine
61. [2-(4-Bromo-1H-indol-3-ylsulfanyl)-5-fluoro-benzyl]-methyl-amine
62. 3-(4-Fluoro-2-methylaminomethyl-phenylsulfanyl)-2-methyl-1H-indol-4-ol
63. 3-(4-Fluoro-2-methylaminomethyl-phenylsulfanyl)-1H-indol-6-ol
64. [5-Fluoro-2-(5-fluoro-1H-indol-3-ylsulfanyl)-benzyl]-methyl-amine
65. [5-Fluoro-2-(4-methoxy-1H-indol-3-ylsulfanyl)-benzyl]-methyl-amine
66. [2-(6-Chloro-1H-indol-3-ylsulfanyl)-5-fluoro-benzyl]-methyl-amine
67. [2-(5-Chloro-1H-indol-3-ylsulfanyl)-5-fluoro-benzyl]-methyl-amine
68. [5-Fluoro-2-(6-methyl-1H-indol-3-ylsulfanyl)-benzyl]-methyl-amine
69. [5-Fluoro-2-(5-methoxy-4-methyl-1H-indol-3-ylsulfanyl)-benzyl]-methyl-amine
70. [2-(5-Bromo-1H-indol-3-ylsulfanyl)-5-fluoro-benzyl]-methyl-amine
71. [5-Fluoro-2-(5-methoxy-1H-indol-3-ylsulfanyl)-benzyl]-methyl-amine
72. [2-(6-Bromo-1H-indol-3-ylsulfanyl)-5-fluoro-benzyl]-methyl-amine
73. [5-Fluoro-2-(6-fluoro-1H-indol-3-ylsulfanyl)-benzyl]-methyl-amine
74. [5-Fluoro-2-(6-methoxy-1H-indol-3-ylsulfanyl)-benzyl]-methyl-amine
75. [5-Fluoro-2-(2-methyl-1H-indol-3-ylsulfanyl)-benzyl]-methyl-amine
76. [5-Fluoro-2-(5-methyl-1H-indol-3-ylsulfanyl)-benzyl]-methyl-amine 77. [5-Fluoro-2-(4-methyl-1H-indol-3-ylsulfanyl)-benzyl]-methyl-amine
78. [5-Fluoro-2-(7-methyl-1H-indol-3-ylsulfanyl)-benzyl]-methyl-amine
79. [5-Fluoro-2-(1-methyl-1H-indol-3-ylsulfanyl)-benzyl]-methyl-amine
80. [5-Fluoro-2-(5-fluoro-2-methyl-1H-indol-3-ylsulfanyl)-benzyl]-methyl-amine
81. [5-Chloro-2-(5-fluoro-1H-indol-3-ylsulfanyl)-benzyl]-methyl-amine
82. [5-Chloro-2-(5-methoxy-1H-indol-3-ylsulfanyl)-benzyl]-methyl-amine
83. [5-Chloro-2-(7-methyl-1H-indol-3-ylsulfanyl)-benzyl]-methyl-amine
84. [5-Chloro-2-(1-methyl-1H-indol-3-ylsulfanyl)-benzyl]-methyl-amine
85. [5-Chloro-2-(4-methoxy-1H-indol-3-ylsulfanyl)-benzyl]-methyl-amine
86. [5-Chloro-2-(7-methoxy-1H-indol-3-ylsulfanyl)-benzyl]-methyl-amine
87. [5-Chloro-2-(6-fluoro-1H-indol-3-ylsulfanyl)-benzyl]-methyl-amine
88. [5-Chloro-2-(5-fluoro-2-methyl-1H-indol-3-ylsulfanyl)-benzyl]-methyl-amine
89. [2-(5-Fluoro-2-methyl-1H-indol-3-ylsulfanyl)-5-methyl-benzyl]-methyl-amine
90. Methyl-[5-methyl-2-(4-methyl-1H-indol-3-ylsulfanyl)-benzyl]-amine
91. [2-(7-Ethyl-1H-indol-3-ylsulfanyl)-5-methyl-benzyl]-methyl-amine
92. [2-(6-Methoxy-1H-indol-3-ylsulfanyl)-5-methyl-benzyl]-methyl-amine
93. Methyl-[5-methyl-2-(2-methyl-1H-indol-3-ylsulfanyl)-benzyl]-amine
94. [2-(4-Methoxy-1H-indol-3-ylsulfanyl)-5-methyl-benzyl]-methyl-amine
95. [2-(6-Bromo-1H-indol-3-ylsulfanyl)-5-methyl-benzyl]-methyl-amine
96. [2-(6-Fluoro-1H-indol-3-ylsulfanyl)-5-methyl-benzyl]-methyl-amine
97. [2-(4-Fluoro-1H-indol-3-ylsulfanyl)-5-methyl-benzyl]-methyl-amine
98. 3-(4-Methyl-2-methylaminomethyl-phenylsulfanyl)-1H-indol-6-ol
99. [5-Chloro-2-(5-methyl-1H-indol-3-ylsulfanyl)-benzyl]-methyl-amine
100. [2-(6-Chloro-1H-indol-3-ylsulfanyl)-5-methyl-benzyl]-methyl-amine
101. [2-(5-Chloro-1H-indol-3-ylsulfanyl)-5-methyl-benzyl]-methyl-amine
105. [4-Chloro-2-(6-methyl-1H-indol-3-ylsulfanyl)-benzyl]-methyl-amine
106. [4-Chloro-2-(2-methyl-1H-indol-3-ylsulfanyl)-benzyl]-methyl-amine
107. [4-Chloro-2-(5-methyl-1H-indol-3-ylsulfanyl)-benzyl]-methyl-amine
108. [4-Chloro-2-(7-methyl-1H-indol-3-ylsulfanyl)-benzyl]-methyl-amine
109. [4-Chloro-2-(4-methyl-1H-indol-3-ylsulfanyl)-benzyl]-methyl-amine
110. [4-Chloro-2-(5-fluoro-1H-indol-3-ylsulfanyl)-benzyl]-methyl-amine
111. [4-Chloro-2-(6-fluoro-1H-indol-3-ylsulfanyl)-benzyl]-methyl-amine
112. [4-Chloro-2-(4-fluoro-1H-indol-3-ylsulfanyl)-benzyl]-methyl-amine
113. [4-Chloro-2-(7-fluoro-1H-indol-3-ylsulfanyl)-benzyl]-methyl-amine
114. [4-Chloro-2-(7-ethyl-1H-indol-3-ylsulfanyl)-benzyl]-methyl-amine
115. [4-Chloro-2-(5-methoxy-4-methyl-1H-indol-3-ylsulfanyl)-benzyl]-methyl-amine
116. [4-Chloro-2-(5-methoxy-1H-indol-3-ylsulfanyl)-benzyl]-methyl-amine
117. [4-Chloro-2-(6-methoxy-1H-indol-3-ylsulfanyl)-benzyl]-methyl-amine
118. [4-Chloro-2-(7-methoxy-1H-indol-3-ylsulfanyl)-benzyl]-methyl-amine
119. [4-Chloro-2-(4-methoxy-1H-indol-3-ylsulfanyl)-benzyl]-methyl-amine
120. [4-Chloro-2-(5-chloro-1H-indol-3-ylsulfanyl)-benzyl]-methyl-amine
121. [4-Chloro-2-(6-chloro-1H-indol-3-ylsulfanyl)-benzyl]-methyl-amine
122. [4-Chloro-2-(4-chloro-1H-indol-3-ylsulfanyl)-benzyl]-methyl-amine
123. [4-Chloro-2-(7-chloro-1H-indol-3-ylsulfanyl)-benzyl]-methyl-amine
124. [4-Chloro-2-(1H-indol-3-ylsulfanyl)-benzyl]-methyl-amine
125. [4-Chloro-2-(1-methyl-1H-indol-3-ylsulfanyl)-benzyl]-methyl-amine
126. [4-Chloro-2-(3-methyl-1H-indol-2-ylsulfanyl)-benzyl]-methyl-amine
127. [4-Chloro-2-(5-fluoro-2-methyl-1H-indol-3-ylsulfanyl)-benzyl]-methyl-amine
129. [2-(5-Fluoro-4-methoxy-1H-indol-3-ylsulfanyl)-benzyl]-methyl-amine
130. [2-(4,5-Difluoro-1H-indol-3-ylsulfanyl)-benzyl]-methyl-amine
131. [2-(4,6-Difluoro-1H-indol-3-ylsulfanyl)-benzyl]-methyl-amine
132. 3-(2-Methylaminomethyl-phenylsulfanyl)-1H-indol-4-ol
134. [2-(5,6-Difluoro-1H-indol-3-ylsulfanyl)-benzyl]-methyl-amine
135. 6-Fluoro-3-(2-methylaminomethyl-phenylsulfanyl)-1H-indol-5-ol
136. [2-(4-Chloro-1H-indol-3-ylsulfanyl)-5-methyl-benzyl]-methyl-amine Example 6

Compounds of Formula I

Synthesis of
102. 5-Fluoro-3-(2-piperidin-1-ylmethyl-phenylsulfanyl)-1H-indole 6 mL conc. $H_2SO_4$ was added to 2,2'-dithiodibenzoic acid (20 g, 65.3 mmol) in 150 mL methanol. The reaction mixture was refluxed for three days, cooled to room temperature and neutralized with sat. aqueous $NaHCO_3$. Methanol was removed in vacuo. The residue was extracted with ethyl acetate. The organic phase was washed with brine, dried with $MgSO_4$ and concentrated in vacuo to give 17.8 g dimethyl 2,2'-dithiodibenzoic acid ester (53.2 mmol, 82%). 1.20 mL Sulfurylchloride (15 mmol) was added to 5.00 g dimethyl 2,2'-dithiodibenzoic acid ester (15 mmol) in 40 mL dry 1,2-dichloroethane under Ar at 0° C. The reaction mixture was stirred 15 min at room temperature and added to 4.10 g fluoro-1H-indole (30.3 mmol) in 50 mL dry THF under Ar. The reaction mixture was stirred for 2 hours at room temperature and then quenched by addition of sat. aqueous NaHCO$_3$. Ethyl acetate was added, the two phases were separated and the organic phase was washed with brine, dried with MgSO$_4$ and concentrated in vacuo. 8.30 g 2-(5-Fluoro-1H-indol-3-ylsulfanyl)-benzoic acid methyl ester (27.5 mmol, 92%) was isolated after flash chromatography on silica gel. 4.15 g 2-(5-Fluoro-1H-indol-3-ylsulfanyl)-benzoic acid methyl ester (13.8 mmol) in 50 mL dry THF was added dropwise to 0.58 g LiAlH$_4$ (15.4 mmol) in 20 mL dry diethyl ether at 0° C. 150 mL dry THF was added and the reaction mixture was stirred 16 hours at room temperature. The reaction was quenched with 1 mL water and 1 mL 2N NaOH. The reaction mixture was stirred for 1 hour, then 2.5 mL water was added and stirring was continued for another hour. The mixture was filtered, dried with MgSO$_4$ and concentrated in vacuo to give 3.00 g 2-(5-fluoro-1H-indol-3-ylsulfanyl)-phenyl]-methanol (11.0 mmol, 80%). 0.275 g p-Toluenesulfonylchloride (1.44 mmol) was added to 0.375 g 2-(5-fluoro-1H-indol-3-ylsulfanyl)-phenyl]-methanol (1.37 mmol) in 5 mL dry THF at 0° C. The reaction mixture was stirred 2 hours at 0° C. and then added to 2.75 mmol piperidine in 10 mL dry THF and stirred 16 hours at room temperature. Water and ethyl acetate were added to the reaction mixture. The two phases were separated and the organic phase was washed with brine, dried with MgSO$_4$ and concentrated in vacuo. 5-Fluoro-3-(2-piperidin-1-ylmethyl-phenylsulfanyl)-1H-indole was isolated after flash chromatography.

The following compounds were prepared in a similar way and analytical data are shown in Table 1:
103. 5-Fluoro-3-(2-morpholin-4-ylmethyl-phenylsulfanyl)-1H-indole
104. 5-Fluoro-3-(2-pyrrolidin-1-ylmethyl-phenylsulfanyl)-1H-indole Example 7

Compounds of Formula I

Synthesis of
128. 2-(5-Fluoro-1H-indol-3-ylsulfanyl)-benzylamine 4.50 g NaBH$_4$ (119 mmol) was added in portions to 7.50 g allyl bromide (62.0 mmol) and 8.35 g 2,2'-dithiodibenzamide (27.4 mmol, prepared from 2,2'-dithiodibenzoic acid via 2,2'-dithiodibenzoic acid chloride) in 80 mL methanol at 0° C. The reaction mixture was stirred 1 hour at room temperature. 50 mL 1N HCl was added and stirring was continued 1 hour. Methanol was removed in vacuo. The residue was extracted with ethyl acetate. The organic phase was washed with brine, dried with MgSO$_4$ and concentrated in vacuo to give 10.0 g 2-allylsulfanyl-benzamide (51.7 mmol, 94%). 2.1 g LiAlH$_4$ (55 mmol) was added to 6.0 g 2-allylsulfanyl-benzamide (31 mmol) in 50 mL dry THF at 0° C. The reaction mixture was stirred for 16 hours at room temperature. The reaction was quenched with 4 mL water and 3 mL 2N NaOH. The reaction mixture was stirred for 1 hour, then 9 mL water was added and stirring was continued for another hour. The mixture was filtered, dried with MgSO$_4$ and concentrated in vacuo to give 5.05 g 2-allylsulfanyl-benzylamine (28.2 mmol, 91%). 2.05 g Di-tert-butyl dicarbonate (9.37 mmol) was added to 1.40 g 2-allylsulfanyl-benzylamine (7.81 mmol) and a catalytic amount of N,N-dimethyl-4-amino pyridine in 20 mL THF. The reaction mixture was stirred for 15 minutes at room temperature. 10 mL 20% citric acid was added and the reaction mixture was stirred for 30 minutes. The reaction mixture was extracted with ethyl acetate, the two phases were separated and the organic phase was washed with brine, dried with MgSO$_4$ and concentrated in vacuo to give (2-allylsulfanyl-benzyl)-carbamic acid tert-butyl ester in quantitative yield. 0.70 g NaIO$_4$ (3.3 mmol) in 20 mL water was added to 0.75 g (2-allylsulfanyl-benzyl)-carbamic acid tert-butyl ester (2.7 mmol) in 20 mL methanol and stirred for 2 hours at room temperature. The reaction mixture was filtered and methanol was removed in vacuo. The residue was extracted with ethyl acetate. The organic phase was washed with brine, dried with MgSO$_4$ and concentrated in vacuo. The residue was redissolved in 5 mL THF and added to 0.50 g fluoro-1H-indole (3.7 mmol) and 0.65 g trichloro acetic acid (4.0 mmol) in 5 mL THF and stirred for 16 hours at 50° C. Sat. aqueous NaHCO$_3$ and ethyl acetate was added, the two phases were separated and the organic phase was washed with brine, dried with MgSO$_4$ and concentrated in vacuo. The residue was purified by flash chromatography and 0.157 g [2-(5-fluoro-1H-indol-3-ylsulfanyl)-benzyl]-carbamic acid tert-butyl ester (0.42 mmol, 16%) was isolated after recrystallization from ethyl acetate/heptane. 8 mL diethyl ether saturated with HCl was added to 0.157 g [2-(5-fluoro-1H-indol-3-ylsulfanyl)-benzyl]-carbamic acid tert-butyl ester (0.42 mmol) in 8 mL methanol and stirred 16 hours. The reaction was neutralized with 2N NaOH and extracted with ethyl acetate. The organic phase was washed with brine, dried with MgSO$_4$ and concentrated in vacuo to give 0.112 g 2-(5-fluoro-1H-indol-3-ylsulfanyl)-benzylamine (98%).

The following compound was prepared in a similar way and analytical data are shown in Table 1:
133. 2-(6-Fluoro-1H-indol-3-ylsulfanyl)-benzylamine Example 8

Compounds of Formula I

Synthesis of
[2-(1H-Indol-5-ylsulfanyl)-benzyl]-methyl-amine (2-Mercapto-benzyl)-methyl-carbamic acid tert-butyl ester (1.85 g, 7.30 mmol) in dry toluene (15 mL) is placed in an Emrys Optimizer EXP 20 mL tube. Tris(dibenzylideneacetone) dipalladium (334 mg, 0.37 mmol), bis(2-diphenylphosphinophenyl)ether (197 mg, 0.37 mmol), tert-butyl-5-bromoindole-1-carboxylate (2.38 g, 8.03 mmol) and potassium tert-butoxide (860 mg, 7.67 mmol) are added. The reaction vessel is sealed and subjected to microwave heating at 160° C. for 15 minutes. Upon cooling the mixture is poured onto a plug of silica and the product is eluted with ethyl acetate-heptane (1:4). 0.67 g (20%) of 5-{2-[(tert-butoxycarbonyl-methyl-amino)-methyl]-phenylsulfanyl}-indole-1-carboxylic acid tert-butyl ester is isolated and used in the next step whithout further purification. 5-{2-[(tert-butoxycarbonyl-methyl-amino)-methyl]-phenylsulfanyl}-indole-1-carboxylic acid tert-butyl ester (0.67 g, 1.43 mmol) in methanol (15 mL) and diethyl ether saturated with hydrochloric acid (15 mL) is stirred at room temperature for 1 hour and concentrated in vacuo. Ice/water is added to the remanence and 28% aqueous NaOH is added until pH 9. The aqueous fraction is extracted with ethyl acetate (3×15 mL). Combined organic fractions are dried with MgSO$_4$ and concentrated in vacuo. The product is purified by silica gel chromatography eluting with ethyl acetate-triethyl amine (100:4) followed by ethyl acetate-ethanol-triethyl amine (100:5:5). Upon evaporation of the volatiles, 40 mg (10%) of [2-(1H-indol-5-ylsulfanyl)-benzyl]-methyl-amine is isolated.

The following compounds are prepared in a similar way:
[2-(1H-Indol-4-ylsulfanyl)-benzyl]-methyl-amine
[2-(1H-Indol-6-ylsulfanyl)-benzyl]-methyl-amine
[2-(1H-Indol-7-ylsulfanyl)-benzyl]-methyl-amine

TABLE 1

Measured molecular mass, measured HPLC-retention time ($R_t$, min) and UV- and ELSD-purities (%).

| compound | $R_t$ (min.) | UV-purity (%) | ELSD-purity (%) | M + H⁺ |
|---|---|---|---|---|
| 1 | 1.79 | 97.9 | 100 | 283.2 |
| 2 | 1.75 | 80.6 | 96.5 | 307.9 |
| 3 | 1.83 | 98.0 | 97.1 | 300.8 |
| 4 | 1.91 | 95.4 | 98.2 | 317.1 |
| 5 | 1.83 | 98.8 | 99.3 | 301.1 |
| 6 | 2.04 | 99.4 | 99.1 | 317.1 |
| 7 | 2.00 | 97.9 | 97.4 | 297.2 |
| 8 | 1.91 | 96.8 | 98.3 | 313.1 |
| 9 | 1.79 | 98.9 | 100 | 313.2 |
| 10 | 1.91 | 99.5 | 100 | 301.1 |
| 11 | 2.08 | 96.1 | 100 | 316.8 |
| 12 | 1.87 | 95.2 | 99.1 | 297 |
| 13 | 1.82 | 98.7 | 100.0 | 297.2 |
| 14 | 1.56 | 95.2 | 100.0 | 308 |
| 15 | 1.88 | 98.3 | 100.0 | 297.1 |
| 16 | 1.81 | 99.2 | 100.0 | 297.1 |
| 17 | 1.49 | 75.0 | 91.5 | 299 |
| 18 | 1.68 | 90.0 | 95.0 | 308 |
| 19 | 1.96 | 90.5 | 95.6 | 316.8 |
| 20 | 1.77 | 88.7 | 96.0 | 313.1 |
| 21 | 1.75 | 87.3 | 96.9 | 313 |
| 22 | 1.79 | 98.5 | 97.5 | 269 |
| 23 | 1.95 | 100 | 95.4 | 287 |
| 24 | 1.94 | 99.2 | 95.8 | 286.8 |
| 25 | 1.93 | 97.2 | 97.0 | 283.3 |
| 26 | 1.90 | 98.2 | 96.3 | 303 |
| 27 | 1.87 | 97.4 | 96.8 | 283.1 |
| 28 | 2.01 | 97.0 | 99.1 | 301.1 |
| 29 | 1.85 | 98.0 | 99.9 | 283 |
| 30 | 1.89 | 98.1 | 99.8 | 283 |
| 31 | 1.72 | 97.9 | 99.7 | 286.9 |
| 32 | 2.02 | 97.9 | 100 | 297.1 |
| 33 | 1.72 | 99.5 | 99.9 | 299.1 |
| 34 | 1.92 | 97.7 | 100 | 303.1 |
| 35 | 1.97 | 96.5 | 99.9 | 303.1 |
| 36 | 1.81 | 98.8 | 99.8 | 313.2 |
| 37 | 1.51 | 97.7 | 99.6 | 329.1 |
| 38 | 2.00 | 97.5 | 99.8 | 346.9 |
| 39 | 1.87 | 80.6 | 99.0 | 283.1 |
| 40 | 1.73 | 84.1 | 97.9 | 329.1 |
| 41 | 1.68 | 87.5 | 98.5 | 299.1 |
| 42 | 1.66 | 87.6 | 99.4 | 299 |
| 43 | 1.98 | 93.7 | 98.7 | 348.8 |
| 44 | 1.78 | 93.7 | 99.3 | 299.1 |
| 45 | 2.45 | 84.3 | 85.4 | 303.3 |
| 46 | 2.05 | 96.8 | 100 | 337.1 |
| 47 | 1.30 | 93.4 | 100 | 285.1 |
| 48 | 1.83 | 92.4 | 100 | 348.8 |
| 49 | 1.92 | 90.6 | 99.9 | 303 |
| 50 | 2.00 | 88.6 | 99.6 | 395.1 |
| 51 | 1.62 | 86.1 | 98.5 | 293.8 |
| 52 | 1.82 | 97.0 | 99.7 | 283.3 |
| 53 | 2.04 | 95.9 | 99.7 | 283.4 |
| 54 | 1.56 | 73.92 | 98.05 | 347.0 |
| 55 | 2.10 | 74.19 | 96.08 | 299.1 |
| 56 | 1.76 | 78.09 | 100.00 | 304.9 |
| 57 | 1.88 | 80.25 | 99.77 | 320.8 |
| 58 | 1.97 | 80.83 | 98.86 | 320.9 |
| 59 | 2.12 | 84.31 | 99.11 | 355.1 |
| 60 | 1.83 | 86.68 | 99.15 | 317.1 |
| 61 | 1.90 | 87.33 | 99.75 | 367.0 |
| 62 | 1.64 | 88.10 | 99.61 | 317.0 |
| 63 | 1.41 | 88.77 | 99.74 | 303.1 |
| 64 | 1.83 | 91.91 | 100.00 | 304.8 |
| 65 | 1.74 | 92.27 | 100.00 | 317.1 |
| 66 | 2.00 | 93.20 | 99.91 | 321.1 |
| 67 | 1.97 | 93.68 | 100.00 | 320.9 |
| 68 | 1.92 | 93.80 | 99.97 | 301.0 |
| 69 | 1.85 | 94.35 | 100.00 | 329.1 |
| 70 | 2.00 | 94.52 | 99.86 | 367.0 |
| 71 | 1.73 | 95.29 | 99.88 | 317.1 |
| 72 | 2.04 | 95.56 | 99.80 | 367.0 |
| 73 | 1.85 | 95.67 | 100.00 | 305.0 |
| 74 | 1.76 | 96.68 | 99.95 | 317.1 |
| 75 | 1.82 | 97.23 | 100.00 | 301.1 |
| 76 | 1.91 | 97.71 | 100.00 | 301.1 |
| 77 | 1.89 | 97.73 | 99.96 | 301.1 |
| 78 | 1.93 | 97.79 | 99.95 | 301.1 |
| 79 | 1.96 | 98.85 | 99.95 | 301.0 |
| 80 | 1.88 | 99.01 | 99.86 | 319.0 |
| 81 | 1.94 | 86.65 | 99.91 | 320.9 |
| 82 | 1.85 | 72.56 | 100.00 | 332.8 |
| 83 | 2.03 | 94.94 | 99.91 | 317.1 |
| 84 | 2.05 | 92.54 | 99.90 | 317.1 |
| 85 | 1.85 | 86.79 | 99.70 | 332.9 |
| 86 | 1.95 | 82.70 | 99.69 | 333.0 |
| 87 | 1.97 | 85.03 | 99.85 | 320.9 |
| 88 | 1.99 | 88.12 | 100.00 | 335.0 |
| 89 | 1.95 | 99.44 | 100.00 | 315.1 |
| 90 | 1.97 | 98.16 | 100.00 | 297.2 |
| 91 | 2.12 | 95.13 | 99.74 | 311.3 |
| 92 | 1.83 | 93.40 | 100.00 | 313.1 |
| 93 | 1.78 | 92.78 | 98.90 | 297.0 |
| 94 | 1.79 | 92.77 | 100.00 | 313.1 |
| 95 | 2.11 | 90.80 | 100.00 | 363.0 |
| 96 | 1.94 | 89.78 | 99.94 | 301.1 |
| 97 | 1.84 | 87.54 | 100.00 | 301.0 |
| 98 | 1.49 | 87.12 | 99.49 | 299.1 |
| 99 | 1.51 | 86.97 | 100.00 | 318.9 |
| 100 | 2.07 | 85.51 | 98.57 | 317.1 |
| 101 | 2.04 | 81.67 | 94.01 | 317.0 |
| 102 | 2.00 | 82.20 | 80.30 | 341.1 |
| 103 | 1.86 | 90.90 | 82.40 | 342.9 |
| 104 | 1.95 | 90.40 | 78.70 | 327.1 |
| 105 | 2.06 | 92.49 | 99.44 | 317.1 |
| 106 | 1.96 | 87.25 | 98.90 | 317.0 |
| 107 | 2.03 | 90.96 | 99.55 | 316.8 |
| 108 | 2.04 | 91.97 | 99.87 | 316.8 |
| 109 | 2.02 | 83.80 | 98.60 | 317.1 |
| 110 | 1.96 | 90.04 | 99.61 | 320.9 |
| 111 | 1.99 | 97.66 | 99.69 | 321.0 |
| 112 | 1.89 | 88.36 | 99.15 | 320.9 |
| 113 | 1.98 | 90.52 | 99.39 | 320.9 |
| 114 | 2.18 | 87.86 | 99.70 | 331.0 |
| 115 | 1.97 | 87.81 | 99.17 | 347.0 |
| 116 | 1.88 | 89.22 | 99.38 | 333.0 |
| 117 | 1.89 | 95.36 | 99.65 | 332.9 |
| 118 | 1.96 | 82.34 | 98.84 | 332.7 |
| 119 | 1.87 | 90.44 | 99.82 | 333.0 |
| 120 | 2.08 | 89.98 | 99.57 | 337.2 |
| 121 | 2.13 | 87.91 | 99.27 | 337.1 |
| 122 | 2.00 | 84.01 | 98.48 | 337.2 |
| 123 | 2.11 | 80.98 | 99.08 | 337.1 |
| 124 | 1.91 | 91.92 | 99.81 | 303.1 |
| 125 | 2.08 | 84.95 | 98.14 | 316.7 |
| 126 | 2.25 | 70.89 | 87.20 | 317.1 |
| 127 | 2.01 | 83.89 | 98.73 | 335.1 |
| 128 | 1.74 | 88.20 | 98.40 | 273.0 |
| 129 | 1.77 | 93.93 | 99.83 | 317.1 |
| 130 | 1.78 | 95.85 | 99.64 | 305.0 |
| 131 | 1.80 | 97.04 | 99.88 | 305.0 |
| 132 | 1.42 | 80.84 | 97.76 | 285.1 |
| 133 | 1.78 | 97.33 | 99.29 | 273.0 |
| 134 | 1.84 | 97.99 | 99.48 | 305.0 |
| 135 | 1.38 | 92.53 | 98.73 | 303.1 |
| 136 | 1.86 | 93.25 | 97.20 | 317.0 |

Example 9

Transporter Binding Assay

Measurements of [$^3$H]-5-HT Uptake into Rat Cortical Synaptosomes

Whole brains from male Wistar rats (125-225 g), excluding cerebellum, are homogenized in 0.32 M sucrose supplemented with 1 mM nialamid with a glass/teflon homogenizer. The homogenate is centrifuged at 600×g for 10 min at 4° C. The pellet is discarded and the supernatant is centrifuged at 20.000×g for 55 min. The final pellet is homogenized (20 sec) in this assay buffer (0.5 mg original tissue/well). Test compounds (or buffer) and 10 nM [$^3$H]-5-HT are added to 96 well plates and shaken briefly. Composition of assay buffer: 123 mM NaCl, 4.82 mM KCl, 0.973 mM CaCl$_2$, 1.12 mM MgSO$_4$, 12.66 mM Na$_2$HPO$_4$, 2.97 mM NaH$_2$PO$_4$, 0.162 mM EDTA, 10 mM glucose and 1 mM ascorbic acid. Buffer is oxygenated with 95% O$_2$/5% CO$_2$ for 10 min at 37° C. and pH is adjusted 7.4. The incubation is started by adding tissue to a final assay volume of 0.2 mL. After 15 min incubation with radioligand at 37° C., samples are filtered directly on Unifilter GF/C glass fiber filters (soaked for 1 hour in 0.1% polyethylenimine) under vacuum and immediately washed with 3×0.2 ml assay buffer. Non-specific uptake is determined using citalopram (10 μM final concentration). Citalopram is included as reference in all experiments as dose-response curve.

Measurements of [$^3$H]Noradrenaline Uptake into Rat Cortical Synaptosomes

Fresh cortex from male Wistar rats (125-225 g) are homogenized in 0.4M sucrose with a glass/teflon homogenizer. The homogenate is centrifuged at 600×g for 10 min at 4° C. The pellet is discarded and the supernatant is centrifuged at 20.000×g for 55 min. The final pellet is homogenized (20 sec) in this assay buffer (6 mg original tissue/mL=4 mg/well). Test compounds (or buffer) and 10 nM [$^3$H]-noradrenaline are added to deep 96 well plates and shaken briefly. Composition of assay buffer: 123 mM NaCl, 4.82 mM KCl, 0.973 mM CaCl$_2$, 1.12 mM MgSO$_4$, 12.66 mM Na$_2$HPO$_4$, 2.97 mM NaH$_2$PO$_4$, 0.162 mM EDTA, 10 mM glucose and 1 mM ascorbic acid. Buffer is oxygenated with 95% O$_2$/5% CO$_2$ for 10 min at 37° C. and pH is adjusted 7.4. The incubation is started by adding tissue to a final assay volume of 1 ml. After 15 min incubation with radioligand at 37° C., samples are filtered directly on Unifilter GF/C glass fiber filters (soaked for 1 hour in 0.1% polyethylenimine) under vacuum and immediately washed with 3×1 mL assay buffer. Non-specific uptake is determined using talsupram (10 μM final concentration). Duloxetine is included as reference in all experiments as dose-response curve.

Results of the experiments showed that the tested compounds of the invention inhibit the serotonin and norepinephrine reuptake with IC$_{50}$ below 200 nM.

Measurements of [$^3$H]Dopamine Uptake into Rat Synaptosomes

Tissue preparation: male wistar rats (125-250 g) are sacrificed by decapitated and striatum quickly dissected out and placed in 40 vol (w/v) ice cold 0.40 M sucrose. The tissue is gently homogenised (glass teflon homogeniser) and the P2 fraction is obtained by centrifugation (1000 g, 10 minutes and 40000 g, 20 minutes, 4° C.) and suspended in 560 volumes of a modified Krebs-Ringer-phosphate buffer, pH 7.4.

Tissue 0.25 mg/well (140 μl) (original tissue) is mixed with test suspension. After 5 minutes pre-incubation 12.5 nM 3H-dopamine is added and the mixture is incubated for 5 minutes at RT.

The incubation is terminated by filtering the samples under vacuum through Whatman GF/C filters with a wash of 1 ml buffer. The filters are dried and appropriate scintillation fluid (Optiphase Supermix) is added. After storage for 2 hours in the dark the content of radioactivity is determined by liquid scintillation counting. Uptake is obtained by subtracting the non-specific binding and passive transport measured in the presence of 100 μM of benztropin. For determination of the inhibition of uptake ten concentrations of drugs covering 6 decades are used.

$^3$H-DA=3,4-(ring-2,5,6-$^3$H)dopamine hydrochloride from New England Nuclear, specific activity 30-50 Ci/mmol.

Hyttel, Biochem. Pharmacol. 1978, 27, 1063-1068;

Hyttel, Prog. Neuro-Psychopharmacol. & bil. Psychiat. 1982, 6, 277-295;

Hyttel & Larsen, Acta Pharmacol. Tox. 1985, 56, suppl. 1, 146-153.

The invention claimed is:

1. A compound of the general formula I:

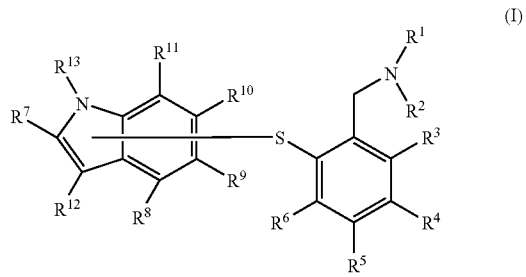

wherein the sulphur atom is attached to the indole via any ring carbon of the indole and wherein $R^1$-$R^2$ are independently selected from hydrogen, $C_{1-6}$-alk(en/yn)yl, $C_{3-8}$-cycloalk(en/yn)yl, and $C_{3-8}$-cycloalk(en/yn)yl-$C_{1-6}$-alk(en/yn)yl or $R^1$ and $R^2$ together with the nitrogen form a 4-7 membered ring containing zero or one double bond, optionally said ring in addition to said nitrogen comprises one further heteroatom selected from nitrogen, oxygen and sulphur;

$R^3$-$R^7$ and $R^9$-$R^{12}$ are independently selected from hydrogen, halogen, cyano, nitro, $C_{1-6}$-alk(en/yn)yl, $C_{3-8}$-cycloalk(en/yn)yl, $C_{3-8}$-cycloalk(en/yn)yl-$C_{1-6}$-alk(en/yn)yl, amino, $C_{1-6}$-alk(en/yn)ylamino, di-($C_{1-6}$-alk(en/yn)yl)amino, $C_{1-6}$-alk(en/yn)ylcarbonyl, aminocarbonyl, $C_{1-6}$-alk(en/yn)ylaminocarbonyl, di-($C_{1-6}$-alk(en/yn)yl)aminocarbonyl, hydroxy, $C_{1-6}$-alk(en/yn)yloxy, $C_{1-6}$-alk(en/yn)ylthio, halo-$C_{1-6}$-alk(en/yn)yl, halo-$C_{1-6}$-alk(en/yn)ylsulfonyl, halo-$C_{1-6}$-alk(en/yn)ylsulfanyl and $C_{1-6}$-alk(en/yn)ylsulfonyl;

$R^8$ is halogen; and $R^{13}$ is selected from hydrogen or $C_{1-6}$-alk(en/yn)yl;

or a pharmaceutically acceptable salt thereof;

with the provisos that:

when the sulphur atom is attached via atom nr. 2 of the indole then $R^7$ does not exist;

when the sulphur atom is attached via atom nr. 3 of the indole then $R^{12}$ does not exist;

when the sulphur atom is attached via atom nr. 4 of the indole then $R^8$ does not exist;

when the sulphur atom is attached via atom nr. 5 of the indole then $R^9$ does not exist;

when the sulphur atom is attached via atom nr. 6 of the indole then $R^{10}$ does not exist; and when the sulphur atom is attached via atom nr. 7 of the indole then $R^{11}$ does not exist.

2. The compound according to claim 1, wherein $R^1$ and $R^2$ are independently selected from hydrogen and $C_{1-6}$-alk(en/yn)yl; or $R^1$ and $R^2$ together with the nitrogen form a 4-7 membered ring containing zero or one double bond, wherein optionally the ring in addition to the nitrogen comprises one further heteroatom selected from the group consisting of nitrogen, oxygen and sulphur.

3. The compound according to claim 1, wherein $R^3$-$R^7$ and $R^9$-$R^{12}$ are independently selected from the group consisting of hydrogen, halogen, cyano, $C_{1-6}$-alk(en/yn)yl, hydroxy, $C_{1-6}$-alk(en/yn)yloxy and halo-$C_{1-6}$-alk(en/yn)yl.

4. The compound according to claim 1 wherein $R^3$-$R^6$ are independently selected from the group consisting of hydrogen, halogen and $C_{1-6}$-alk(en/yn)yl.

5. The compound according to claim 1 wherein $R^7$ and $R^9$-$R^{12}$ are independently selected from the group consisting of hydrogen, halogen, cyano, $C_{1-6}$-alk(en/yn)yl, hydroxy, $C_{1-6}$-alk(en/yn)yloxy and halo-$C_{1-6}$-alk(en/yn)yl.

6. A pharmaceutical composition comprising a compound according to claim 1 and at least one pharmaceutically acceptable carrier or diluent.

7. A compound selected from the group consisting of:
[2-(4-Fluoro-1H-indol-3-ylsulfanyl)benzyl]dimethyl amine;
[2-(4-Chloro-1H-indol-3-ylsulfanyl)benzyl]dimethyl amine;
[2-(4-Chloro-1H-indol-3-ylsulfanyl)benzyl]methyl amine;
[2-(4-Fluoro-1H-indol-3-ylsulfanyl)benzyl]methyl amine;
[2-(4-Bromo-1H-indol-3-ylsulfanyl)-benzyl]methyl amine;
[5-Fluoro-2-(4-fluoro-1H-indol-3-ylsulfanyl)-benzyl]-methyl-amine;
[2-(4-Chloro-1H-indol-3-ylsulfanyl)-5-fluoro-benzyl]-methyl-amine;
[2-(4-Bromo-1H-indol-3-ylsulfanyl)-5-fluoro-benzyl]-methyl-amine;
[2-(4-Fluoro-1H-indol-3-ylsulfanyl)-5-methyl-benzyl]-methyl-amine;
[4-Chloro-2-(4-fluoro-1H-indol-3-ylsulfanyl)-benzyl] methyl-amine;
[4-Chloro-2-(4-chloro-1H-indol-3-ylsulfanyl)-benzyl]-methyl-amine;
[2-(4,5-Difluoro-1H-indol-3-ylsulfanyl)-benzyl]-methyl-amine;
[2-(4,6-Difluoro-1H-indol-3-ylsulfanyl)-benzyl]-methyl-amine; and
[2-(4-Chloro-1H-indol-3-ylsulfanyl)-5-methyl-benzyl]-methyl-amine;

or a pharmaceutically acceptable salt thereof.

8. A pharmaceutical composition comprising a compound according to claim 7 and at least one pharmaceutically acceptable carrier or diluent.

9. A compound that is [2-(4-Fluoro-1H-indol-3-ylsulfanyl)benzyl]dimethyl amine or a pharmaceutically acceptable salt thereof.

10. A compound that is [2-(4-Chloro-1H-indol-3-ylsulfanyl)benzyl]dimethyl amine or a pharmaceutically acceptable salt thereof.

11. A compound that is [2-(4-Chloro-1H-indol-3-ylsulfanyl)benzyl]methyl amine or a pharmaceutically acceptable salt thereof.

12. A compound that is [2-(4-Fluoro-1H-indol-3-ylsulfanyl)benzyl]methyl amine or a pharmaceutically acceptable salt thereof.

13. A compound that is [2-(4-Bromo-1H-indol-3-ylsulfanyl)-benzyl]methyl amine or a pharmaceutically acceptable salt thereof.

14. A compound that is [5-Fluoro-2-(4-fluoro-1H-indol-3-ylsulfanyl)-benzyl]-methyl-amine or a pharmaceutically acceptable salt thereof.

15. A compound that is [2-(4-Chloro-1H-indol-3-ylsulfanyl)-5-fluoro-benzyl]-methyl-amine or a pharmaceutically acceptable salt thereof.

16. A compound that is [2-(4-Bromo-1H-indol-3-ylsulfanyl)-5-fluoro-benzyl]-methyl-amine or a pharmaceutically acceptable salt thereof.

17. A compound that is [2-(4-Fluoro-1H-indol-3-ylsulfanyl)-5-methyl-benzyl]-methyl-amine or a pharmaceutically acceptable salt thereof.

18. A compound that is [4-Chloro-2-(4-fluoro-1H-indol-3-ylsulfanyl)-benzyl]-methyl-amine or a pharmaceutically acceptable salt thereof.

19. A compound that is [4-Chloro-2-(4-chloro-1H-indol-3-ylsulfanyl)-benzyl]-methyl-amine or a pharmaceutically acceptable salt thereof.

* * * * *